US008432611B1

(12) United States Patent
Wach

(10) Patent No.: US 8,432,611 B1
(45) Date of Patent: *Apr. 30, 2013

(54) METHOD AND SYSTEM FOR MANAGING LIGHT AT AN OPTICAL INTERFACE

(75) Inventor: Michael L. Wach, Alpharetta, GA (US)

(73) Assignee: Cirrex Systems, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/371,440

(22) Filed: Feb. 12, 2012

Related U.S. Application Data

(63) Continuation of application No. 12/931,191, filed on Jan. 26, 2011, now Pat. No. 8,116,003, which is a continuation of application No. 11/825,614, filed on Jul. 7, 2007, now Pat. No. 7,903,338.

(60) Provisional application No. 60/819,552, filed on Jul. 8, 2006.

(51) Int. Cl.
*G02B 1/10* (2006.01)

(52) U.S. Cl.
USPC .......................................... 359/587; 359/588

(58) Field of Classification Search .................. 359/581, 359/586–589
See application file for complete search history.

(56) References Cited

U.S. PATENT DOCUMENTS

| 4,747,666 A * | 5/1988 | Ishida ........................... 359/588 |
| 4,947,223 A | 8/1990 | Biefeld et al. |
| 5,009,485 A | 4/1991 | Hall |
| 5,035,485 A * | 7/1991 | Kageyama .................... 359/586 |
| 5,056,099 A | 10/1991 | Bradley |
| 5,181,143 A | 1/1993 | Southwell |
| 5,283,692 A | 2/1994 | Herbst |
| 5,377,045 A | 12/1994 | Wolfe et al. |
| 5,410,431 A * | 4/1995 | Southwell ...................... 359/580 |
| 5,432,638 A | 7/1995 | Rahmlow |
| 5,475,531 A | 12/1995 | Rahmlow et al. |
| 5,488,511 A | 1/1996 | Rahmlow et al. |
| 5,563,734 A | 10/1996 | Wolfe et al. |
| 5,616,401 A | 4/1997 | Kobayashi et al. |
| 5,872,655 A | 2/1999 | Seddon et al. |
| 5,903,585 A | 5/1999 | Dawson et al. |
| 5,923,471 A | 7/1999 | Wood et al. |

(Continued)

OTHER PUBLICATIONS

U.S. Official Action dated Sep. 12, 2011 in U.S. Appl. No. 12/931,191.

(Continued)

*Primary Examiner* — Alessandro Amari
(74) *Attorney, Agent, or Firm* — Hope Baldauff Hartman, LLC

(57) ABSTRACT

An interface between two different optical materials can comprise a stack of thin film layers that manage light incident on that interface. One of the optical materials can have a first composition and a first refractive index, while the other optical material can have a second composition and a second refractive index. The stack can comprise thin film layers of the first optical material interleaved between thin film layers of the second optical material. The layers of the stack can be configured to provide the stack with an aggregate composition of at least one of the optical materials that progressively varies from one end of the stack to the other end. To provide the progressive variation in composition, the layers of one of the optical materials can have a progressively increased thickness across the stack, or can progressively increase in number, for example.

20 Claims, 27 Drawing Sheets

U.S. PATENT DOCUMENTS

| | | | |
|---|---|---|---|
| 5,928,713 | A | 7/1999 | Hualand et al. |
| 6,083,341 | A | 7/2000 | Wei et al. |
| 6,121,068 | A | 9/2000 | Ramdani et al. |
| 6,256,148 | B1 | 7/2001 | Gasworth |
| 6,449,420 | B1 | 9/2002 | Akwani et al. |
| 6,462,878 | B1 | 10/2002 | Kartner et al. |
| 6,842,288 | B1 | 1/2005 | Liu et al. |
| 6,961,183 | B2 | 11/2005 | Wada et al. |
| 7,088,884 | B2 | 8/2006 | Gerken et al. |
| 7,193,780 | B2 * | 3/2007 | Wada et al. ............ 359/586 |

OTHER PUBLICATIONS

U.S. Notice of Allowance dated Dec. 2, 2011 in U.S. Appl. No. 12/931,191.

U.S. Notice of Allowance dated Nov. 22, 2010 in U.S. Appl. No. 11/825,614.

U.S. Official Action dated Jul. 14, 2010 in U.S. Appl. No. 11/825,614.

Oguchi et al. "Dielectric Multi layered Interference Filters Deposited on Polyimide Films," Apr. 25, 1991, Electronic Letters, vol. 27, No. 2.

Espinasse et al., "Detection Reflections, Single and Dual Antireflective Coatings are Critical to Optimizing the Manufacture and Performance of Optical Storage Devices," Mar. 2004, SPIE's oemagazine, pp. 24-26.

Callard et al., "Fabrication and Characterization of Graded Index Silicon Oxynitride Thin Films," Jul./Aug. 1997, Journal of Vacuum Science Technology, A 15(4): 2088-2094.

Machorro et al., "Modification of Refractive Index in Silicon Oxynitride Films During Deposition," Aug. 2000, Material Letters, v 45, pp. 47-50.

Lee et al., "Novel Design Procedure of Broad-Band Multilayer Antireflctive Coatins for Optical and Optoelectronic Devices," May 1998, Journal of Lightwave Technology, 16(5): 884-891.

"Rugate Filters for the Near Infrared and Visible Spectral Regions," Dec. 2003, retrieved from www.rugate.faumhofer.de, 2 main pages and 3 figure pages.

"Innovative Technologies for Optical Filters: Filter Rugate," Jul. 20, 2004, retrieved from www.innovations-report.de/html/berichte/verfahrenstechnologie/berichte-31447.html, web document, German language (1p) English machine translation (1p).

Stenzel et al., "Rugate Filters for the Near Infrared and Visible Spectral Regions," 2003, Fraunhofer Institute Annual Report 2003, pp. 38-41, German language on pp. 38 and 40, English language on pp. 39 and 41).

Schulz et al., "AR-hard®—Coating with Adjustable Spectral Bandwidth for Plastic Optics," 2003.

Rong et al., "A Continuous-wave Raman Silicon Laser," Feb. 17, 2005, Nature, vol. 433, pp. 725-728.

Rong et al., "An All-Silicon Raman Laser," Jan. 20, 2005, Nature, vol. 433, pp. 292-294.

Faist, Jerome, "Silicon Shines On," Feb. 17, 2005, Nature, vol. 433, pp. 691-692.

Koehl et al., "Continuous Silicon Laser, Intel Researchers Create the First Continuous Silicon Laser Based on the Raman Effect Using Standard CMOS Technology," 2005, White Paper, www.Intel.com, 6 pp.

Paniccia et al., "Intel's Research in Silicon Photonics Could Bring High-Speed Optical Communications to Silicon," Feb. 2004, White Paper, www.Intel.com, 6 pp.

Salib et al., "Silicon Photonics," May 10, 2004, Intel Technology Journal, vol. 8, Issue 2, pp. 143-160.

Paniccia et al., "Introducing Intel's Advances in Silicon Photonics," Feb. 2004, White Paper, accessed at http://www.intel.com/content/dam/www/public/us/en/documents/intel-research/Intel_Advances_Silicon_Photonics.pdf, 5 pp.

Paniccia et al., "Intel Unveils Silicon Photonics Breakthrough: High-Speed Silicon Modulation," Feb./Mar. 2004, Technology@Intel_Magazine, accessed at http://www.onversity.net/load/optic_modu.pdf, 6pp.

* cited by examiner

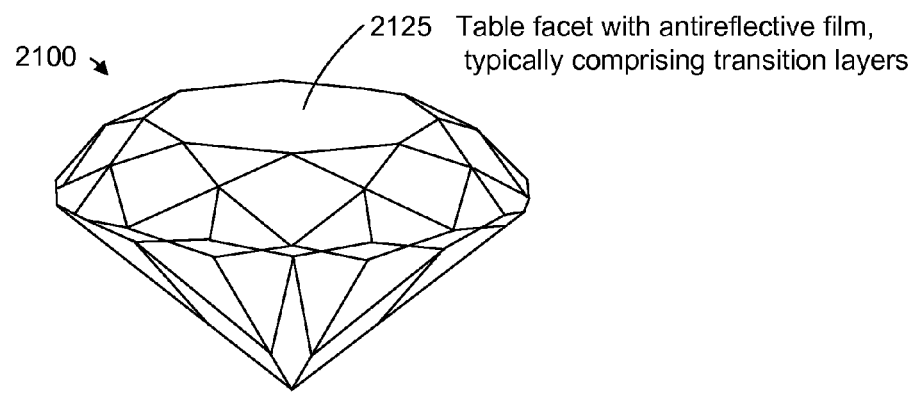
*Fig. 21A*
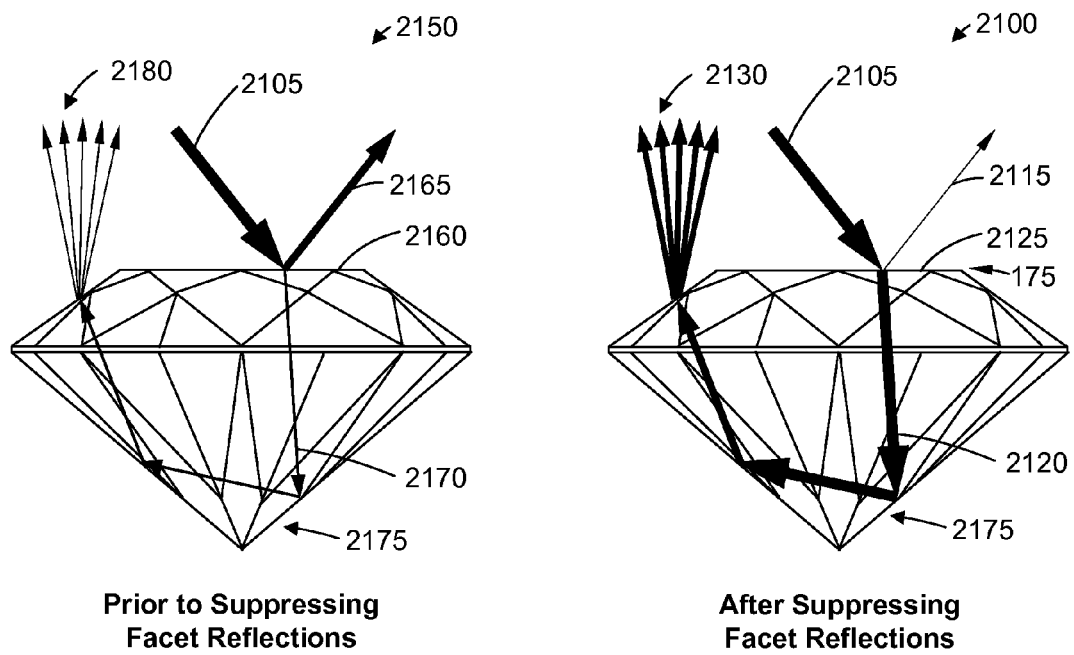
Prior to Suppressing
Facet Reflections
After Suppressing
Facet Reflections
*Fig. 21B*  *Fig. 21C*

METHOD AND SYSTEM FOR MANAGING LIGHT AT AN OPTICAL INTERFACE

CROSS REFERENCE TO RELATED APPLICATION

This application is a continuation of and claims priority to U.S. patent application Ser. No. 12/931,191 filed on Jan. 26, 2011 in the name of Michael L. Wach and entitled "Method and System for Managing Light at an Optical Interface" (U.S. Pat. No. 8,116,003, issue date Feb. 14, 2012); which is a continuation of and claims priority to U.S. patent application Ser. No. 11/825,614, entitled "Method and System for Managing Light at an Optical Interface," filed on Jul. 7, 2007 in the name of Michael L. Wach, (now U.S. Pat. No. 7,903,338); which claims priority to U.S. Provisional Patent Application No. 60/819,552, filed Jul. 8, 2006 in the name of Michael L. Wach and entitled "Method and System for Managing Light at an Optical Interface." The present application claims priority to each of the above identified patent applications. The entire contents of each of the above identified priority documents (including U.S. patent application Ser. Nos. 12/931, 191 and 11/825,614 and U.S. Provisional Patent Application No. 60/819,552) are hereby incorporated herein by reference.

TECHNICAL FIELD

The present invention relates to optical devices and more specifically to thin film optical systems that manage light at an interface between two optical materials that have distinct compositions or different refractive indices.

BACKGROUND

Thin films are useful for a wide range of optical applications, such as antireflective ("AR") coatings, high-reflective ("HR") coatings, dielectric mirrors, thin film interference filters, active light emitters, gratings, and color generators, to name a few examples. Compact size and environmental stability are two properties of optical thin films that encourage their deployment in modern applications including optical communications, lighting, vision, instrumentation, medical devices, computer monitors, display systems, etc. Certain types of optical thin films manipulate light by interference, which entails an additive or subtractive process in which the amplitudes of two or more overlapping light waves systematically attenuate or reinforce one another. Interference can produce polarization, wavelength-selective transmission and/or reflection, beam splitting, or various other effects on a light beam, according to the design of the thin film and its interaction with adjacent elements in an environment of an optical system.

Thin film interference filters typically comprise a stack of thin film layers or a plurality of laminates that collaboratively provide a band, span, or range of color transmission and another band, span, or range of color reflection. Such thin film interference filters often provide a pass band that is bracketed by two bands of reflection. That is, a spectral or color region of high transmission (and low reflectivity) lies between two spectral or color regions of low transmission (and high reflectivity). Many conventional interference filters are better suited to providing a pass band or a narrow spectral band of high transparency than to providing a stop band or a narrow spectral band of high reflectivity, sometimes referred to as a notch.

FIG. 3A illustrates a cross sectional view of a portion 325 of a conventional thin film apparatus, for example a band pass filter, comprising a first layer of optical material 360 adhering or laminated to a second layer of optical material 370. The accompanying FIG. 3B graphically depicts a representative refractive index profile 300 for the materials 360, 370 illustrated in FIG. 3B.

The optical materials 360, 370 typically have different refractive indices 310, 320, for example one being relatively high and one being relatively low. The material 370 might be silicon dioxide ($SiO_2$), of relatively low refractive index 320, while the material 360 might be tantalum pentoxide ($Ta_2O_5$), of relatively high refractive index 310. In the conventional approach, each material layer 360, 370 typically has a thickness at least on the order of one-fourth of the wavelength of the light that the system 325 handles.

The interface 340 lies between two materials 360, 370, with FIG. 3 illustrating two more interfaces 330, 350. As shown in FIG. 3B, the refractive index typically changes abruptly at the boundaries or interfaces 330, 340, 350 between each layer of the material 360 and the material 370. Thus, the system 325 typically has a crisp change in the material composition between the two material regions 360, 370.

The refractive index change between the two materials 360, 370, at the interface 340, can usefully induce a light reflection that, when combined with reflections from other interfaces 330, 350, produces optical interference. However in some applications, a more gradually change in refractive index at the interfaces 330, 340, 350 would be desirable. For example, thin film notch filters that produce a narrow spectral band of reflection between two spectral regions of transmission may benefit from having gradual changes in refractive index at layer boundaries.

A class of notch filters known as "rugate" filters typically use a conventional approach to providing a gradual refractive index change at a filter's thin film layer interfaces. In a rugate filter, each interface between adjoining thin film layers typically comprises a blended combination of the materials of the two adjoining layers. That is, if the apparatus 325 illustrated in FIG. 3A was a rugate filter, the interface 340 would have a composition that gradually changed between the material 370 and the material 360 (along the Z axis).

Rugate filters are typically fabricated in a vacuum chamber via thin film deposition. A source in the chamber outputs particles of high-refractive index material that accumulate to create the high-refractive index layers. Another source outputs particles of low-refractive index materials to create the adjoining low-refractive index layers. When forming the rugate's blended interface, both the high-refractive index source and the low-refractive index source may actively output their respective materials. After forming the major portion of the high-refractive index layer, the high-refractive index source gradually reduces its rate of outputting high-refractive index particles. As the deposition rate of high-refractive index particles decreases, the low-refractive index source begins outputting low-refractive index particles and gradually increases the deposition rate of low-refractive index particles. Accordingly, the rugate's blended interface can be formed by simultaneously depositing high- and low-index materials at controlled deposition rates.

However, with conventional technologies, providing a sufficient level of control of the deposition rates can be difficult. If the relative deposition rates of the high- and low-index materials are not precisely controlled, the rugate's blended layer interfaces may fail to provide the desired optical properties. Another problem with many conventional techniques for producing rugate filters can occur with the material properties that result from the blended composition itself. Two materials that are individually well suited to forming pure layers may not be compatible with one another when mixed. That is, although two pure material layers may adhere to one another, those two materials may not form a stable or robust structure when blended or when mixed at the atomic, molecular, or particulate level. For example, the blended composition may have thermal expansion properties or sensitivities that are less desirable than the corresponding properties of unblended layers. Further, processing the appropriate materials in a manner that facilitates successful blending can be problematic.

To address these representative deficiencies in the art, what is needed is an improved capability for managing light propagating near an interface between two optical materials or media. A further need exists for a structure that can provide a smooth or gradual refractive index transition between two materials. Yet another need exists for a system that can provide a smooth material transition at an interface between two sections of distinct optical materials. Still another need exists for an efficient or robust process to fabricate thin film devices in a manner that provides desirable interfaces between adjoining film layers. One more need exists for a notch filter that offers a high level of optical performance, that provides a low level of environmental and/or thermal sensitivity, and that can be cost-effectively manufactured. Finally, a need exists for a process of forming filters with rugate-type optical characteristics without necessarily blending optical materials in a deposition chamber. A technology filling one or more of these needs would enhance the precision with which optical thin films manipulate light and would facilitate cost-effective utilization of optical thin films in numerous applications.

SUMMARY

The present invention can support managing light in the vicinity of an interface or a junction between two optical materials that have distinct material compositions or optical characteristics, such as different refractive indices.

In one aspect of the present invention, an optical system that comprises thin film layers can have a composition and/or an optical property that varies systemically along a direction that is perpendicular to the layers (or essentially parallel to layer thickness). The optical system can comprise multiple thin film layers disposed to form a stack, a plurality of adjoining or abutting layers, a laminate structure, or some other ordered arrangement. Such a stack can comprise thin film layers that have a first material composition interleaved or interspersed between thin film layers that have a second material composition. For example, with the possible exception of the layers at each end of the stack, each layer of the first material can be sandwiched between two layers of the second material. Likewise and with the same potential exception, each layer of the second material can be sandwiched between two layers of the first material. Taken individually, each layer can have a uniform or essentially homogeneous composition. Meanwhile, the stack can have a net or an aggregate composition that varies from one end of the stack to the other end of the stack. That is, while the stack can comprise two or more sets of thin film layers, each having an essentially common composition, the stack as a whole can have a composition that progressively changes between each end of the stack. The aggregate compositional variation can impart the stack with a corresponding optical variation, such as a graduated refractive index. The end-to-end compositional variation can result from the configuration or arrangement of the individual layers of the stack. For example, varying the thicknesses of the individual layers can produce a defined compositional pattern. The compositional variation might alternatively result from progressively increasing the number of layers of one material type towards one end of the stack.

A system that manages light near an interface between two optically dissimilar materials can have numerous applications. To name a few potential applications, the system can benefit thin film interference filters, notch filters, band pass filters, dielectric filters, ripple or sidebands in light manipulation devices, dispersion characteristics, flat panel displays, antireflective coatings, optoelectronics devices, electro-optic materials, silicon photonic devices, gem stones, jewelry, charge coupled devices ("CCDs"), CCD pixels, laser cavities, optical gain media, optical detectors, optical receivers that respond to changes in light intensity in advance of the light reaching the receiver, surgical lasing systems that apply dye to tissue to enhance interaction between the laser light and the tissue, tissue analyzers that reference out the effect of blood on the tissue analysis by modulating blood flow during analysis, diffractive mode expanders, planar lightguide circuits, optical fibers, lenses, optical properties of diamonds, analytical systems that characterize samples via analyzing light-matter interactions, monofilament lines that have improved optical characteristics, etc.

The discussion of optical thin films presented in this summary is for illustrative purposes only. Various aspects of the present invention may be more clearly understood and appreciated from a review of the following detailed description of the disclosed embodiments and by reference to the drawings and any claims that may follow. Moreover, other aspects, systems, methods, features, advantages, and objects of the present invention will become apparent to one with skill in the art upon examination of the following drawings and detailed description. It is intended that all such aspects, systems, methods, features, advantages, and objects are to be included within this description, are to be within the scope of the present invention, and are to be protected by the accompanying claims.

BRIEF DESCRIPTION OF THE DRAWINGS

FIG. 1, illustrate an optical system comprising an optical thin film adhering to a substrate in accordance with an exemplary embodiment of the present invention.

FIG. 20, illustrate a flowchart of a process for adjusting an optical detector, based on an intensity of an optical signal, in advance of the detector receiving the optical signal in accordance with an exemplary embodiment of the present invention.

FIGS. 21A, 21B, and 21C, collectively FIG. 21, illustrate a gemstone prior to and after applying an optical coating to a facet, wherein the coating suppresses facet reflection in accordance with an exemplary embodiment of the present invention.

FIG. 27, illustrate a flowchart of a process for analyzing tissue of an organism via acquiring spectra from the tissue while modulating the tissue's blood content and using the acquired spectra to compensate for blood content in accordance with an exemplary embodiment of the present invention.

Figure 1A:
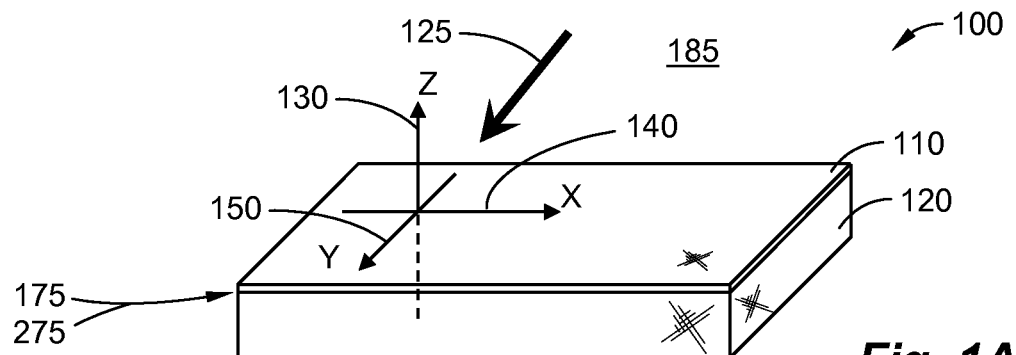
FIGS. 1A and 1B, collectively

Many aspects of the invention can be better understood with reference to the above drawings. The components in the drawings are not necessarily to scale, emphasis instead being placed upon clearly illustrating the principles of exemplary embodiments of the present invention. Moreover, in the drawings, reference numerals designate like or corresponding, but not necessarily identical, elements throughout the several views.

DETAILED DESCRIPTION OF EXEMPLARY EMBODIMENTS

Exemplary embodiments of the present invention can involve managing light at an interface or a juncture between two optical materials, for example to promote reflection, transmission, or transfer of light at the interface. Various applications and system can benefit from managing light at an optical interface.

Figure 15:
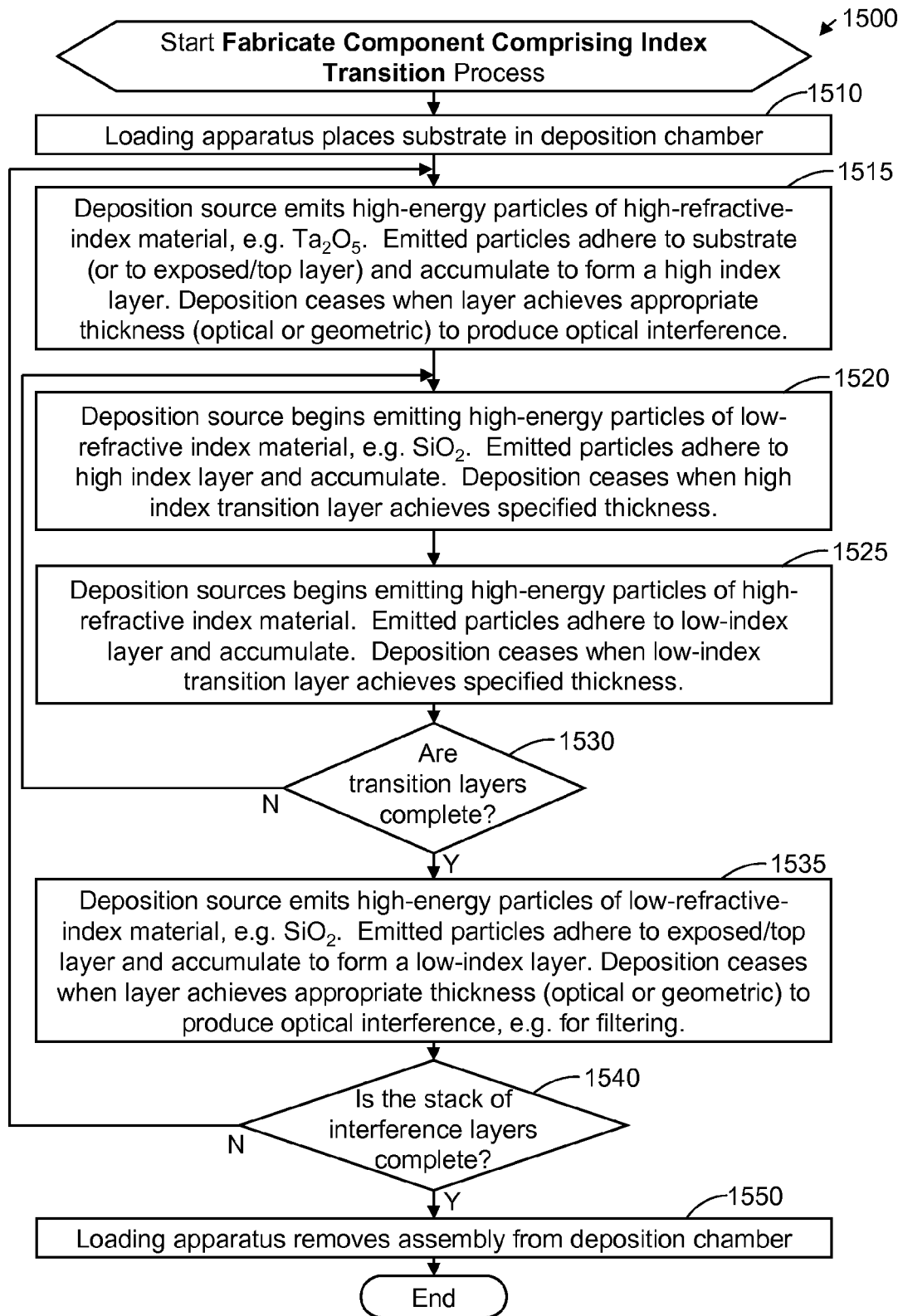
FIG. 15 illustrates a flowchart of a process for fabricating optical components that comprise a series of thin film layers that manage light at an interface between two optical material sections in accordance with an exemplary embodiment of the present invention.
Figure 16:
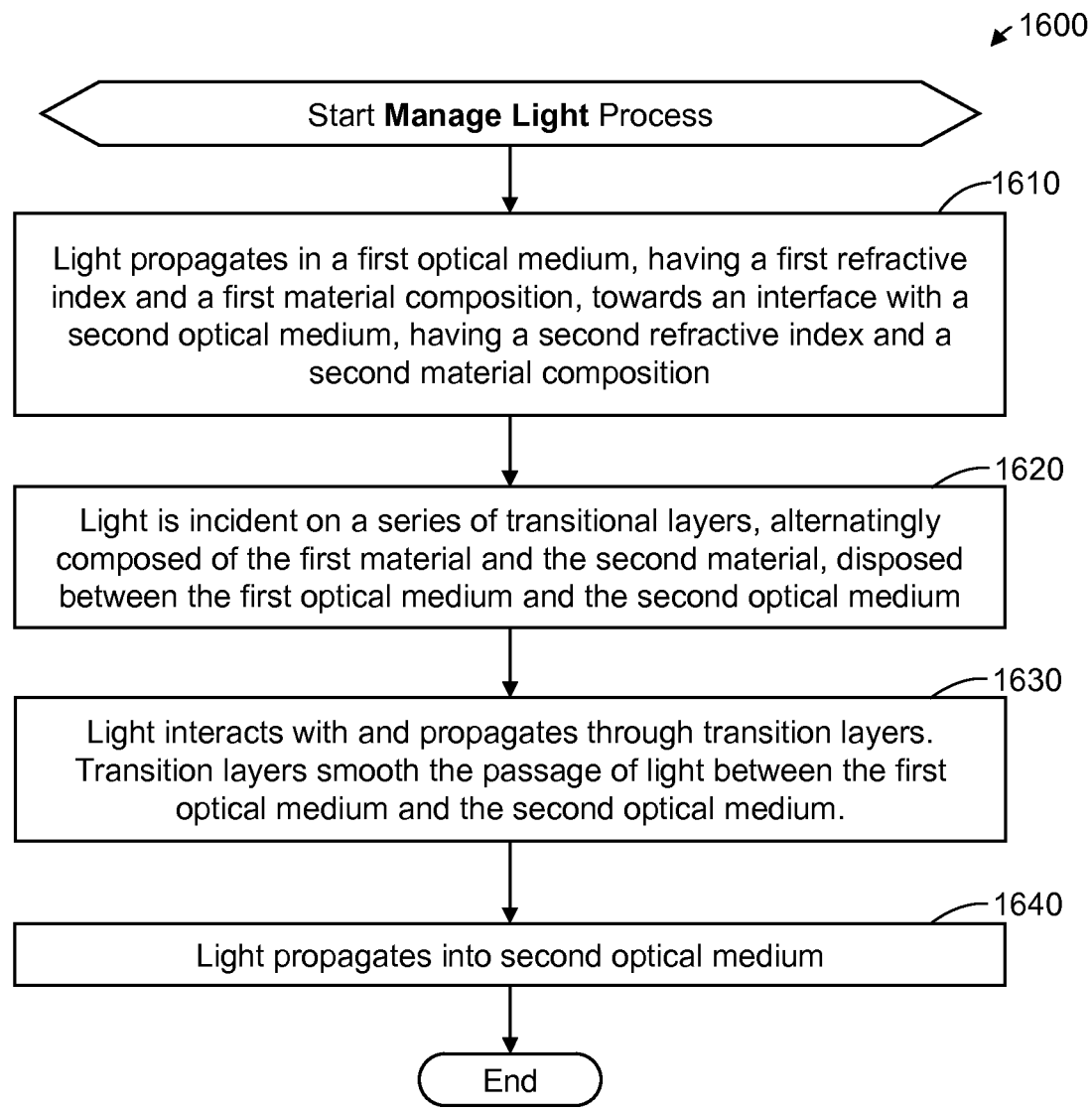
FIG. 16 illustrates a flowchart of a process for using a series of thin film layers to manage light at an interface between two optical material sections in accordance with an exemplary embodiment of the present invention.

A method and system for managing light at a material interface and certain application examples will now be described more fully hereinafter with reference to FIGS. 1, 2, and 4-27, which show representative embodiments of the present invention. FIGS. 1 and 2 depict thin film systems that adhere to substrates and that can comprise a thin film structure for managing light at an optical interface. FIGS. 4-9 provide graphical refractive index profiles of thin film systems that manage light at an optical interface. FIGS. 10-14 provide illustrations of thin film systems that manage light at an optical interface. FIGS. 15 and 16 provide flow diagrams of methods for making and operating thin film systems that manage light at an optical interface.

Figure 22:
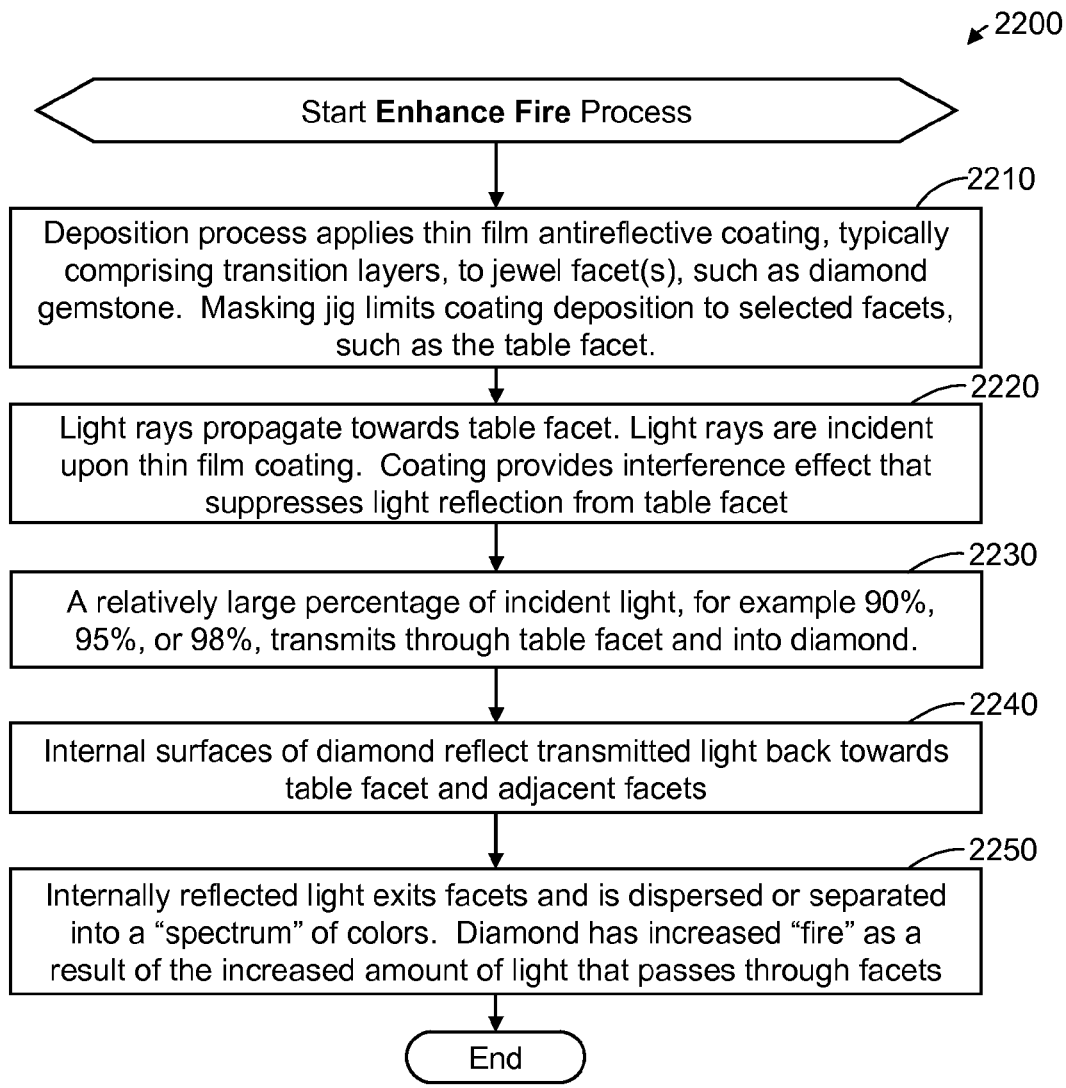
FIG. 22 illustrates a flowchart of a process for using a thin film coating to suppress reflections from a facet of a gemstone and to enhance the gemstone's fire in accordance with an exemplary embodiment of the present invention.
Figure 23:
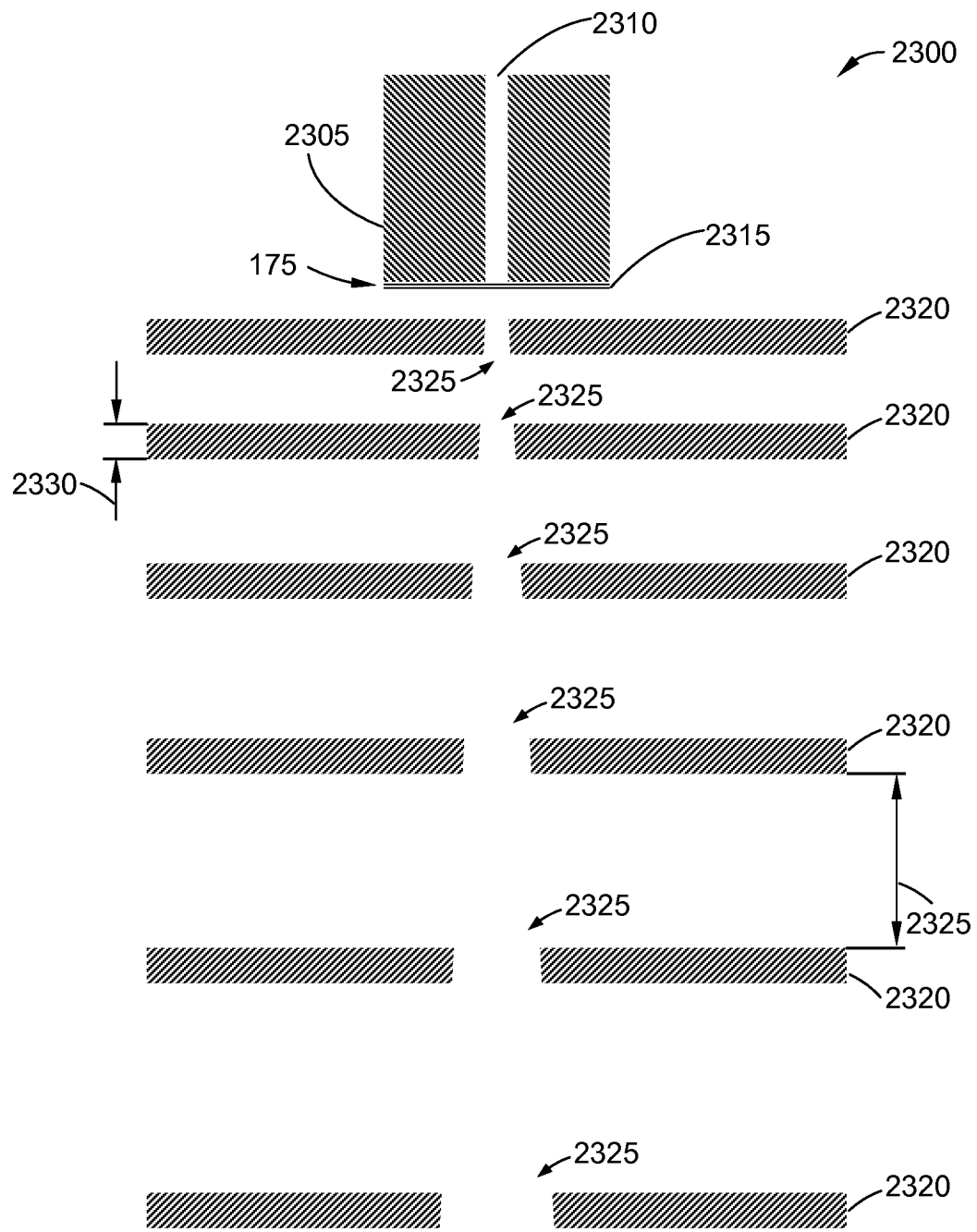
FIG. 23 illustrates a system, comprising a series of apertures, having progressively increasing diameter, that perform a mode expansion on light emitted from an optical fiber in accordance with an exemplary embodiment of the present invention.
Figure 24:
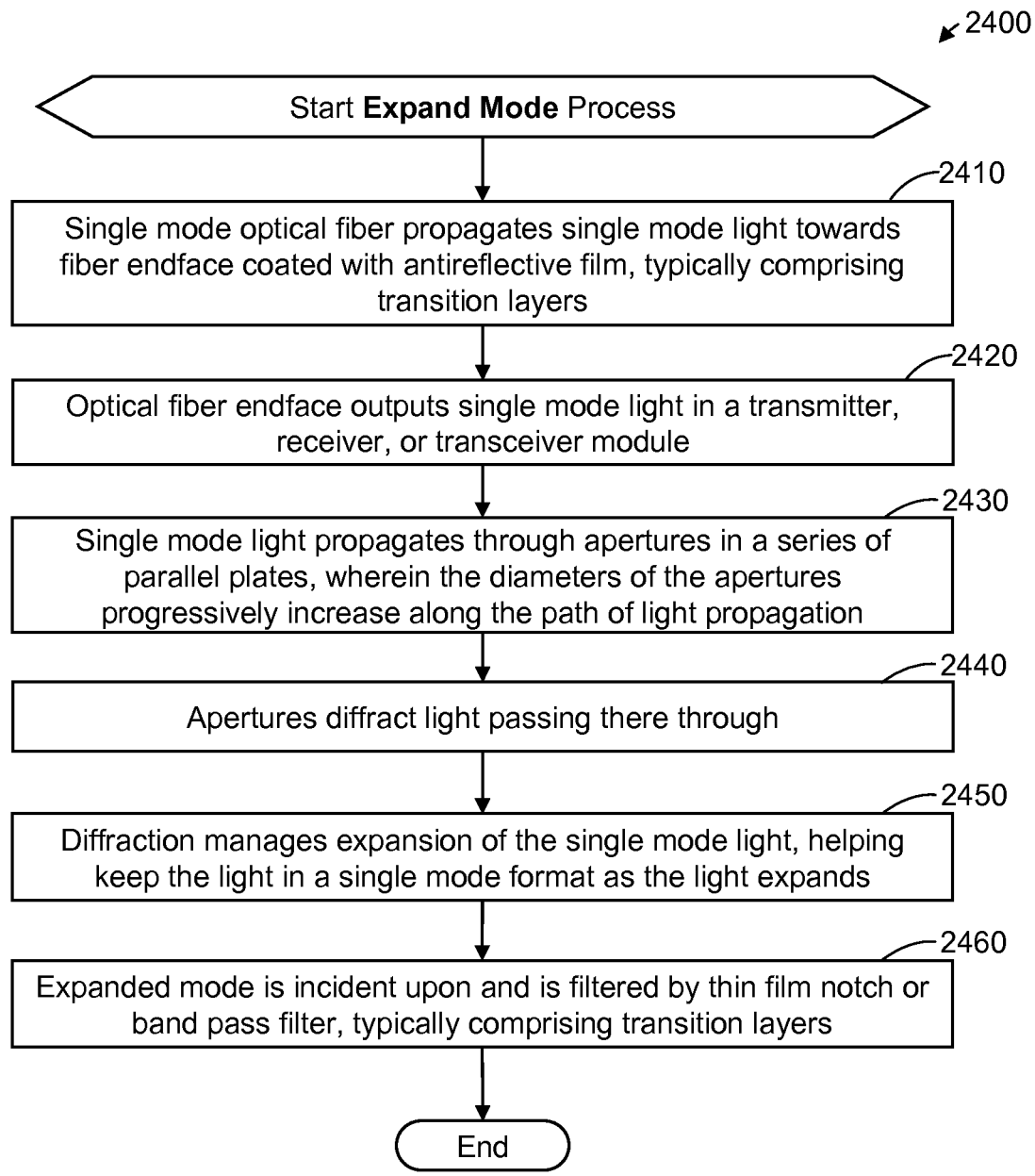
FIG. 24 illustrates a flowchart of a process for expanding a single mode light beam using diffraction associated with a series of progressively larger apertures in accordance with an exemplary embodiment of the present invention.
Figure 25:
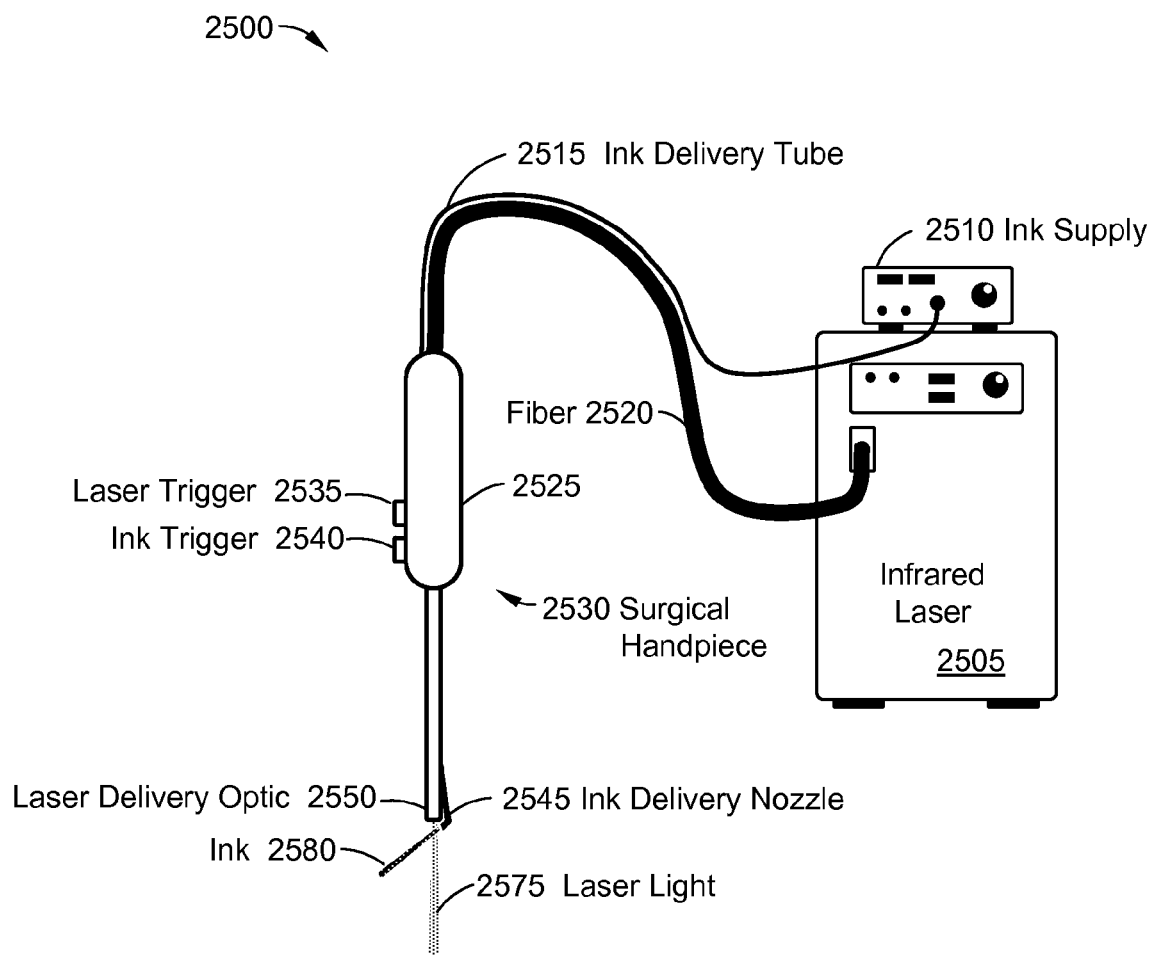
FIG. 25 illustrates a surgical system for cutting biological tissue by applying a light absorber and laser light to the tissue in accordance with an exemplary embodiment of the present invention.
Figure 26:
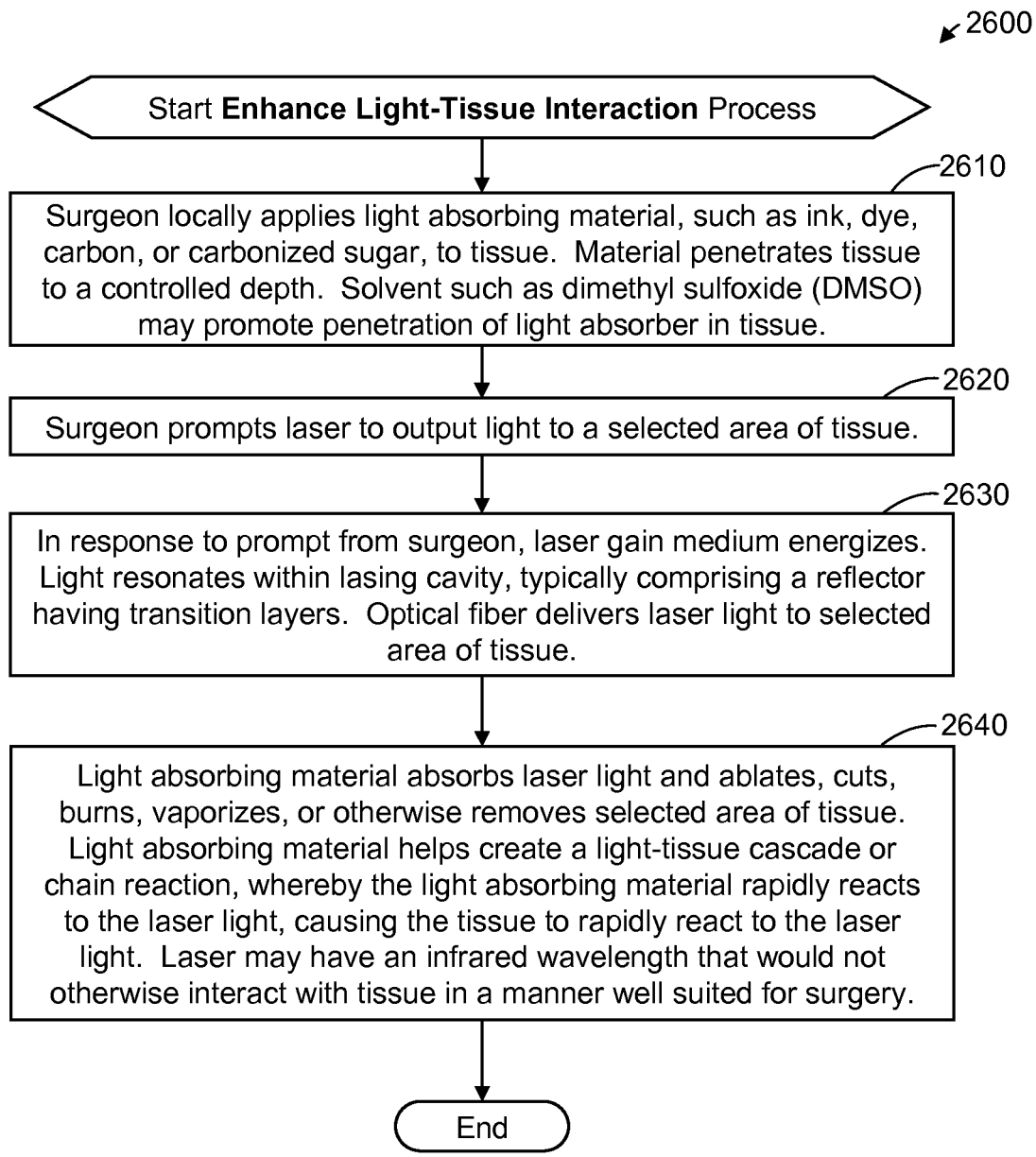
FIG. 26 illustrates a flowchart of a process for cutting biological tissue by applying dye and laser light to the tissue in accordance with an exemplary embodiment of the present invention.
Figure 27A:
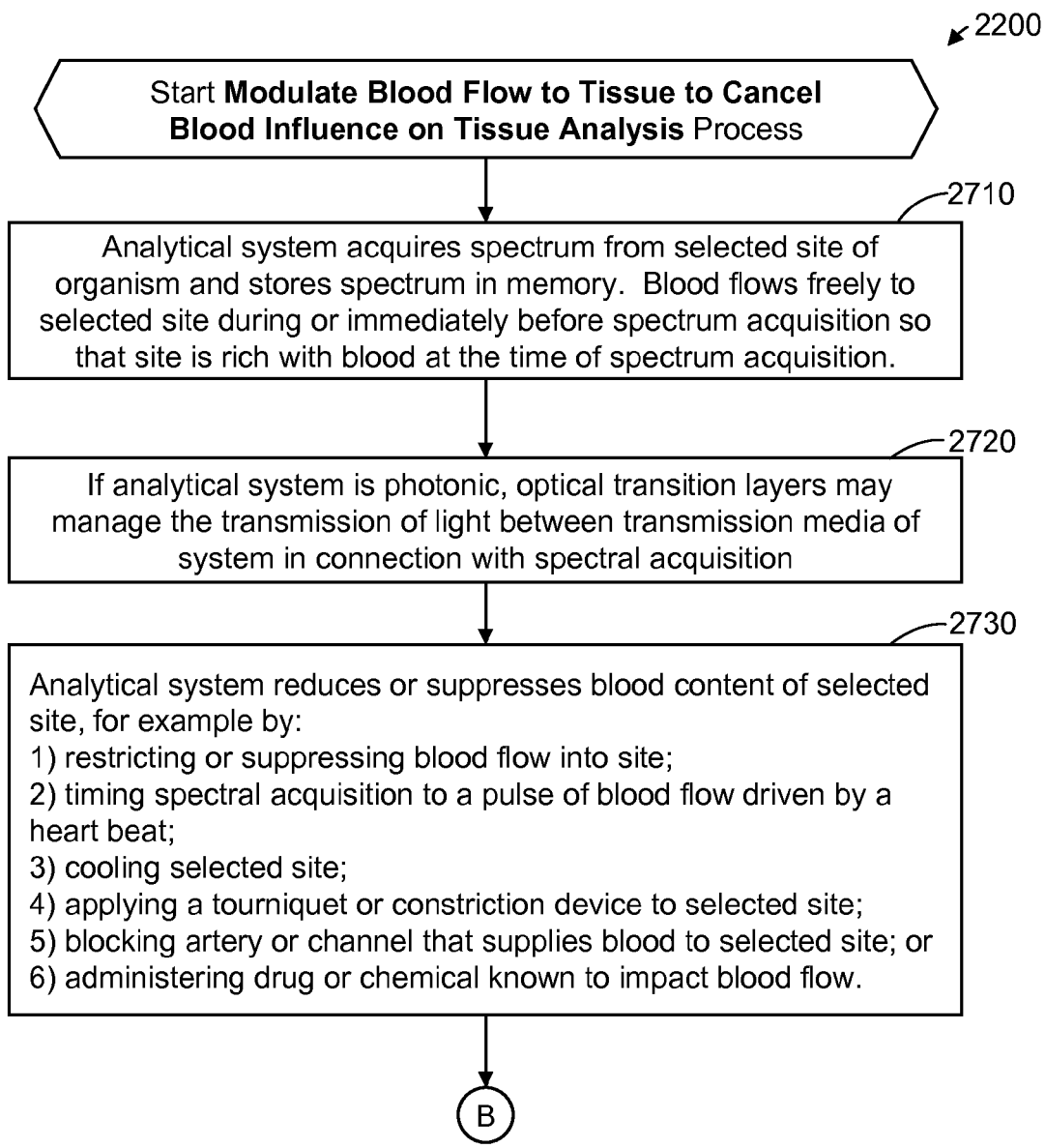
FIGS. 27A and 27B, collectively
Figure 27B:
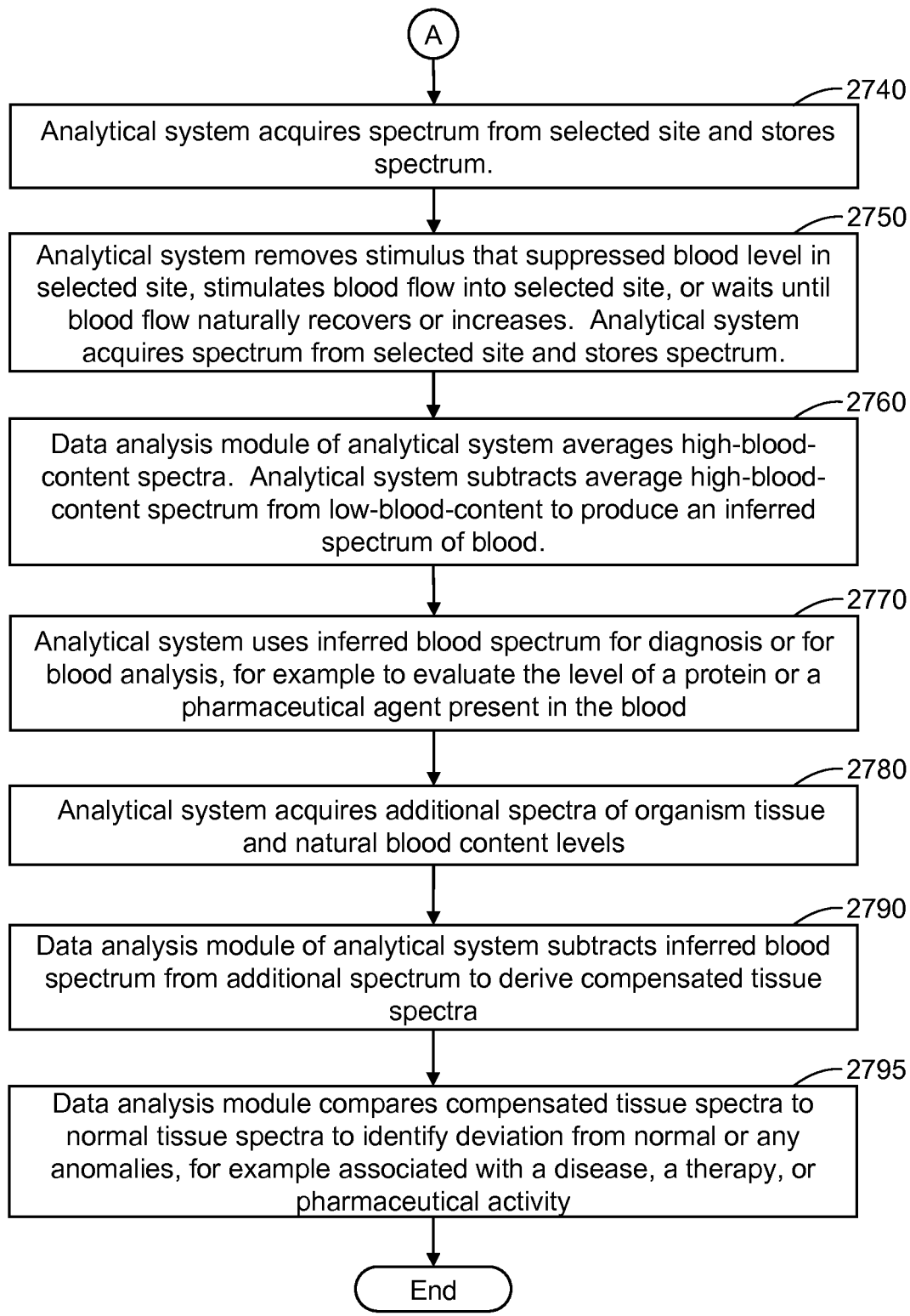
Figure 28:
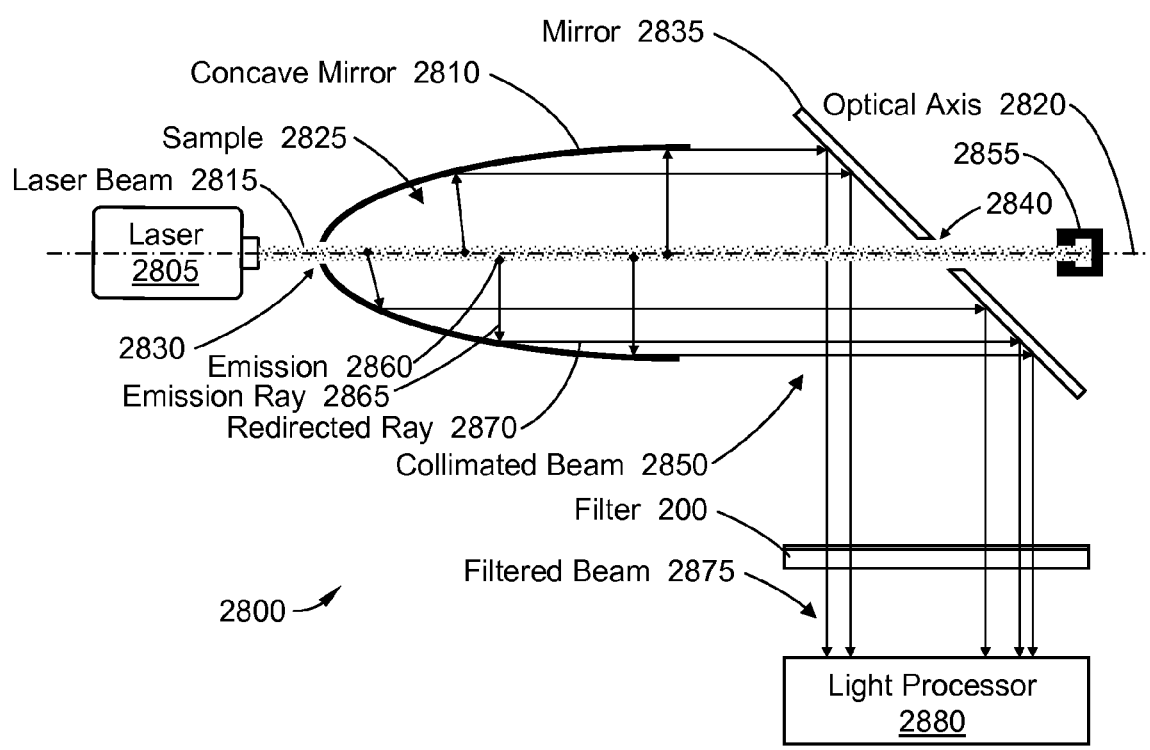
FIG. 28 illustrates an optical system for optically characterizing a sample in accordance with an exemplary embodiment of the present invention.
Figure 29:
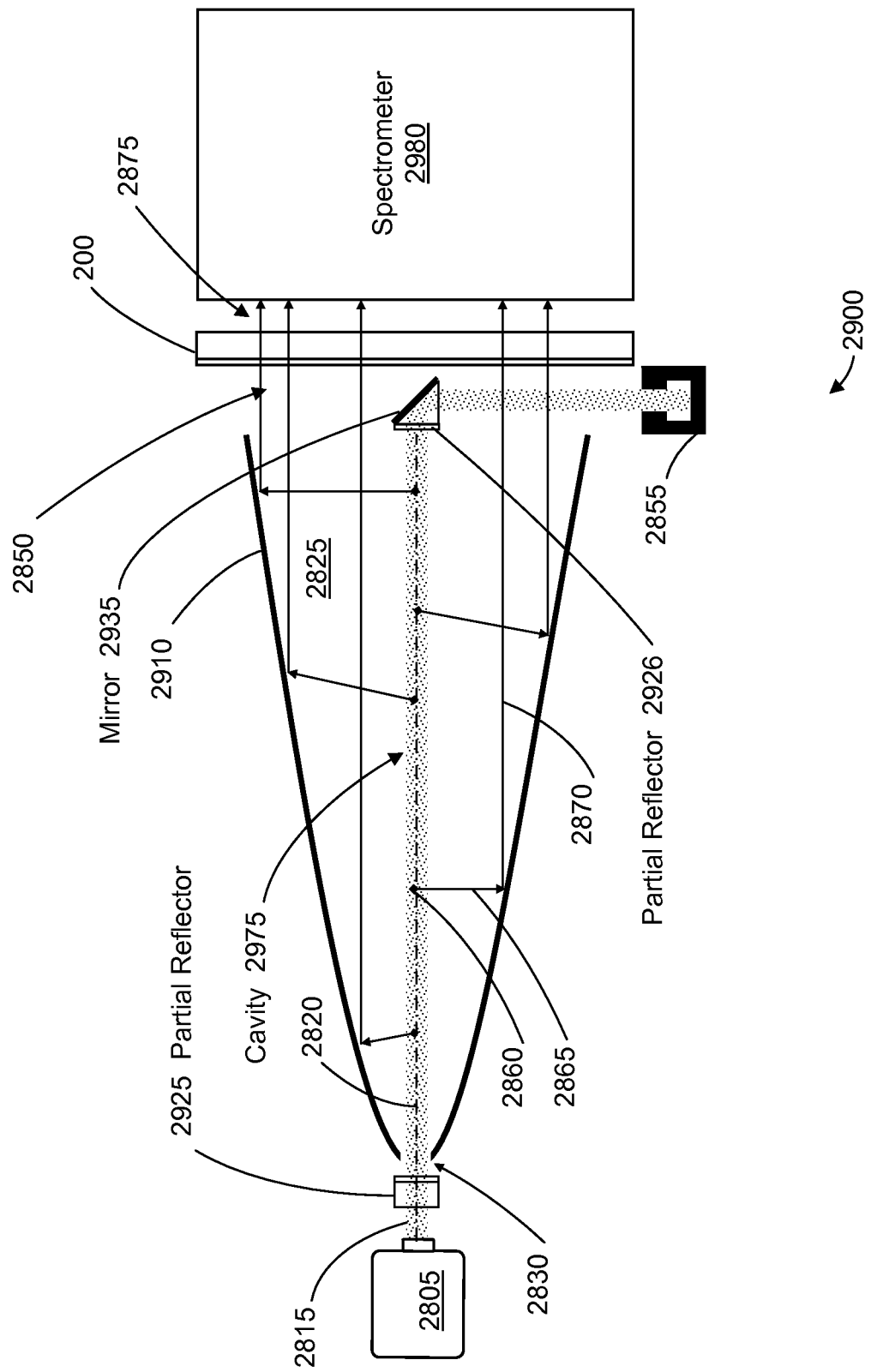
FIG. 29 illustrates an optical system for optically characterizing a sample in accordance with an exemplary embodiment of the present invention.

FIGS. 17-29 describe methods and systems that may involve a thin film system managing light at an optical interface. FIGS. 17-20 relate to an optical receiver that can prepare itself to receive an optical signal in advance of receiving the optical signal. FIGS. 21-22 relate to treating a gemstone to enhance the manner in which the gemstone disperses incident light into a spectrum of colors. FIGS. 23 and 24 relate to expanding a light beam using a series of progressively larger apertures that provide controlled diffraction. FIGS. 25-26 relate to applying a local surface treatment to a biological tissue to enhance the interaction between a surgical laser and the tissue. FIG. 27 relates to modulating the blood content of a tissue volume of an organism to facilitate conducting an analysis of the tissue and/or the blood. FIGS. 28 and 29 relate to using light for material analysis.

The invention can be embodied in many different forms and should not be construed as limited to the embodiments set forth herein; rather, these embodiments are provided so that this disclosure will be thorough and complete, and will fully convey the scope of the invention to those having ordinary skill in the art. Furthermore, all "examples" or "exemplary embodiments" given herein are intended to be non-limiting, and among others supported by representations of the present invention.

Turning now to discuss each of the drawings presented in FIGS. 1-29, in which like numerals indicate like elements through the several figures, an exemplary embodiment of the present invention will be described in detail.

Figure 1B:
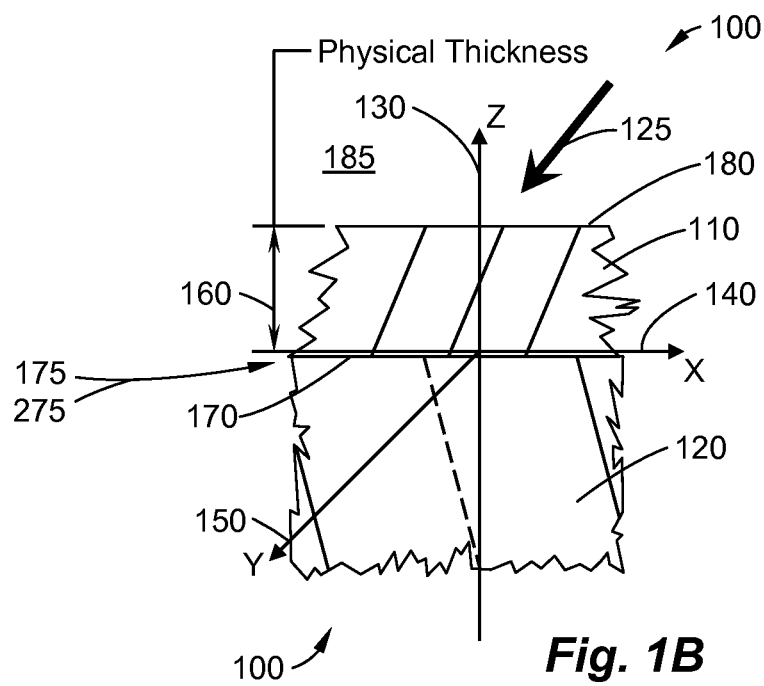
Figure 2:
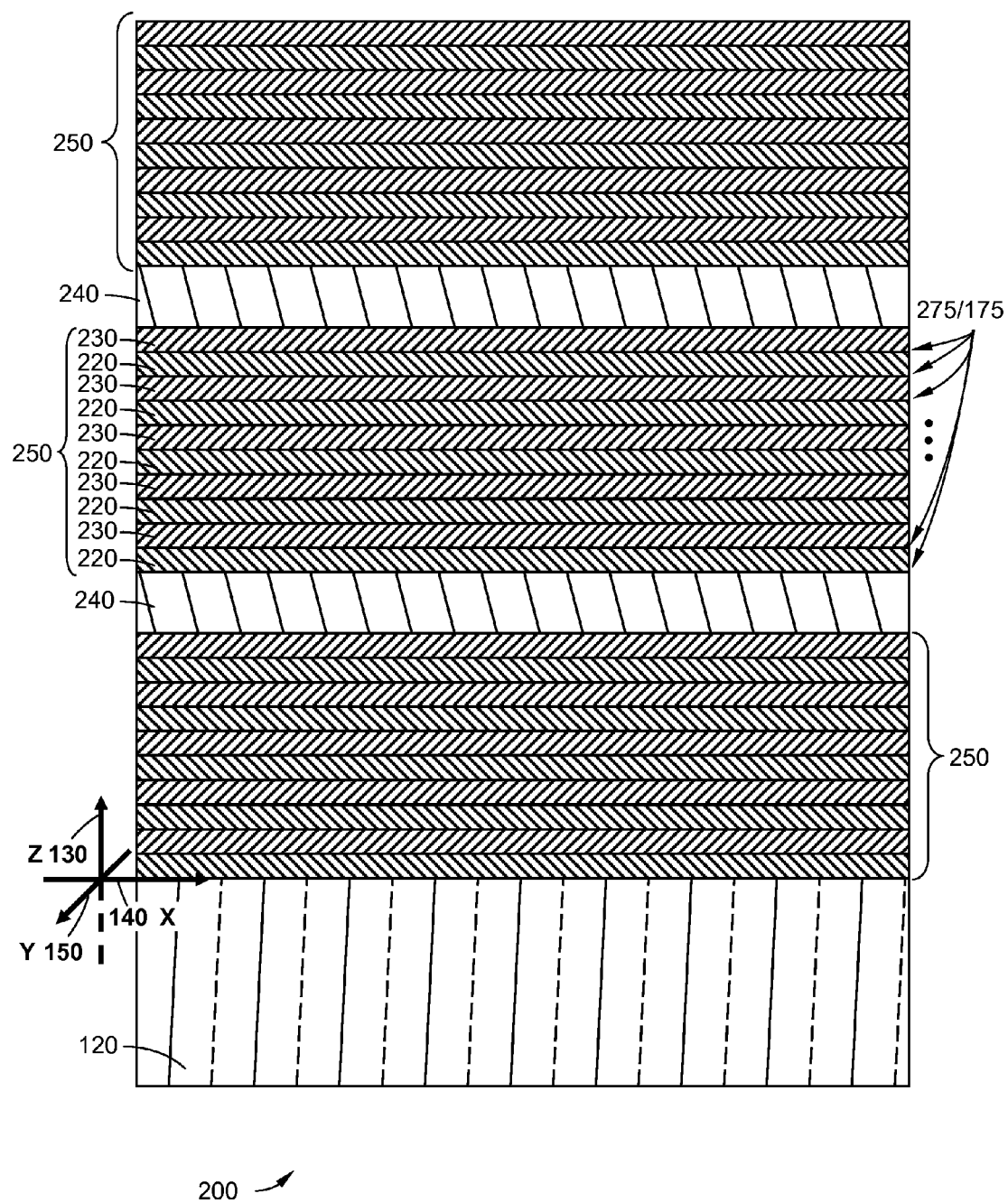
FIG. 2 illustrates a stack of optical thin films on a substrate in accordance with an exemplary embodiment of the present invention.

FIGS. 1A and 1B illustrate an exemplary thin film optical system 100 comprising an optical thin film 110 adhering to a substrate 120 according to an embodiment of the present invention. A Cartesian coordinate system, having an x-axis 140, a y-axis 150, and a z-axis 130, illustrates the relative orientation of the optical thin film 110 and substrate 120 in the optical system 110. The x-axis 140 and the y-axis 150 are parallel to the major surfaces 170, 180 of the optical thin film 110, while the z-axis 130 traverses the thickness 160 of the optical thin film 110. Those major surfaces 170, 180, whether planar or contoured in a non-planar form, can be referred to as faces of the optical thin film 110. That is, the z-axis 130 is perpendicular to the planar interface 170 between the optical thin film 110 and the substrate 120, while the x-axis 140 and the y-axis 150 lie in or along the plane of this interface 170.

The exemplary substrate 120 comprises a volume of optical material taking the general form of a slab with a smooth planar surface 170 to which the optical thin film 110 adheres. In this configuration, the substrate 120 provides mechanical support and physical stability for the optical thin film 110. Although FIG. 1 illustrates the optical thin film 110 in a planar configuration, the optical thin film 110 can alternatively have a non-planar contour, for example conforming or adhering to a convex, cylindrical, or concave surface of a lens or some other passive or active device, in accordance with exemplary embodiments of the present invention.

Functionally, a refractive index differential at the surface interface boundary 170 between the material of the optical thin film 110 and the material of the substrate 120 induces reflection of the light 125 propagating through the thickness 160 of the optical thin film 110, generally along the z-axis 130. The outer surface 180 of the optical thin film 110, opposite the substrate interface 170, is also reflective to light 125 propagating through the thickness 160 of the optical thin film 110. The outer surface's reflectivity can arise from the refractive index differential between the material of the optical thin film 110 and the surrounding media 185. That is, the inner surface 170 and the outer surface 180 of the optical thin film 110 may individually reflect light 125 propagating through the thickness 160 of the optical thin film 110. The degree of reflectivity of each of these surfaces 170, 180 can be a function of the refractive index differential at or across each surface 170, 180 and the angle of the incident light 125 relative to the z-axis 130 and other potential factors, such as the polarization of the light 125. The light 125 propagating through the optical thin film 110 may travel parallel with the z-axis 130. Alternatively, the light 125 may be incident on the optical thin film 110 at an angle, such as an acute angle, with respect to the z-axis 130.

The system 110 can comprise a thin film structure that manages light 125 at the inner interface boundary 170 and/or the outer surface 180. That thin film structure can manage light flow, light passage, light reflection, phase shift, or some other interaction or aspect of the light 125 that is incident upon the inner and outer interfaces 110, 180. Moreover, the structure can provide an optical or material transition between refractive indices of the substrate 120 and the thin film 110 or between the refractive indices of the thin film 110 and the surrounding medium 185. In providing an optical or material transition, the thin film structure can effectively smooth the abrupt material and refractive index change of the interface 170 and the interface 180. Such a thin film structure can be referred to as transition layers or a transition device, but may nonetheless have an expanded operability beyond facilitating light transition. Thus, such a thin film structure can be viewed as transition layers that provide a useful influence over the light 125 that is incident on the optical interface 170 and/or the optical interface 180.

FIG. 1 does not illustrate the detailed structure of such transition layers but rather provides a somewhat macroscopic system-level view. However, the reference number "175" and the accompanying lead line shows one exemplary location for transition layers, specifically at the material interface 275.

As discussed in further detail below, the transition layers 175 can comprise a plurality of thin film layers that are significantly thinner than the layer 110. FIGS. 6-14, discussed below, describe various exemplary embodiments of the transition layers 175.

In one exemplary embodiment of the present invention, the thickness 160 of the optical thin film 110 is less than approximately ten wavelengths of the light 125 that the optical thin film 110 is operative to manipulate. In one exemplary embodiment of the present invention, the thickness 160 of the optical thin film 110 is less than approximately five wavelengths of the light 125 that the optical thin film 110 is operative to manipulate. In one exemplary embodiment, the thickness 160 is a physical thickness that can have a range of actual numerical values or may be less than approximately five times the wavelength of the light 125 that the optical thin film 110 manipulates with thin film interference.

In one exemplary embodiment of the present invention, the thickness 160 of the optical thin film 110 is less than approximately three wavelengths of the light 125 that the optical thin film 110 is operative to manipulate. In one exemplary embodiment of the present invention, the thickness 160 of the optical thin film 110 is less than approximately one wavelength of the light 125 that the optical thin film 110 is operative to manipulate. In one exemplary embodiment of the present invention, the thickness 160 of the optical thin film 110 is approximately one fourth the wavelength of the light 125 that the optical thin film 110 is operative to manipulate. In one exemplary embodiment of the present invention, the thickness 160 of the optical thin film 110 is greater than approximately one nanometer and less than approximately ten microns. In various embodiment, the thickness of the transition layers 175 can be one-fourth, one-tenth, one-fiftieth, one-hundredth, one-thousandth, or in a range thereof, of any of these thicknesses 160 of the thin film layer 110. In various exemplary embodiments, the thicknesses of the individual layers of the transition layers 175 can be one-fourth, one-tenth, one-fiftieth, one-hundredth, one-thousandth, or in a range thereof, of the total thickness of the transition layers 175.

In addition to a physical thickness 160, the optical thin film 110 can have an optical thickness that is a function of the refractive index of the material of the optical thin film 110 and the geometric or physical thickness 160. The refractive index, or index of refraction, of a material is the speed of light in a vacuum divided by the speed of light in the material. Since light propagates more slowly in ordinary materials than in a vacuum, the refractive index of an ordinary material is greater than one, often between about one and four. The optical thickness parameter is physical thickness 160 multiplied by refractive index. The optical thickness of a section of optical material, such as an optical thin film 110, is the material section's physical thickness 160 multiplied by the material section's refractive index. Since refractive index is greater than one for normal optical materials, a section of ordinary material typically has an optical thickness that is greater than its corresponding physical thickness 160.

The surrounding medium 185, which is in contact with the outer surface 180 of the optical thin film 110, can be a range of one or more gaseous, liquid, or solid materials. In one exemplary embodiment of the present invention, the medium 185 is space, essentially void of matter. That is, the thin film 110 can operate in a vacuum environment. In one exemplary embodiment of the present invention, the medium 185 is a gas, such as air, nitrogen, hydrogen, helium, oxygen, or a mixture of gases. In one exemplary embodiment of the present invention, the medium 185 is another optical thin film layer, such as a layer of a thin film interference filter. In one exemplary embodiment of the present invention, the optical thin film 110 adheres to this medium 185 as well as to the substrate 120. In one exemplary embodiment of the present invention, this medium 185 is a liquid such as water, optical matching gel, matching fluid, a biological fluid, or hydrocarbon. Such biological fluids can include blood, saliva, cerebral spinal fluid ("CSF"), secretions, urine, or milk, any of which can be either in a processed or a natural form. The medium 185 can also be glass, a plastic, a rubber, a composite, an inhomogeneous matrix, a resin, or an epoxy, any of which can be in a solid or viscous state. In one exemplary embodiment, the system 100 is encapsulated in plastic, for example via molding, with the plastic being the medium 185. In addition to passive materials, the medium 185 can be an active material such as a semiconductor detector, optically active material, electrically active material, optical gain medium, or a silicon photonic material, for example. The medium 185 can also be a biological composition such as a matrix of cells, tissue, tumorous material, muscular tissue, for example. In general, the medium 185 is not limited to a specific material, or any of the materials or compositions discussed herein.

In one exemplary embodiment of the present invention, the medium 185 is sealed in a hermetic environment. The medium 185 can be the hermetic internal environment of an electronic, optical, or optoelectronic package, for example a receiver, transmitter, or receiver module for optical networking. In one exemplary embodiment of the present invention, the medium 185 resides in a sealed environment that is not hermetic, such as in a water-tight enclosure that is permeable to gaseous contamination.

In one exemplary embodiment, the system 100 comprises a thin film interference filter with the encapsulated in plastic, with the plastic encapsulating material comprising the medium 185. Transition layers (or an antireflective film) located adjacent the surface 180 can help manage the flow of light between the filter and the encapsulating material. The structure comprising the plastic and the filter can be deployed in a transmitter, a receiver, or a transceiver for an optical networking application, such as fiber-to-the-home.

The refractive indices of the medium 185, the optical thin film 110, the substrate 120, the transition layers 175, and/or the individuals layers of the transition layers 175, can shift temporarily in response to an environmental change such as stress or operating temperature. Alternatively, these refractive indices can remain stable, experiencing little change in response to environment effects. In one exemplary embodiment of the present invention, one or more of these refractive indices can intentionally respond to a control input, which can be, without limitation, an electrical, magnetic, optical, or electromagnetic field, signal, or wave.

Light interference can result from additive or subtractive interaction between reflection at the outer surface 180 of the optical thin film 110 and reflection at the inner surface 170 of the optical thin film 110. When these two reflections are in phase with one another, the amplitudes constructively add. Alternatively, when the reflections are out of phase with respect to one another, the amplitudes can destructively subtract or cancel one another. Such constructive and destructive interference can provide a wide assortment of optical effects. Exemplary effects include filtering, polarizing, and dispersing light, among others.

The transition layers 175 can provide an heightened level of control or management over the light interference associated with those surfaces 170, 180. In one exemplary embodiment, the transition layers 175 can suppress the interference. In one exemplary embodiment, the transition layers 175 can enhance or amplify the interference. In one exemplary embodiment, the transition layers 175 can impart the interference with increased selectivity in terms of wavelength, frequency, or color. That is, the transition layers 175 can provide precise wavelength, frequency, or color control over light interference that typically occurs in optical thin film systems.

In one exemplary embodiment of the present invention, an operability of the optical thin film 110 to manipulate light 125 by thin film interference is a function of or is related to one or more of: the thickness 160 of the optical thin film 110 in relation to the wavelengths of manipulated light 125; the spatial relationship or physical separation between the outer surface 180 and the inner surface 170; the refractive indices of the substrate 120, the optical thin film 110, and the surrounding medium 185; the angle of the light 125 with respect to the z-axis 130; the polarization of the light 125; and the transition layers 175.

In one exemplary embodiment of the present invention, interference of the optical thin film 110 provides selective transmission light having specific wavelengths and reflection of the light that is not transmitted. The transition layers 175 can enhance, control, or otherwise manage such interference, for example improving wavelength selectivity of transmission and/or reflection.

In one exemplary embodiment of the present invention, the optical thin film 110 minimizes the reflection of light 125 incident on the substrate 120, effectively countering the tendency of the refractive index differential between the substrate 120 and the surrounding medium 185 to reflect light. This antireflective property can be either intentionally wavelength selective or operable across a purposely broad span of wavelengths. The transition layers 175 can enhance, control, or otherwise manage antireflection (or suppression of optical reflection).

In one exemplary embodiment of the present invention, the optical thin film 110 generates or heightens reflectivity in the interface between these two media 120, 185. The thin film structure 175 can enhance, control, or otherwise manage reflection at the material interface 175 or the outer surface 110.

In one exemplary embodiment of the present invention, the optical thin film 110 functions in a bidirectional manner, providing essentially equal manipulation of light 125 traveling in either a positive direction or a negative direction with respect to the z-axis 130. That is, the light 125 can travel through the optical thin film 110 either from the outer surface 185 to the inner surface 170 or from the inner surface 170 to the outer surface 185.

The optical thin film 110 in the exemplary optical system 100 illustrated in FIGS. 1A and 1B adheres to a substrate 120 that may comprise a plate of optical material, such as glass, silica, sapphire, or silicon. In this configuration, supporting and stabilizing the optical thin film 110 is the primary function of the substrate 120, rather than manipulating light such as collimating, beam steering, or focusing light.

In another exemplary embodiment of the present invention, the substrate 120 is a component, such as a gradient index lens or an optical fiber, that provides light manipulation, such as collimating light or guiding light. Exemplary passive components that can be substrates include diffractive elements, holographic lenses, concave lenses, convex lenses, cylindrical lenses, Fresnel lens, PLCs, prisms, circulators, isolators, lens arrays, ball lenses, micro-optic components, nano-optic elements, planar micro-lens arrays, ion-exchanged components, displays, interconnects, crystals, lenslets, lenticulars, diffusers, micro-fluidic components, or other passive components known to those skilled in the art, according to exemplary embodiments of the present invention.

In addition to passive manipulation, the substrate 120 can actively manipulate light. That is, the substrate 120 can be part of a vertical cavity surface emitting laser ("VCSEL"), distributed feedback ("DFB") laser, SOA, silicon optical amplifier ("SiOA"), silicon photonic device, silicon-based laser, Raman laser, erbium doped fiber amplifier ("EDFA"), erbium doped waveguide amplifier ("EDWA"), charge coupled device ("CCD"), light emitting diode ("LED"), avalanche photodiode ("APD"), indium gallium arsenide ("InGaAs") detector, optical modulator, germanium detector, sensor, or other active component known those skilled in the art, in accordance with exemplary embodiments of the present invention. The transition layers 175 can enhance operation of such devices.

In one exemplary embodiment, the optical thin film 110 is grown on the substrate 120, for example using a fabrication process similar to one that may be used for fabricating semiconductor devices. In one exemplary embodiment, the system 100 comprises a semiconductor material, such as a silicon-based material, InGaAs, germanium, indium phosphide, etc., and the thin film 110 comprises a doped semiconductor. Thus, the thin film 110 and the substrate 120 can comprise a monolithic material with the thin film 110 and the substrate 120 having differing levels of a dopant. Alternatively, the thin film 110 and the substrate 120 can each comprise a distinct doping material. The transition layers 175 can be formed with striations of such doping materials.

In one exemplary embodiment of the present invention, light may travel in the optical thin film 110 along the plane of the optical thin film 110, rather than through the thickness 160 of the optical thin film 110 as illustrated in FIG. 1. That is, light can either propagate through the optical thin film 110 at an acute angle with respect to the z-axis 130, parallel to the z-axis 130, or through the optical thin film 110 generally parallel to the plane defined by the x-axis 140 and the y-axis 150. In one exemplary embodiment of the present invention, the optical thin film 140 waveguides light. In one exemplary embodiment of the present invention, the optical thin film 140 is etched, for example in an inductively coupled plasma ("ICP") process, to form a structure that waveguides light. This waveguide structure can provide single mode light propagation.

The thickness 160 of the optical thin film 110 can be of an appropriate dimension to support single mode propagation in the direction of the x-axis 140 or the y-axis 150. In this case, the thickness 160 can be related to the wavelength of the single mode light and the refractive index differential between the optical thin film 110 and the surrounding materials 120, 185, which can function as waveguide cladding. These design parameters may be manipulated by one skilled in the art having the benefit of this disclosure to generate specific optical effects, for example. In one exemplary embodiment, the thickness 160 of the optical thin film 110 is approximately nine microns, and the mode field of the single mode light guided therethrough is approximately ten microns for a wavelength in the range of approximately 1310 to 1550 nanometers ("nm"). In certain exemplary embodiments, the optical thin film 110 can be characterized as a relatively thick layer.

In one exemplary embodiment of the present invention, a silicon photonic device comprises the optical film 110. The film 110, which may be thin, thick, or of arbitrary thickness, and the silicon photonic device can be a monolithic structure or a unitary structure or multiple structures fastened, attached, or bonded to one another. In such an embodiment, the film 110 can either conduct light though one or both of its faces 170, 180 or between/along those faces 170, 180 in a waveguide manner as discussed above. The silicon photonic device can comprise a lasing device that comprises silicon, an SiOA, a silicon-based modulator, an attenuator comprising silicon, a silicon-based detector, a silicon-based emitter, and/or an optically-pumped silicon amplifying device, to name a few examples.

Manipulating light at the optical interface of such an active silicon device via the transition layers 175 can enhance, control, or otherwise manage an operational aspect of a silicon photonic device. The result can be to manipulate or change the optical function, performance, or characteristics of the active silicon device, for example adjusting it to comply with a performance specification.

The eight documents listed immediately below disclose exemplary silicon photonic devices that can comprise an optical film or layer, such as the optical film 110, whose optical properties can be adjusted, managed, enhanced, or controlled using the technology, methods, processes, teachings, or technology discussed herein. That is, according to exemplary embodiments of the present invention, the optical properties of the optical films, materials, or elements of the systems disclosed in the below eight documents can be managed to provide a performance enhancement or an operational control. Moreover, the films disclosed in those eight documents can be adapted via the addition of transition layers 175. Further, extremely thin film layers that provide light management at an optical interface can be added to or integrated with the devices disclosed in those documents. In one exemplary embodiment a process, as discussed in further detail below, imparts such a silicon photonic device with a layer of graphene, graphite, or graphitic material. Such a layer can enhance the silicon photonic device's optical, electrical, and/or thermal/heat-dissipation performance, for example. The disclosures of the following eight documents are hereby incorporated by reference:

1) "*A Continuous-Wave Raman Silicon Laser,*" by Haisheng Rong, Richard Jones, Ansheng Liu, Oded Cohen, Dani Hak, Alexander Fang, and Mario Paniccia, *Nature* 3346, Mar. 2, 2005. Available at www.nature.com/nature and at www.intel.com.

2) "*An All-Silicon Raman Laser,*" by Haisheng Rong, Ansheng Liu, Richard Jones, Oded Cohen, Dani Hak, Remus Nicolaescu, Alexander Fang, and Mario Paniccia, *Nature*, Volume 433, Jan. 20, 2005. Available at www.nature.com/nature and at www.intel.com.

3) "*Silicon Shines On,*" by Jerome Faist, *Nature* Volume 433, Feb. 17, 2005. Available at www.nature.com/nature and at www.intel.com.

4) "*Continuous Silicon Laser, Intel researchers create the first continuous silicon laser based on the Raman effect using standard CMOS technology,*" by Sean Koehl, Victor Krutul, and Mario Paniccia, published by Intel Corporation as a white paper, 2005. Available at www.intel.com.

5) "*Intel's Research in Silicon Photonics Could Bring High-speed Optical Communications to Silicon,*" by Mario Paniccia, Victor Krutul, and Sean Koehl, published by Intel Corporation as a white paper, February 2004. Available at www.intel.com.

6) "*Silicon Photonics,*" by Mike Salib, Ling Liao, Richard Jones, Mike Morse, Ansheng Liu, Dean Samara-Rubio, Drew Alduino, and Mario Paniccia, *Intel Technology Journal*, Volume 08, Issue 02, May 10, 2004. Available at www.intel.com (http://developer.intel.com/technology/itj/index.html).

7) "*Introducing Intel's Advances in Silicon Photonics,*" by Mario Paniccia, Victor Krutul, Sean Koehl, published by Intel Corporation as a white paper, February 2004. Available at www.intel.com.

8) "*Intel Unveils Silicon Photonics Breakthrough: High-Speed Silicon Modulation,*" by Mario Paniccia, Victor Krutul, and Sean Koehl, *Technology@Intel Magazine*, February/March 2004. Available at www.intel.com.

Referring now to FIG. 1B, the optical thin film 110 can be operative to manipulate light 125 of various or highly selective wavelengths regions. In one exemplary embodiment of the present invention, the optical thin film 110 manipulates visible light 125 between about 400 nm and about 700 nm. In one exemplary embodiment of the present invention, the optical thin film 110 manipulates light 125 in the near infrared region between about 700 nm and about 3500 nm. In one exemplary embodiment of the present invention, the optical thin film 110 manipulates light between about 700 nm and about 900 nm. In one exemplary embodiment of the present invention, the optical thin film 110 manipulates UV light 125. In one exemplary embodiment of the present invention, the optical thin film 110 manipulates light 125 at typical single-mode optical networking wavelengths, in the region between about 1200 nm and about 1750 nm. In one exemplary embodiment of the present invention, the optical thin film 110 manipulates light 125 in one or more spectral regions that provide low-loss transmission over optical fibers. Such low-loss spectral regions can be windows of low water absorption, such as about 1310 nm and about 1550 nm. The thickness 160 of the optical thin film 110 can be selected to provide specific manipulation effects of light 125 or electromagnetic radiation.

In one exemplary embodiment of the present invention, the optical thin film 110 is an element in a sensor system and is operative to guide light in a direction generally parallel to the x-y plane 140, 150. The outer surface 180 of the optical thin film 110 provides a sensing interface. Light propagating in the optical thin film 110 interacts with the medium 185 that is adjacent this sensing interface.

In one exemplary embodiment of the present invention, the optical thin film 110 and/or the transition layers 175 are formed in a deposition process, which can be ion plating, ion assisted deposition ("IAD"), ion sputtering, plasma assisted deposition, or magnetron sputtering. Ion plating can be carried out with evaporation and/or with plasma. The deposition process can be a vacuum process, conducted in a deposition chamber at a pressure of less than one atmosphere. These deposition processes can be reactive, for example reactive ion beam sputtering. Introducing nitrogen gas into the deposition chamber while sputtering silicon dioxide can form a transition layers 175 of silicon oxynitride in a reactive manner. Alternatively, a silicon target can be sputtered while introducing oxygen and nitrogen into the deposition chamber.

In one exemplary embodiment of the present invention, a physical vapor deposition ("PVD") process such as evaporation or sputtering forms the optical thin film 110 and/or the transition layers 175. In one exemplary embodiment of the present invention, electron-beam ("e-beam") evaporation or dual e-beam evaporation forms the transition layers 175 and/or the optical thin film 110. In one exemplary embodiment of the present invention, e-beam IAD beam ion assisted deposition forms the transition layers 175 and/or the optical thin film 110. Reactive e-beam IAD can form the transition layers 175 and/or the optical thin film 110 by introducing nitrogen into the deposition chamber during e-beam IAD using a silicon dioxide target in a reactive process that can be a stoichiometric process.

In one exemplary embodiment of the present invention, direct current ("DC") sputtering or radio frequency ("RF") sputtering forms the transition layers 175 and/or the optical thin film 110. The sputtering process can be carried out in a reactive manner, for example. The transition layers 175 and/or the optical thin film 110 can also be formed with pulsed laser deposition. The optical thin film 110 and/or the transition layers 175 can also be printed or spun on to the substrate 120 or formed with a sol gel process.

In one exemplary embodiment of the present invention, the transition layers 175 and/or the optical thin film 110 are formed with epitaxial growth, such as liquid phase epitaxy ("LPE"), molecular beam epitaxy ("MBE"), vapor phase epitaxy ("VPE"). In one exemplary embodiment of the present invention, the optical thin film 110 is formed with a chemical vapor deposition ("CVD") process such as atmospheric pressure chemical vapor deposition ("APCVD"), low-pressure chemical vapor deposition ("LPCVD"), very low-pressure chemical vapor deposition ("VLPCVD"), plasma-enhanced chemical vapor deposition ("PECVD"), laser-enhanced chemical vapor deposition ("LECVD"), metal-organic chemical vapor deposition ("MOCVD"), or electron-cyclotron resonance chemical vapor deposition ("EPCVD"). The above list of processes for forming the optical thin film 110 and/or the transition layers in accordance with various embodiments of the present invention is an exemplary, rather than an exhaustive, list.

In one exemplary embodiment of the present invention, the optical thin film 110 and the accompanying transition layers 175 are deposited on the optical substrate 120 in a vacuum deposition process. In another exemplary embodiment of the present invention, the optical thin film 110 and the accompanying transition layers 175 are grown on a silicon substrate. Thus, the substrate 120 is silicon and the material adhering thereto are composed of an oxide layer on the surface of the silicon.

In one exemplary embodiment of the present invention, the transition layer 175 and/or the optical thin film layer 110 is composed of silicon oxynitride ($SiO_xN_y$) grown by a hybrid deposition based on the combination of pulsed laser deposition of silicon in an oxygen background together with a plasma based nitrogen source. Controlling the partial pressure of nitrogen with respect to oxygen in the deposition chamber controls the nitrogen content in the optical thin film 110 and/or the transition layers 175.

In one exemplary embodiment of the present invention, the transition layer 175 and/or the optical thin film 110 is produced by reactive magnetron sputtering of a silicon target in a variable mixture of oxygen and nitrogen, which are the reactive gasses. The resulting optical structures comprise silicon oxynitride ($SiO_xN_y$). Adjacent individual layers (typically nano-scaled) of the transition layers 175 can comprise varying concentrations of oxygen and/or nitrogen, wherein those concentrations control refractive index. Thus, the values of "x" and "y" in the $SiO_xN_y$ can vary in each layer.

In one exemplary embodiment of the present invention, the transition layers 175 and/or the optical thin film 110 comprise amorphous silicon oxynitride with at most a trace level of Ge. Moreover, the fabrication process can comprise electron beam physical vapor deposition ("EB-PVD") at a low temperature.

In one exemplary embodiment of the present invention, the transition layers 175 and/or the optical thin film 110 are formed via reactive RF sputter deposition. Sputtering a silicon nitride target in an oxygen environment can form the transition layers 175 and/or optical thin film 110. Varying the flow rate of oxygen in the deposition chamber can control the refractive indices to form the individual layers of the transition layers 175, for example providing refractive indices between approximately 1.46 and 2.3. The RF power can be approximately 500 watts and the refractive index of the deposited material can vary in a linear manner with respect to the oxygen flow rate. With a sputtering gas having approximately ten percent (10%) oxygen and ninety percent (90%) argon, adjusting the gas flow rate between approximately nine standard cubic centimeters per minute ("sccm") and twenty one sccm can produce a corresponding and essentially linear control of refractive index between approximately 1.8 and 1.5.

In one exemplary embodiment of the present invention, the optical thin film 110 is an antireflective coating comprising the transition layers 175 with a composition of silicon oxynitride generated in an ion-beam sputtering deposition system. Such film 110 can be essentially void of Ge. The optical thin film 110 can further be a stoichiometric layer, formed in a reactive ion-beam sputtering process and having a high density and essentially no so-called columnar structures visible in scanning electron microscopy analysis.

The substrate 120 can be a semiconductor material, including a semiconductor laser facet or an optical amplifier facet. Alternatively, the optical thin film 110 can be a high reflectivity coating on a laser facet, for example on the back facet of a laser die or a semiconductor device that amplifies light. In both cases the optical thin film 110 can comprise or be associated with the transition layers 175.

In one exemplary embodiment of the present invention, the optical thin film 110 and the accompanying transition layers 175 are formed with a physical vapor deposition process based on RF sputtering, which can include dual frequency RF sputtering. Several options are available to control the refractive index during the deposition process. Adjusting the deposition temperature can control the refractive index, with an increase in deposition temperature providing an increase in refractive index. Increasing the RF power applied to the target during the deposition process also can increase refractive index. Adding a reactive gas to the sputtering chamber can modulate the chemical composition of the deposited material, thereby imparts the individual transition layers 175 with corresponding changes in refractive index. Furthermore, using a target material in a specific oxidation state can control refractive index during the deposition process.

The RF sputtering method is also applicable to depositing pure materials and mixed materials including rare earth dopants. Adding a reducing gas, such as hydrogen, to the chamber while the optical thin film 110 and the accompanying transition layers 175 are forming can provide an increase in refractive index. On the other hand, the refractive index can be decreased by adding an oxidizing gas, such as oxygen. Replacing argon as the sputtering gas with approximately two percent (2%) hydrogen ($H_2$) in argon may increase the refractive index by approximately two percent (2%) or more. In one exemplary embodiment of the present invention, a portion of the hydrogen may remain in the system 100 following deposition.

Replacing a portion of the argon gas that is present in RF sputtering environment with nitrogen can adjust the composition and refractive index of the transition layers 175 and the optical thin film 110. For example replacing approximately thirty three percent (33%) of such argon with nitrogen while sputtering a silicon dioxide ($SiO_2$) target may yields approximately seven percent (7%) increase in refractive index. Fabricated in this manner, the optical system 100 may contain $SiO_xN_y$.

In one exemplary embodiment of the present invention, such nitrogen is introduced in the deposition chamber during the formation of a wave division ("WDM") filter, DWDM filter, or course wave division multiplexing ("CWDM") filter having layers of tantalum pentoxide and silicon dioxide. Injecting nitrogen into the chamber during the deposition of one or more silicon dioxide layers, such as a specific transition layer in a multi-cavity filter can cause those layers to contain $SiO_xN_y$. Evacuating the nitrogen from the chamber following formation of such a layer can reduce the level of $SiO_xN_y$ in subsequent silicon dioxide layers.

In one exemplary embodiment of the present invention, a silicon monoxide (SiO) target is sputtered in an argon environment to impart one or more selected transition layers of the transition layers 175 with a refractive index of slightly above 2. Altering the composition of the sputtering environment can lower the refractive index to approximately 1.75, for example to produce selected low-refractive index transition layers within the transition layer system 175.

Processes that may be used in connection with fabricating the system 100, including the transition layers 175 and the thin film layer 110, include: RF sputtering deposition of $SiO_2$; RF sputtering deposition of $SiO_2$ with index modulation; RF sputtering deposition of SiO and erbium doped SiO; single and/or dual frequency RF sputter deposition of silica; PECVD deposition, to name a few possibilities.

In one exemplary embodiment of the present invention, the composition of at least one of the transition layers 175 and/or the optical thin film 110 can be represented by the formula $Si_{1-x}Ge_xO_{2(1-y)}N_{1.33y}$ wherein "x" is approximately between 0.05 to 0.6, and "y" is approximately between 0.14 and 0.74. The resulting refractive index can be approximately from 1.6 to 1.8, variable with composition, process conditions of film formation, heat treatment, and other factors. The substrate 120 can be glass, silicon, or another optical or optoelectronic material.

Such optical thin films 110 and transition layers 175 can be formed with a PECVD process using a parallel plate reactor with a heated stationary platen, a low frequency (375 kHz) RF generator and matching network, and a gas manifold supplying silane, germane (germanium hydride, $GeH_4$), nitrous oxide, ammonia, and nitrogen into the process chamber through a showerhead nozzle that uniformly distributes the reactive gasses.

In another exemplary embodiment of the present invention, the transition layers 175 and/or the optical thin film 110 is formed by mechanically processing a boule or preform of optical fiber material. Thus, a process for forming the system 100 can comprise processing a blank or rod of the fiber optic material that might otherwise be drawn into optical fiber in a process conducted in a drawing tower. The stock of fiber optic material can be temporarily attached, for example in a jig configuration, to a base substrate and ground down through mechanical grinding and polishing. Alternatively, the material can be thinned with chemical, plasma-based, or ion-based etching conducted in a vacuum environment or ICP etching.

In one exemplary embodiment, the compensation of the optical thin film 110 and/or the transition layers 175 can have a specific concentration within a range of concentrations of Ge—$O_2$, for example between 0.25 percent and 15 percent. In one exemplary embodiment, a section of the optical thin film 110 and/or at least one of the transition layers 175 comprises essentially pure silicon dioxide, with only trace levels of Ge.

In one exemplary embodiment of the present invention, the system 100 comprises boron and Ge. For example, the boron may be co-doped with approximately 12% Ge in $SiO_2$.

In one exemplary embodiment of the present invention, the thin film 110 illustrated in is deposited on the substrate 120 as essentially pure silicon dioxide, which typically includes small quantities of silicon monoxide and various impurities.

In one exemplary embodiment of the present invention, the system 100 comprises a composition of fused silica with a $GeO_2$ mole-fraction concentration between 0.12 and 0.16. In one exemplary embodiment of the present invention, the system 100 comprises a composition of vacuum deposited silica with a $GeO_2$ mole-fraction concentration between 0.02 and 0.16. In one exemplary embodiment of the present invention, the $GeO_2$ mole-fraction concentration of at least some portion of the system 100 varies from a level that approaches zero to a level of approximately 2.0. In one exemplary embodiment of the present invention, the system 100 comprises a composition of silicon dioxide with a $GeO_2$ mole-fraction concentration greater than 0.04.

In one exemplary embodiment of the present invention, energy can be used to control or to adjust an optical property of the transition layers 175, or of a larger system that comprises the transition layers 175. Exemplary technology, including a method and a system, for controlling, adjusting, or managing such an optical property is provided in U.S. Nonprovisional patent application Ser. No. 11/127,558, filed May 12, 2005 and entitled "Adjusting Optical Properties of Optical Thin Films," the entire contents of which are hereby incorporated herein by reference.

Turning now to FIG. 2, this figure illustrates an exemplary stack of optical thin films 175, 220, 230, 240 on a substrate 120 according to an embodiment of the present invention. In various embodiments, the system 200 can be characterized as comprising laminated layers or adjoining films of optical material or sections of optical materials facing one another. As discussed above with reference to FIG. 1, the system 200 can comprise transition layers 175, for example at the interfaces 275 between the individual thin film layers 220, 230, 240. Exemplary embodiments of such transition layers 175 will be discussed below in further detail with reference to FIGS. 4-16.

The optical system 200 can comprise part of a thin film optical filter, such as a dense wavelength division multiplexing ("DWDM") filter or a laser-rejection filter for laser-Raman spectroscopy. As an optical filter, the optical system 200 can be a high pass filter, a low pass filter, a band pass filter, or a notch filter. Alternatively, the optical system 200 can provide gain compensation, gain flattening, chromatic dispersion compensation, group delay correction, spectrally selective delay in an optical network or other optical manipulation based on interference of light interacting with each of the thin film layers 175, 220, 230, 240, the interfaces 275 of thin film layers 175, 220, 230, 240 and the substrate 120. In one exemplary embodiment of the present invention, this optical system 200 is an element in a frequency/wavelength locking system, such as an etalon-based "locker," for a telecommunication application. One or more of the thin film layers 220, 230, 240 in the stack typically has accompanying transition layers 175 that enhance the performance of the system 200.

Moreover, an exemplary embodiment of the present invention can include multiple optical thin film layers 175, 220, 230, 240 individually interacting with light 125 of an end-use application. For example, the light 125 may have digital information coded thereon, and the light interactions from each individual layer 220, 230, 240 are collectively additive or subtractive upon one another.

One or more of the layers 175, 220, 230, 240 can embody certain functions described herein and illustrated in the examples, compositions, tables, functional block diagrams, and appended flow charts. However, it should be apparent that there could be many different ways of implementing aspects of the present invention in optical films, and the invention should not be construed as limited to any one optical thin film configuration. Further, a skilled engineer would be able to create various thin film embodiment without difficulty based on the exemplary functional block diagrams, flow charts, and associated description in the application text, for example.

Therefore, disclosure of additional designs of stacks of the optical thin film layers 175, 220, 230, 240, beyond those presented herein, are not considered necessary for an adequate understanding of how to make and use the present invention. The inventive functionality of any multilayer aspects of the present invention will be explained in more detail in the following description in conjunction with the remaining figures illustrating the functions, compositions, applications, and processes. That is, the transition layers 175 can be applied to a wide range of applications including interference filters and other systems.

For many filtering applications, the pass band(s) and the reflection band(s) of the system 200 should be flat, with a high level of transmission and minimal or controlled ripple. The system 200 should also provide a minimal level of light rejected within the pass band for many applications. Rejected light, particularly if the optical system 200 reflects the rejected light, can cause problems for an application. For example, reflected light within a pass band can mix with the reflected light outside the pass band and become interference or stray light that can degrade the signal-to-noise ratio of an optical communication system, optical instrumentation system, or other optical system. Consequently, a high degree of stray light rejection (or a high level of transmission) within the pass band of a thin film optical filter is typically desirable. In many circumstances, the transition layers 175 can promote isolation, reduce stray light, control ripple, or enhance the flatness of pass bands or reflection bands.

In one exemplary embodiment, the transition layers 175 can control, improve, or reduce optical dispersion or group delay. Whereas group delay is typically measured in the units of picoseconds ("ps"), dispersion is typically measured in picoseconds per nanometer ("ps/nm"). That is, dispersion can be the derivative, with respect to nanometers, of group delay.

Improving the dispersion or group delay of the system 200 can enhance optical performance in a high-speed optical networking application, for example an environment of transmitting data at 10 Gigabit per second, 40 Gigabits per second, or at a higher rate. For example, a high level of dispersion or group delay performance can support a desirable bit error rate performance in an optical communications network. Similarly, improved group delay can relax a laser specification for an optical network application.

Thus in an exemplary embodiment, the transition layers 175 can control the residence times of photons having different colors in an optical device. That is, the transition layers 175 can help a device, such as the system 200, operate over a span of wavelengths with defined or controlled levels of delay for light of those wavelengths.

In one exemplary embodiment of the present invention, the chromatic dispersion characteristics of the transition layers 175 can correct or compensate for chromatic dispersion. For example, controlling the dispersion or group delay of the system 200 to achieve a desired spectral profile can be more beneficial than minimizing those optical characteristics.

Moreover, transition layers 175 can manage dispersion or a group delay spectral profile of an optical device to meet a target specification. The resulting device can compensate for chromatic dispersion of optical signals occurring on a span of fiber, in an optical amplifier, or laser cavity, for example. Accordingly, the transition layers 175 can control the chromatic dispersion of a compensating device so that the device can be placed in series with other devices that chromatically disperse light and so that the aggregate chromatic dispersion is flat.

The Thin Film Center Inc. of Tucson Ariz. provides products and services that can be useful in modeling certain aspects of the system 200. Moreover, the company's design and analysis package, marketed under the product name "The Complete Macleod" can be a useful tool for designing the configuration of the layers 175, 220, 230, 240 to achieve a particular application objective.

The software products of Software Spectra Inc, the Thin Film Center, and other suppliers of analytical tools for optical coatings, can support modeling thin film layers, such as the layers 175, 220, 230, 240 of the optical system 200. Such software can assist a designer in specifying various parameters of the system 200 to achieve a desired optical effect. For example, specifying certain parameters could support achieving a group delay target. Yet another useful coating design and analysis tool is the software product known under the trade name FILMSTAR and available from FTG Software Associates of Princeton, N.J.

The above discussion, with reference to FIG. 1, of embodiment variations, forms, uses, fabrication processes, applications, etc. generally applies to the system 200 of FIG. 2. For example, the system 200 might comprise a monolithically integrated or crystalline semiconductor material having compositional striations that functionally form the layers 175, 220, 230, 240. Thus, the layers 220, 230, 240 can arise from variations (or spatial modulations) in one or more doping chemicals (or elements) of an otherwise homogenous material. Nevertheless, the following discussion with will concentrate on an exemplary embodiment of thin film layers 220, 230, 240, that may comprise oxide or dielectric material, adhering to an optical substrate 120 as might be formed in a vacuum deposition chamber.

Accordingly, the thin film layers 175, 220, 230, 240 can be deposited on the substrate 120 in a vacuum or near-vacuum deposition process. The substrate can be glass, BK-7 glass, silicate, fused silica, silicon, or other optical material that is generally transparent to or that is otherwise compatible with the wavelengths of the light (exemplary illustrated as the element 125 in FIG. 1) that the optical system 200 manipulates.

The stack includes thin film layers 175, 220, 230 of alternating refractive index disposed face-to-face or adjacent one another. Thus, the layers denoted with the reference number "220" may be high refractive index, while the layers denoted with the reference number "230" may be relatively low refractive index. In one exemplary embodiment of the present invention, the material compositions of the high refractive index layers 220 and the low refractive index layers 230 (and/or the transition layer 175) include tantalum pentoxide ($Ta_2O_5$) and silicon dioxide ($SiO_2$) respectively.

In one exemplary embodiment of the present invention, the composition of at least one of the layers 175, 220, 230, 240 includes silicon oxynitride. In one exemplary embodiment of the present invention, the composition of at least one of the thin film layers 175, 220, 230, 240 includes diamond (such as diamond-like carbon), graphene, graphic layers, graphitic material, magnesium fluoride ($MgF_2$), dielectric material, silicon, titanium dioxide ($TiO_2$), aluminum oxide ($Al_2O_3$), metal oxide, among other possibilities.

In one exemplary embodiment of the present invention, the composition of at least one of the thin film layers 175, 220, 230, 240 includes germanium (Ge). In one exemplary embodiment of the present invention, at least one of the alternating refractive index thin film layers 175, 220, 230, 240 is an essentially pure optical material. The packing density of the alternating refractive index layers 175, 220, 230, 240 is typically greater than 95 percent. The physical properties of these layers 175, 220, 230, 240 typically approach that of bulk material.

The exemplary stack of optical thin film layers 175, 220, 230, 240 includes two spacer layers 240, that may function to provide a multi-cavity interference device. Thus, the system 200 of thin films can comprise a plurality of cavities that function as an etalon. The spacer layers 240 are each disposed between two banks 250 of layers 175, 220, 230 of alternating, high-low refractive index material. In one exemplary embodiment of the present invention, the composition of one or more of the spacer layers 240 includes silicon dioxide or another dielectric material. In one exemplary embodiment of the present invention, the composition of one or more of the spacer layers 240 includes silicon oxynitride. In one exemplary embodiment of the present invention, the composition of one or more of the spacer layers 240 includes germanium and/or hydrogen. In one exemplary embodiment of the present invention, each of the spacer layers 240 is deposited as an essentially pure optical material. The packing density of the spacer layers 240 is typically greater than 95 percent. The physical properties of these layers 240 approach that of bulk material.

The transition layers 175 can be graduated along the x-axis 140 so that various ones of the transition layers 175 are different from one another in some aspect. Thus, a transition layer 175 at a first location along the x-axis 140 can be different (for example in form, composition, or function) from a transition layer 175 at a second location along the x-axis 140. The differences among the transition layers 175 can be progressive or gradual, for example. Alternatively, the transition layers 175 can be essentially uniform with respect to one another along the x-axis 140. That is, each of the transition layers 175 can have essentially the same form, function, composition, or operability along the x-axis 140.

In one exemplary embodiment of the present invention, the banks 250 of high-index layers 220 and low-index layers 230 are composed of tantalum pentoxide and silicon dioxide respectively and the transition layers 175 comprise silicon oxynitride, tantalum pentaoxide, and/or silicon dioxide.

In one exemplary embodiment of the present invention, the high index layers 220 are tantalum pentoxide; the low-index layers 230 are composed of magnesium fluoride; and the transition layers 175 comprise silicon oxynitride, magnesium fluoride, tantalum pentoxide, and/or silicon dioxide.

The transition layers 175 can enhance the operation or utility of a thin film optical filter for example providing precise control over center wavelength, an improved level of light rejection, or enhanced transmission.

In one exemplary embodiment of the present invention, the layers 175, 220, 230, 240 are formed with e-beam IAD. The high-index layers 220 and low-index layers 230 are composed of tantalum pentoxide and silicon dioxide and are deposited on an optical substrate 120 using tantalum pentoxide and silicon dioxide targets in sequence for each respective layer 220, 230. Further, the transition layers 175 comprise tantalum pentoxide and silicon dioxide and are deposited using tantalum pentoxide and silicon dioxide targets in sequence for each respective transition layer 175.

In one exemplary fabrication embodiment, when the deposition process progresses to each transition layer 175, a process controller activates a silicon dioxide target and adds nitrogen to the deposition chamber at an appropriate level to impart the respective layers of each transition layer 175 with a predefined refractive index. The controller can modulate the silicon dioxide and nitrogen discretely or in controlled steps, thus forming transition layers 175 or individual transition layers that comprise silicon oxynitride.

After forming each set of transition layers 175, the deposition process can shut off the nitrogen supply, eliminate the nitrogen from the deposition chamber, and return to depositing silicon dioxide and tantalum pentoxide, with only minimal or trace concentrations of nitrogen in the high-index layers 220 and low-index layers 230 of the layer bank 250.

In one exemplary embodiment of the present invention, the system 200 is a thin film optical filter or other multi-layer interference device and is formed by ion beam sputtering. At least one of the layers 175, 220, 230, 240, 250 could be formed by dual ion beam sputtering.

In one exemplary embodiment, at least one of the layers 175, 220, 230, 240, 250 comprises silicon oxynitride that can be represented as $SiO_xN_y$, with a refractive index between approximately 1.5 and 2.0, depending on the relative values of "x" and "y."

In one exemplary embodiment of the present invention, an optical networking device comprises the system 200. For example, an add-drop optical multiplexing ("OADM") filtering device can comprise the system 200. In this embodiment, the substrate 120 can be a gradient index lens with the thin film layers 175, 220, 230, 240 operating as a notch filter that provides a narrow band of reflection.

One ingress single mode optical fiber (not shown) delivers multi-color light to the gradient index lens, on the opposite side of lens from the thin film layers 175, 220, 230, 240. The lens, which is typically inside a device housing, collimates this multicolor light from the ingress fiber and delivers the collimated light to the thin film layers 175, 220, 230, 240. The reflection band or notch of the filter 200 reflects a spectral region of light, delivering the reflected light as one or more drop channels to a drop fiber that is adjacent the ingress fiber. Meanwhile, the transmission region of the filter 200 transmits the express channels to an egress fiber that is butted to another lens on the opposite side of the thin film layers 175, 220, 230, 240 from the substrate 120 (which is the other grin lens in this example).

An optical network, such as a SONET, gigabit Ethernet, access, storage, local area network ("LAN"), Internet protocol ("IP"), or other network can comprise the system 200, functioning as the described OADM filter. Such a network can carry a wide range of voice, data, video, or other communications.

As discussed above, the transition layers 175 can enhance performance of such an OADM notch filter, for example helping control a center wavelength of a stop band, the cut-on wavelength of a stop band, the dispersion, the group delay, or the attenuation profile.

In one exemplary embodiment of the present invention, the system 200 comprises a planar graphite, graphene, or graphitic layer. A method and system for making such a layer is disclosed in U.S. Pat. No. 7,015,142, entitled "Patterned Thin Film Graphite Devices and Method for Making Same" and filed on Jun. 3, 2004, the entire contents of which are hereby incorporated herein by reference. Moreover, a graphitic, graphite, or graphene layer can have an accompanying set of transition layers 175. In one exemplary embodiment, a plurality of adjoining graphitic, graphite, or graphene layers produces an interference effect on electrons present in the layers. Accordingly, such layers can filter electrons according to wavelength, frequency, or energy level. In one exemplary embodiment, a graphitic, graphite, or graphene layer is patterned with a corrugation or a series of grooves that functions as a grating for electrons moving in the layer. Thus, a graphitic, graphite, or graphene layer fabricated in accordance with the disclosure of U.S. Pat. No. 7,015,142 can be etched to provide a structure that interacts with electrons via diffraction or interference.

In one exemplary embodiment of the present invention, the substrate 120 is a block, slab, or crystal of silicon, and the thin film layer 110 is a graphitic layer or comprises graphite or graphene. In one exemplary embodiment, the substrate 120 is such silicon and the thin film layer 110 is a single graphene layer, with a single or essentially unitary layer of carbon atoms. In one exemplary embodiment, the substrate 120 is such silicon, and the thin film layer 110 is a graphite layer made of a plurality of layers of carbon atoms. The number of layers can be controlled to an exact or approximate number or to be within a specified range. The film 110 can, for example, have a thickness of two, five, ten, fifteen, twenty, fifty, seventy five, one hundred, or in a range thereof. Such carbon atoms can be crystalline or otherwise have a long-term order, structure, or repeated pattern.

Comprised of graphitic, graphite, or graphene material, the layer 110 can be formed on the substrate 120 of silicon by creating a silicon carbide layer on silicon and then processing the silicon carbide layer to form the graphitic, graphite, or graphene layer. The silicon carbide layer can be formed on silicon using a technology and/or process disclosed or taught in U.S. Pat. No. 5,861,346, which is entitled "Process for Forming Silicon Carbide Films and Microcomponents" and issued Jan. 19, 1999 in the name of Hamza et al., the entire contents of which are hereby incorporated herein by reference. The resulting product, silicon substrate with silicon carbide attached thereto, can be processed using a technology and/or process disclosed or taught in U.S. Pat. No. 7,015,142, which is discussed above. Accordingly, from the silicon carbide, the processing can create graphite, graphene, or graphitic material adhering to the silicon substrate. The layer attachment can be direct, without requiring glues or bonding agents, for example.

In one exemplary embodiment, the silicon substrate can actively process light or electrons that couple to or from the graphite, graphene, or graphitic layer. In one exemplary embodiment, light propagating in the silicon substrate interacts with the graphite, graphene, or graphitic layer. In one exemplary embodiment, electrons propagating in the silicon substrate interact with the graphite, graphene, or graphitic layer. In one exemplary embodiment, light propagating in the graphite, graphene, or graphitic layer interacts with the silicon substrate. In one exemplary embodiment, electrons propagating the graphite, graphene, or graphitic layer interacts with the silicon substrate. In one exemplary embodiment, light and/or electrons propagating in the silicon substrate interact light and/or electrons propagating in the graphite, graphene, or graphitic layer.

Accordingly, the graphite, graphene, or graphitic layer can enhance, control, or manage the operation of the system to which it is attached. For example, the silicon substrate can comprise integrated elements, such as transistors or logical gates, that manipulate electrons via power levels (or some other transistor-type function). And, the graphite, graphene, or graphitic layer can comprise integrated elements, such as gratings, interferometers, etalons, or thin film stacks, that manipulate the electrons via interference or diffraction. The active substrate and the layer can function in a collaborative manner, for example manipulating the same electrons in a serial or parallel manner.

An exemplary processes for fabricating a system comprising graphite, graphene, or graphitic material atomically or molecularly bonded to a silicon base follows below, as Steps A, B, C, D, and E. In one exemplary embodiment, the process, or a derivative thereof, can produce a silicon photonic device, as discussed above, that comprises a layer of graphene, graphite, or graphitic material.

At Step A, one or more known silicon processing techniques impart silicon base with one or more patterns, features, active areas, transistors, gates, light manipulators, amplifiers, optical amplifiers, micro electromechanical systems ("MEMS") elements, optical devices, lenses, logical elements, doped features or regions, active elements, etc.

At Step B, typically following Step A, processing in accordance with the disclosure and teaching of U.S. Pat. No. 5,861, 346 forms, deposits, or provides one or more layers of silicon carbide on the silicon substrate that results from Step A.

In one exemplary embodiment, the silicon carbide material can comprise one or more patterns, features, active areas, transistors, gates, light manipulators, amplifiers, optical amplifiers, micro electromechanical systems ("MEMS") elements, optical devices, lenses, logical elements, doped features or regions, active elements, etc. An exemplary method or technology for forming such an active element in the silicon carbide can be found in U.S. Pat. No. 6,278,133, entitled "Field Effect Transistor of SiC for High Temperature Application, Use of Such a Transistor, and a Method for Production Thereof," the entire contents of which are hereby incorporated herein by reference. Another exemplary method or technology for imparting the silicon carbide material with a useful feature or device can be found in U.S. Pat. No. 6,127,695, entitled "Lateral Field Effect Transistor of SiC, a Method for Production Thereof and a Use of Such a Transistor," the entire contents of which are hereby incorporated herein by reference.

At Step C, typically following Step B, processing in accordance with the disclosure and teaching of U.S. Pat. No. 7,015, 142 forms a layer or layers of graphite, graphene, or graphitic material using part or essentially all of the silicon carbide film as a precursor, a base material, or a stock.

Accordingly, a silicon-carbide-based element (such as one or more patterns, features, active areas, transistors, gates, light manipulators, amplifiers, optical amplifiers, micro electromechanical systems ("MEMS") elements, optical devices, lenses, logical elements, doped features or regions, active elements, etc.) can comprise graphite, graphene, or graphitic material, such as a layer or a film thereof.

At Step D, typically following Step C, processing in accordance with U.S. Pat. No. 7,015,142 imparts a layer or layers of graphite, graphene, or graphitic material with a structure, such as a Mach-Zender interferometer, a diffraction grating, a corrugated grating, an etalon, or a stack of layers, that is operative to manipulate electrons via interference or diffraction.

At Step E, typically following Step D, the resulting system can be placed in operation. Placing the system in operation typically comprises supplying the system with light, electrons, or some other form of energy. In operation, light, electrons, particles, radiant energy, and/or energy waves couple between the silicon substrate and the layer(s) that comprises graphite, graphene, or graphitic material.

Figure 3A:
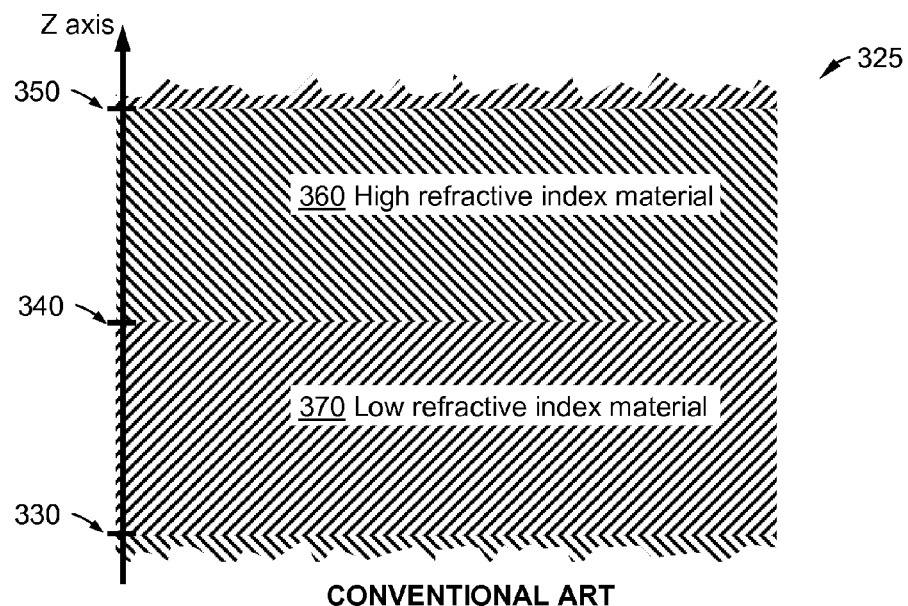
FIGS. 3A and 3B, collectively FIG. 3, respectively illustrate a cross section and a refractive index plot of a conventional stack of optical thin film layers.
Figure 3B:
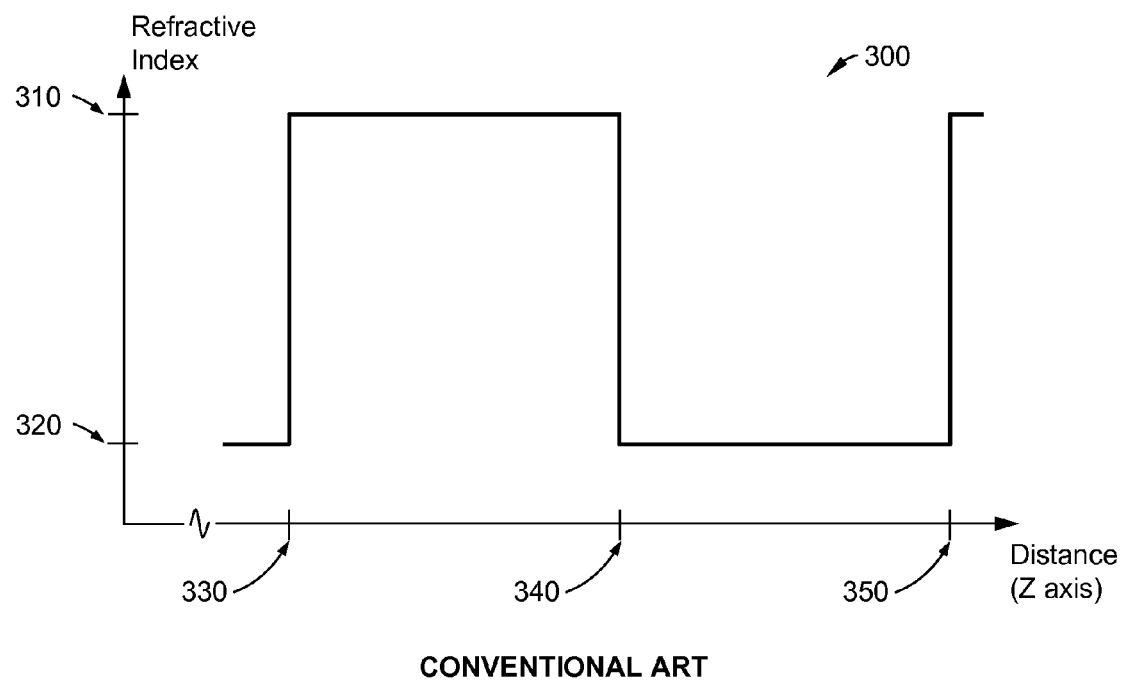

Turning briefly to FIG. 3, FIGS. 3A and 3B, respectively illustrate a cross sectional view 325 and a refractive index plot 300 of a conventional stack of optical thin film layers. As discussed above in the Background, conventional optical thin film systems often have abrupt changes or a "step changes" in refractive index and in material composition at the interfaces 330, 340, 350 between each thin film layer 360, 370. In many situations, smoothing such step changes, such as provided by transition layers 175 (not shown in FIG. 3 but discussed below) is desirable.

Figure 4:
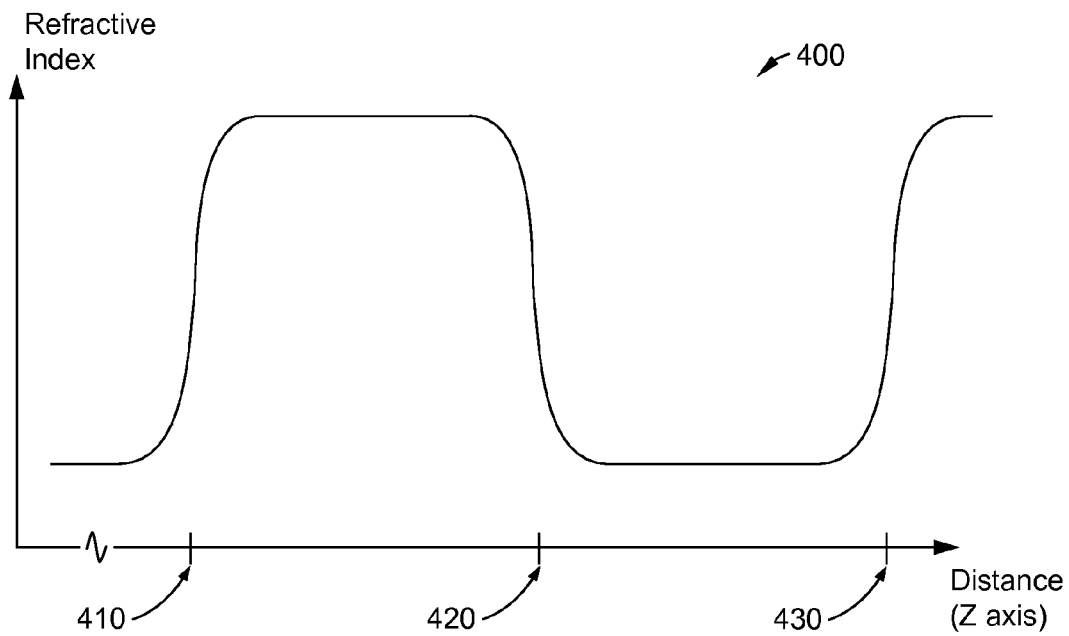
FIG. 4 illustrates a high-level plot of refractive index of a plurality of thin film layers, generally resembling a smoothed square wave, in accordance with an exemplary embodiment of the present invention.

Turning now to FIG. 4, this figure illustrates a high-level plot 400 of refractive index of a plurality of exemplary thin film layers, generally resembling a smoothed square wave, according to an embodiment of the present invention. The plot 400 can also be viewed as a square wave with rounded edges. The plot 400 provides an exemplary result of adapting the system 325 of FIG. 3A so that the adapted version of the system 325 comprises transition layers 175 at the interfaces 330, 340, 350.

Adding the transition layers 175 can provide the smooth refractive index transitions 410, 420, 430 of the plot 400 of FIG. 4 in contrast to the abrupt refractive transitions or refractive index discontinuities shown at the places 330, 340, 350 of the plot 300 of FIG. 3.

Thus, the plot 400 of FIG. 4 exemplifies a refractive index profile of the layers 220, 230 and the accompanying interfaces 175 and transition layers 175 of the system 200 shown in FIG. 2 and discussed above. The area (along the horizontal axis) between the marker 410 and the marker 420 corresponds to a high index layer 220. Meanwhile, the area between the marker 420 and the marker 430 corresponds to a low index layer 230. And, the marker 420 corresponds to the interface 275 between those two layers 220, 230.

Further, the plot 400 can provide an exemplary material profile of the system 200, where the vertical axis of FIG. 4 represents material composition rather than refractive index.

As will be discussed in further detail below, the refractive index profile 400 of FIG. 4 can have additional structures that provides the illustrated smooth curves. For example, the individual layers transition layers, while having individual abrupt material and refractive index changes, may create an aggregate smoothing effect as shown in FIG. 4. Thus, light propagating in the vicinity of one of the interfaces 275 can experience the transition layers 175 as a relatively smooth transition or ramp. In other words, the smooth plot 400 can provide a representation of refractive index from the perspective of light propagating in the vicinity of an interface 275 that has accompanying transition layers 175.

Figure 5:
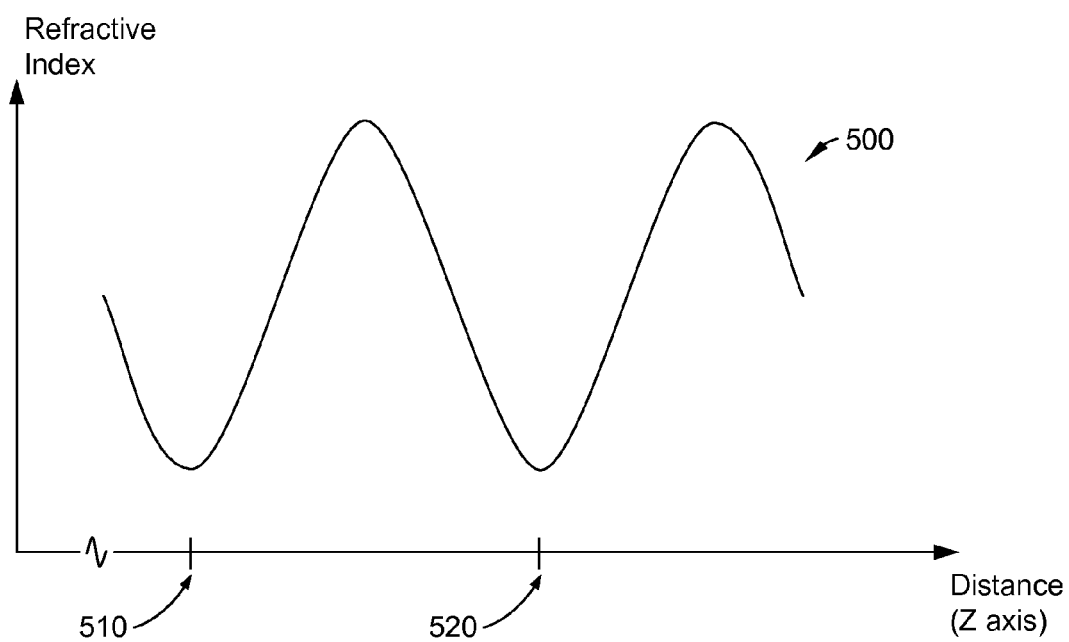
FIG. 5 illustrates a high-level plot of refractive index of a plurality of thin film layers, generally resembling a sinusoidal waveform, in accordance with an exemplary embodiment of the present invention.

Turning now to FIG. 5, this figure illustrates a high-level plot 500 of refractive index of a plurality of exemplary thin film layers 220, 230, 175, generally resembling a sinusoidal waveform, according to an embodiment of the present invention. The markers 510 and 520 indicate a full cycle of periodicity of the plot 500 and the material structure that the plot 500 characterizes. In addition to being representative of refractive index (as labeled on the vertical axis of the plot 500), the plot 500 can be representative of a periodic variation of material composition.

In one exemplary embodiment, the plot 500 can be the result of having transition layers 175 disposed essentially throughout adjoining high index and low index layers 220, 230. For example, the system 200 of FIG. 2 can be adapted to provide the refractive index profile 500 by distributing transition layers 175 throughout layers 220, 230, rather than concentrating the transition layers 175 at the interfaces 275.

In one exemplary embodiment, the sinusoidal plot (or some similar oscillating profile or periodic waveform) can provide a grating function. For example, imparted with the sinusoidal variation via transition layers 175, a stack of thin film layers 220, 230 can be or can comprise an optical transmission or refection grating.

Figure 6:
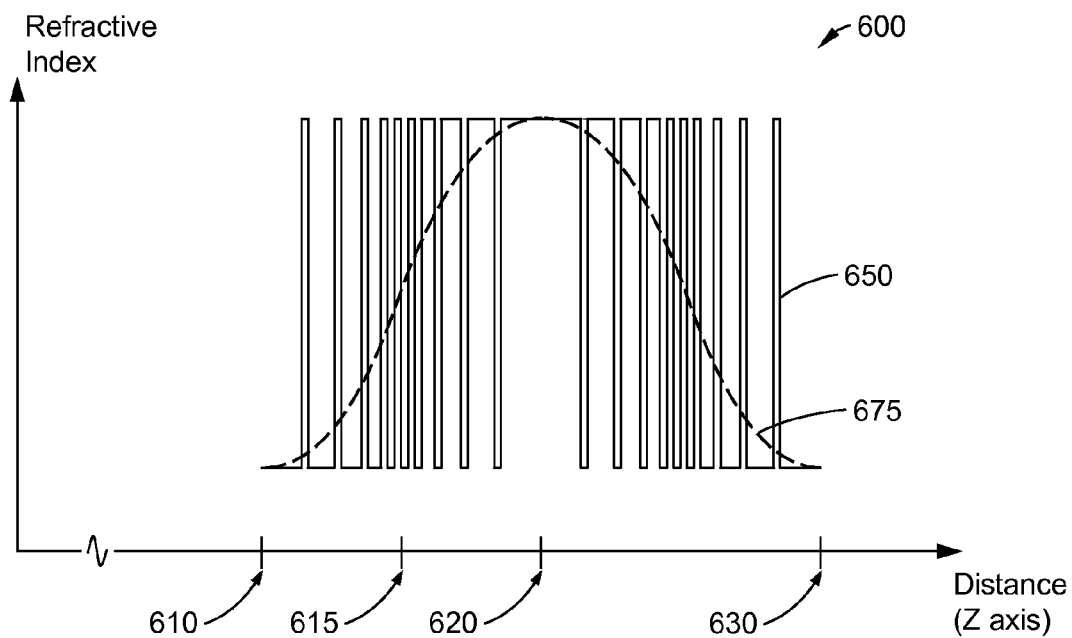
FIG. 6 illustrates a refractive index plot of a plurality of thin film layers, wherein a net or average refractive index profile overlays a detail plot that depicts the refractive index pattern of a series of transition or transitional thin film layers disposed at an interface between major thin film layers, in accordance with an exemplary embodiment of the present invention.

Turning now to FIG. 6, this figure illustrates a refractive index plot 600 of a plurality of thin film layers 175, 220, 230, wherein a net or average refractive index profile 675 overlays a detail plot 650 that depicts the refractive index pattern of a series of exemplary transition or transitional thin film layers 175 disposed at an interface 275 between major thin film layers 220, 230, according to an embodiment of the present invention.

In one exemplary embodiment, the plot 600 describes in further detail the physical structure that underlies the plot 500 of FIG. 5, discussed above. That is, the thin films 175, 220, 230 that the plot 600 describes can be similar in form, function, or composition, or can share some other attribute, to the thin film embodiment of the plot 500.

In one exemplary embodiment, the profile or plot 675 describes refractive index from the perspective of light 125 propagating through the thin film structure 175, 220, 230. Meanwhile, the profile or plot 650 describes refractive index on a nano scale, for example as might be resolved by a very high resolution scanning electron microscope (SEM) or some other material analyzing system with nano-scale resolution. Alternatively, the profile 650 can describe theoretical refractive index variations that may be too small to be analyzed with typical analysis instruments.

In one exemplary embodiment of the present invention, the profile 675 can be viewed as an averaged or a filtered version of the profile 650. The profile 650 can describe the physical characteristics or the actual physical dimensions of the thin film structure 175, 220, 230. Meanwhile, the profile 675 can describe the net, resultant optical characteristics or the actual optical performance of that structure, 220, 230.

In one exemplary embodiment, the transition layers 175 that the profile 650 describes are sufficiently thin, for example a few atoms thick, such that light 125 passing there through may interact with each individual layer 175 as if those individual layers 175 were smoothly varying rather than as bulk material. Thus, the light 125 interacting with the individual transition layers 175 may interact in a manner distinct from the manner in which light interacts with a bulk material that has dimensions on the order of the wavelength of light.

The portion of the profiles 650, 675 above the marker 610 (on the horizontal axis) describes an exemplary low index layer 230. Similarly, the portion of the profiles 650, 675 above the marker 630 describes another exemplary low index layer 230. Thus, the centers of the layers 220 typically lie directly over the respective markers 610, 630. Meanwhile, the portion of the profiles 650, 675 above the marker 620 describes an exemplary high index layer 220, with the center of the layer 230 typically lying directly over the marker 620.

The portion of the profiles 650, 675 between the marker 610 and the marker 620 (over the marker 615) describes a transition between a center of a low refractive index layer 230 and a center of a high refractive index layer 220. Similarly, the portion of the profiles 650, 675 between the marker 620 and the marker 630 describes a transition between a center of a high refractive index layer 220 and a center of a low refractive index layer 230. As illustrated, the plot 600 exhibits exemplary symmetry of the profiles 650, 675 (and the associated transition layers 175) around the layer centers.

Between the center of the low refractive index layer 230 (directly over the marker 610) and the midpoint of the transition (directly over the marker 615), transition layers that have high refractive index are disposed in that layer 230. As illustrated, those high index transition layers have essentially uniform thickness. As further illustrated, the separation between those high index transition layers decreases moving from the center point 610 of the low index layer 230 towards the transition midpoint 615.

Between the midpoint of the transition (directly over the marker 615) and the center 610 of the high refractive index layer 220 transition layers that have low refractive index are disposed in that high index layer 220. As illustrated, those low index transition layers have essentially uniform thickness. As further illustrated, the separations between those individual low index transition layers increases in the dimension moving from the transition midpoint 615 towards the center point 620 of the high index layer 220.

As an alternative to viewing the transition layers as being disposed in or added to high and low index primary layers 220, 230, the system of layers 175, 220, 230 that FIG. 6 describes can be viewed as a series of layers of discrete or binary refractive index (and/or material composition) that function in a collaborative manner. The thicknesses of and separation between the individual layers of that series, while being individual abrupt, present the light 125 with a gradual change in refractive index.

The illustrated portions of the profiles 650, 675, between the marker 610 and the marker 630 represent a full cycle of low index and high index layers 220, 230. While a single cycle is illustrated, the cycle may repeat, for example as a stack of alternating refractive index layers.

In many situations, utility can result from using high index layers 220 that have a different thickness than the low index layers 230. More generally, the high index layers 230 and the low index layers 220 can have respective optical, geometric, or physical thicknesses that may be the same, similar, essentially equal (for example within manufacturing tolerance), or purposefully different.

Figure 7:
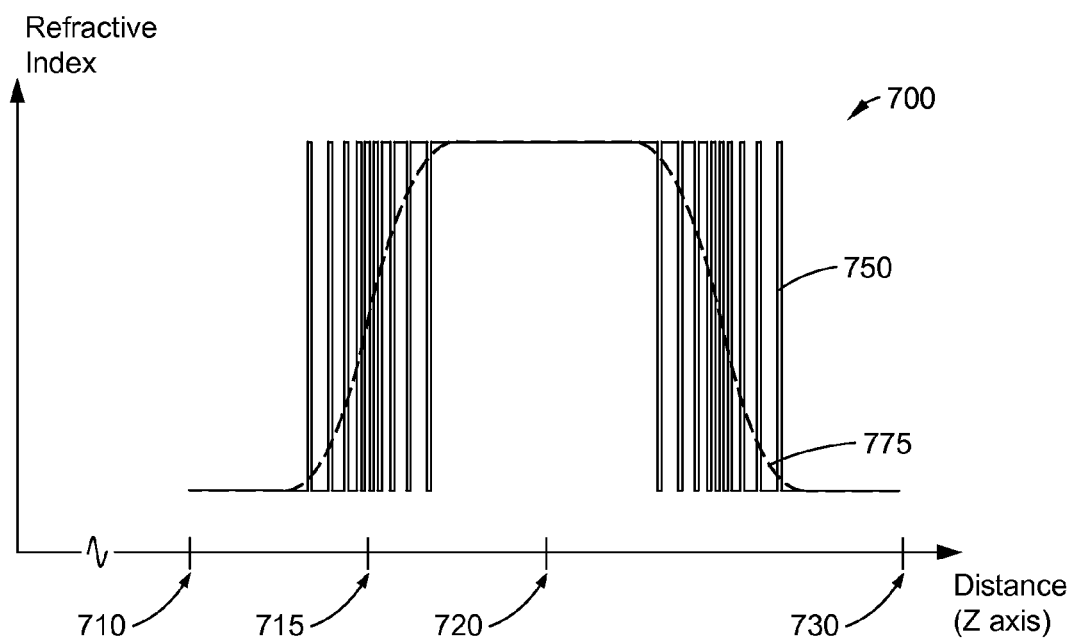
FIG. 7 illustrates a refractive index plot of a plurality of thin film layers, wherein a net or average refractive index profile overlays a detail plot that depicts the refractive index pattern of a series of transition or transitional thin film layers disposed at an interface between major thin film layers, in accordance with an exemplary embodiment of the present invention.

Turning now to FIG. 7, this figure illustrates a refractive index plot 700 of a plurality of thin film layers 175, 220, 230, wherein a net or average refractive index profile 775 overlays a detail plot 750 that depicts the refractive index pattern of a series of exemplary transition or transitional thin film layers 175 disposed at an interface 275 between major thin film layers 220, 230, according to an embodiment of the present invention. As discussed above, the profile 775 can describe refractive index from the perspective of the light 125, while the profile 750 can describe refractive index on the nanoscale. Thus, a point on the profile 750 might describe the refractive index exhibited by a slab of bulk material having a composition that corresponded to that point. In other words, the plot 750 can describe the measurable refractive index of a transition layer, if that transition layer was ten or more wavelengths thick rather than extremely thin. Meanwhile, the profile 875 can describe the composite, average, or systemic refractive index.

Whereas the exemplary embodiment of FIG. 6, discussed above, has transition layers 175 distributed across, or essentially throughout, the high and low index layers 220, 230, the exemplary embodiment of FIG. 6 has those transition layers 175 concentrated at the midpoint 715 between the center 710 of the low index layer 230 and the center 720 of the high index layer 220. Accordingly, the profiles 750, 775 have flat sections at the layer centers 710, 720, 730.

The thin film system embodiment of FIG. 7 can be viewed has having feathered, sloped, or beveled transitions between the adjoining layers 220, 230. Moreover, the plot 700 can describe a device that provides the refractive index profile 400 of FIG. 4, discussed above. That is, the exemplary embodiment of FIG. 7 can be similar to or can correspond to the exemplary embodiment of FIG. 4, discussed above.

Figure 8:
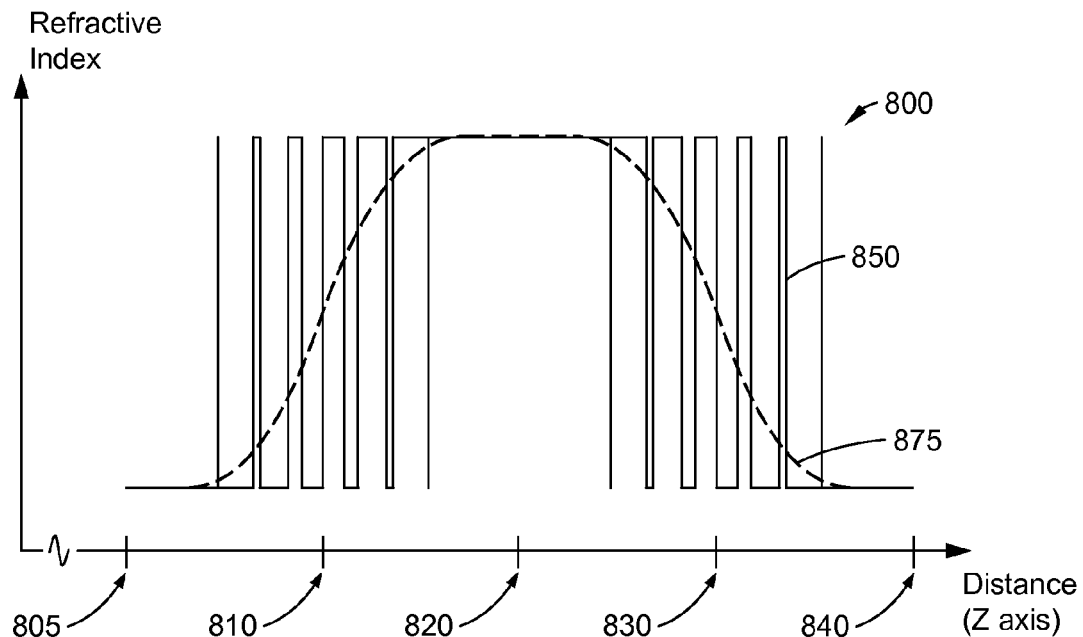
FIG. 8 illustrates a refractive index plot of a plurality of thin film layers, wherein a net or average refractive index profile overlays a detail plot that depicts the refractive index pattern of a series of transition or transitional thin film layers disposed at an interface between major thin film layers, in accordance with an exemplary embodiment of the present invention.

Turning now to FIG. 8, this figure illustrates a refractive index plot 800 of a plurality of thin film layers 175, 220, 230, wherein a net or average refractive index profile 875 overlays a detail plot 875 that depicts the refractive index pattern of a series of exemplary transition or transitional thin film layers 175 disposed at an interface 275 between major thin film layers 220, 230, according to an embodiment of the present invention.

In the region between the marker 805 and the marker 820, the plot 800 describes a transition between a low index layer 230 and a high index layer 220. In the region between the marker 820 and the marker 840, the plot 800 describes a transition between a high index layer 220 and a low index layer 230. In some applications or embodiments, a single transition will be appropriate. Benefit may result from having a transition from a section of high index material that is not necessarily a thin film, to a section of low index material that is not necessarily a thin film.

For example, a core of an optical waveguide might comprise the high index region 820, and a material surrounding the core, such as a cladding, might comprise the low index region 805. In this situation, the transition region 805 can be the boundary or the area between the core and the cladding. In this manner, the transition layers 175 can support an optical effect that is similar to a gradient index fiber or a gradient index lens.

In one exemplary embodiment, the high index material may have a different phase than the low index material. For example, the high index material could be a waveguide, a piece of glass, a semiconductor, or a piece of plastic, which the low index material could be water, a liquid, or a gas, such as air. In this situation, the transition layers may comprise regions of the high index material that lead up to the low index material. Thus, the transition layers may function as a lead in, an antireflective structure, or even a high index structure.

In one exemplary embodiment, the transition layers (or another thin film structure) may provide a different function or result according to the material that is in contact with the high index section at any particular time. That result can comprise a change in color, reflectivity, polarization, transmission, absorption, phase, etc. For example, a polymer, monofilament, or plastic fishing line can be coated with transition layers or another film. The coating can be applied to the line after it is formed. Alternatively, the polymer line and the coating can be drawn or extruded from a nozzle or spinneret, for example in one pass.

The coating can be highly reflective when the fishing line is in an air environment. Meanwhile, when the coated fishing line is in contact with water, the reflection can disappear or be suppressed. That is, a transition layer or another coating can provide high reflectivity or visibility for the portion of the line that is above a lake and can provide low reflectivity, low visibility, or high transparency for the portion of the line that is in the lake. Moreover, the perceived color of the line can change based on whether it is immersed in water. In this manner, the fishing line can be visible or colorful to the fisherman and essentially invisible to the fish.

Referring now to FIG. 8, the refractive indices of the transition layers 175 are modulated in a manner that manages the light 125 that is propagating in the vicinity of the interface 275 or boundary between the high index layer 220 and the low index layer 230. Moreover, the transition layers 175 can provide a lead-in, a tapered transition, a harmonizing effect, or a soft surface to the light 125. In one exemplary embodiment, the transition layers 175 cushion the light waves or the photons as they move between the high index layer 220 and the low index layer 230. In one exemplary embodiment, the transition layers 175 can refract the light incident thereon.

As illustrated, at least some of the individual layers of the transition layers 175 can be uniformly spaced with respect to one another. That is, some or essentially all of individual layers above the marker 810 can be equally spaced or disposed as if on a grid. The distance (geometric or optical) between the first transition layer and the second transition layer can be essentially equal to the distance between the second transition layer and the third transition layer, etc. The thicknesses of each of those individual layers of the series can vary gradually so that the net amount of material is graduated in a discrete manner across the interface 175, 810. That is, the transition layers 175 can comprise a system of progressively thicker and/or thinner layers. And, the transition layers 175 can comprise a system of successively thicker and/or thinner layers. Those individual layers can be substantially thinner than the wavelength of managed light 125 that is incident thereon. In one exemplary embodiment, those individual layers can be substantially thinner than one-fourth the wavelength of the managed light 125.

An equation that describes the progressive change in thickness can be hyperbolic, sinusoidal, exponential, linear, or decaying exponential, for example. Rather than conforming to a particular equation, the progressive change can follow a computer-generated specification, profile, or equation. For example, an optical simulation software program can generate a set of coordinates or target values that a deposition process can meet via intermittently depositing two or more materials.

The individual transition layers can exhibit symmetry on one side of the interface 275, 810 relative to the other side of the interface 275, 810. Alternatively, the transition layers 175 can be asymmetric with respect to the interface 275, 810. In one exemplary embodiment, the transition layers 175 associated with the marker 810 can be different (in number, thickness, geometry, functionality, etc.) than the transition layers 175 associated with the marker 830.

The optical system that the plot 800 describes can also be viewed as a low refractive index material into which high refractive index layers have been disposed. Starting at the left side of the plot 800, those high index layers are progressively thicker towards the marker 820. Thus, the amount of high index material increases gradually in discrete steps from the marker 805 to the marker 820 and then decreases from the marker 820 to the marker 840. The relative amounts of the high index material and the low index material can be viewed as having a gradient, a gradual slope, or a graduated character. Moreover, the transition layers 175 can impart the system with a blended composition of optical materials without necessarily mixing those materials in a uniform or homogeneous manner. Thus, a system of extremely thin layers can behave optically like a system of mixed optical materials.

Figure 9:
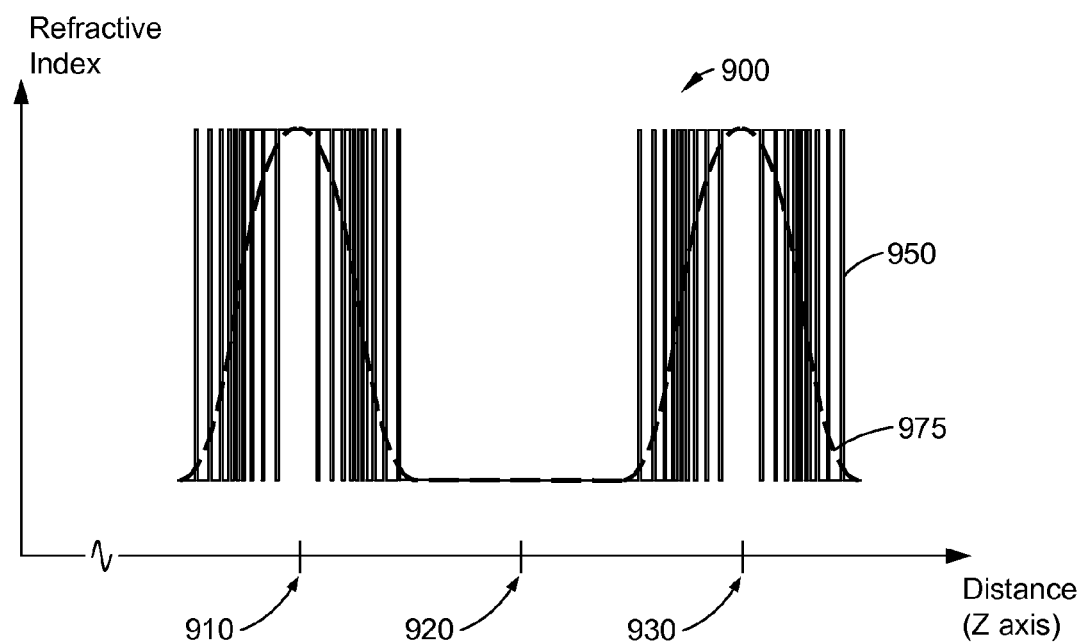
FIG. 9 illustrates a refractive index plot of a plurality of thin film layers, wherein a net or average refractive index profile overlays a detail plot that depicts the refractive index pattern of a series of transition or transitional thin film layers disposed at an interface between major thin film layers, in accordance with an exemplary embodiment of the present invention.

Turning now to FIG. 9, this figure illustrates a refractive index plot 900 of a plurality of thin film layers 175, 220, 230, wherein a net or average refractive index profile 975 overlays a detail plot 950 that depicts the refractive index pattern of a series of exemplary transition or transitional thin film layers 175 disposed at an interface 275 between major thin film layers 220, 230, according to an embodiment of the present invention. In an exemplary embodiment, the profile 975 can be characterized as the composite effect of the individual transitional structures that the plot 950 details.

The plot 900 generally describes a system having two section of high refractive index material, respectively associated with the markers 910 and 930, that bracket a section of low refractive index material, associated with the marker 920. The transition layers 175 provide a controlled material transition between the high refractive index materials and the low refractive index materials. As illustrated, the low index section is thicker than the high index sections. In one exemplary embodiment, the low index section, associated with the marker 920 emits light or otherwise comprises an active light source. In one exemplary embodiment, at least one of the high index sections, associated with the markers 910, 930, emits light or otherwise comprises an active light source. In one exemplary embodiment, each of the sections 910, 920, 930 functionally manages at least one of light and electrons.

Cross sectional illustrations of exemplary systems of transition layers will be discussed below with reference to FIGS. 10-14. The exemplary embodiments of FIGS. 10-14 can generally correspond to the exemplary embodiments of FIGS. 6-9. That is, FIGS. 10-14 provide additional information, in the form of representative cross sectional views, about systems that FIGS. 6-9 describe graphically, in the form of plots or profiles.

Figure 10:
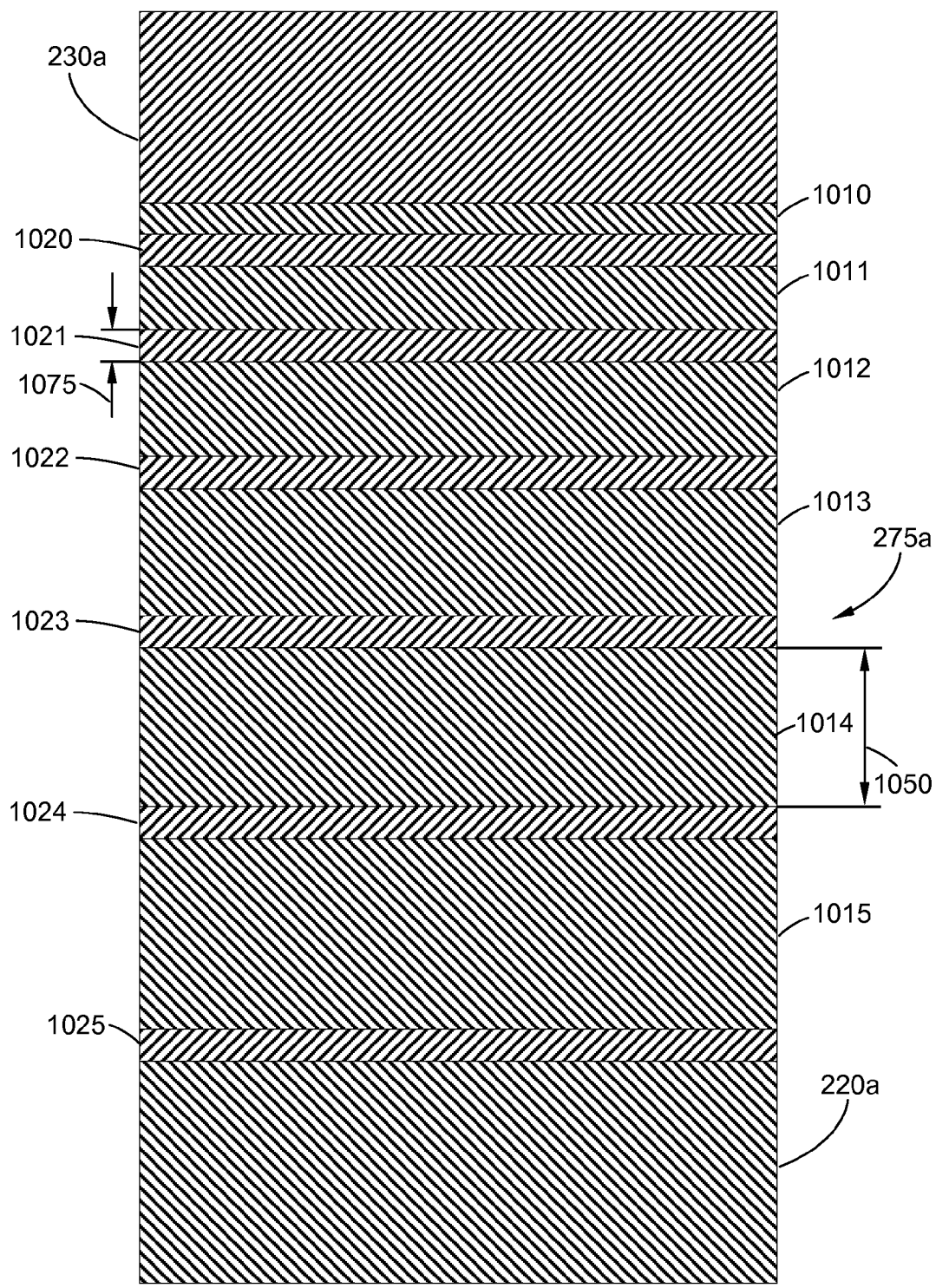
FIG. 10 illustrates a cross sectional profile of a plurality of thin film layers that manage light at an interface between two optical material sections in accordance with an exemplary embodiment of the present invention.

Turning now to FIG. 10, this figure illustrates a cross sectional profile of an exemplary plurality of thin film layers 1000 that manage light 125 at an interface 275/275a between two optical material sections 220a, 230a according to an embodiment of the present invention. The two optical material sections 220a, 230a can be exemplary embodiment of the layers 220, 230 discussed above. Accordingly, the system 1000 illustrates an exemplary embodiment of plurality of transition layers 175 as discussed above. Moreover, the system 1000 can correspond to one of the plots 600, 700, 800, 900 discussed above.

In an exemplary embodiment of the system 1000, the layers 220a, 1015, 1014, 1013, 1012, 1011, 1010 comprise material having relatively high refractive index, and the layers 230a, 1020, 1021, 1022, 1023, 1024, 1025 comprise material having relatively low refractive index. In one exemplary embodiment, the layers 220a, 1015, 1014, 1013, 1012, 1011, 1010 have a common composition. In one exemplary embodiment, the layers 1015, 1014, 1013, 1012, 1011, 1010 have a common composition that is distinct from the composition of the layer 220a. In one exemplary embodiment, the layers 230a, 1020, 1021, 1022, 1023, 1024 have a common composition. In one exemplary embodiment, the layers 1020, 1021, 1022, 1023, 1024 have a common composition that is distinct from the composition of the layer 230a. The materials of each of the layers 1020, 1021, 1022, 1023, 1024 and the layers 1015, 1014, 1013, 1012, 1011, 1010 are typically, but not necessarily completely, homogeneous or have essentially uniform internal structures.

In the illustrated exemplary embodiment, the layers 1025, 1024, 1023, 1022, 1021, 1020 have similar or essentially the same thickness 1075. The layers 1015, 1014, 1013, 1012, 1011, 1010 have progressively less thickness 1050. That is, the layers 1015, 1014, 1013, 1012, 1011, 1010 decrease in thickness from the layer 220a towards the layer 230a. The decrease can be linear, decaying exponential, exponential, geometric, etc. or follow some other equation or computer-generated formula or pattern.

In one exemplary embodiment, the dimension 1021 can be less than 10 nanometers. In one exemplary embodiment, the dimension 1021 can be in a range of 10 to 25 nanometers. In one exemplary embodiment, the dimension 1021 can be in a range of 1 to 5 nanometers. In one exemplary embodiment, the dimension 1021 can be approximately 50 to 100 nanometers.

In one exemplary embodiment, the dimension 1021 can be less than approximately one-tenth the wavelength of the light 125 that the system 1000 is operative to manage. In one exemplary embodiment, the dimension 1021 can be less than approximately one-fiftieth the wavelength of the light 125 that the system 1000 is operative to manage. In one exemplary embodiment, the dimension 1021 can be less than approximately one-fourth the wavelength of the light 125 that the system 1000 is operative to manage. In one exemplary embodiment, the dimension 1021 can be less than approximately one-twentieth the wavelength of the light 125 that the system 1000 is operative to manage. In one exemplary embodiment, the dimension 1021 can be less than approximately one percent of the wavelength of the light 125 that the system 1000 is operative to manage. In one exemplary embodiment, the dimension 1021 of at least one of the layers 1025, 1024, 1023, 1022, 1021, 1020 can be less than approximately 0.1% or 0.01% of the wavelength of the light 125 that the system 1000 manages.

In one exemplary embodiment, the dimensions 1050 of the layers 1015, 1014, 1013, 1012, 1011, 1010 can progress from about 1000 nanometers to about 5 nanometers. In one exemplary embodiment, the dimensions 1050 of the layers 1015, 1014, 1013, 1012, 1011, 1010 can progress from about 100 nanometers to about 1 nanometers. In one exemplary embodiment, the dimensions 1050 of the layers 1015, 1014, 1013, 1012, 1011, 1010 can progress from about 500 nanometers to about 3 nanometers. In one exemplary embodiment, the dimensions 1050 of the layers 1015, 1014, 1013, 1012, 1011, 1010 can progress from about 100 nanometers to about 2 nanometers.

In one exemplary embodiment, the dimensions 1050 of the layers 1015, 1014, 1013, 1012, 1011, 1010 can progress from about one-fourth to about one-hundredth of the wavelength of the light 125 that the system 1000 is operative to manage. In one exemplary embodiment, the dimensions 1050 of the layers 1015, 1014, 1013, 1012, 1011, 1010 can progress from about one-tenth to about one-hundredth of the wavelength of the light 125 that the system 1000 is operative to manage. In one exemplary embodiment, the dimensions 1050 of the layers 1015, 1014, 1013, 1012, 1011, 1010 can progress from about one-tenth to about one-thousandth of the wavelength of the light 125 that the system 1000 is operative to manage. In one exemplary embodiment, the dimensions 1050 of the layers 1015, 1014, 1013, 1012, 1011, 1010 can progress from about one-tenth to about one-thousandth of the wavelength of the light 125 that the system 1000 is operative to manage.

While the illustrated number of layers of the exemplary system 1000 is relatively small, other embodiments may comprise many more layers, for example twenty-five, fifty, one hundred, one thousand, or more.

Figure 11:
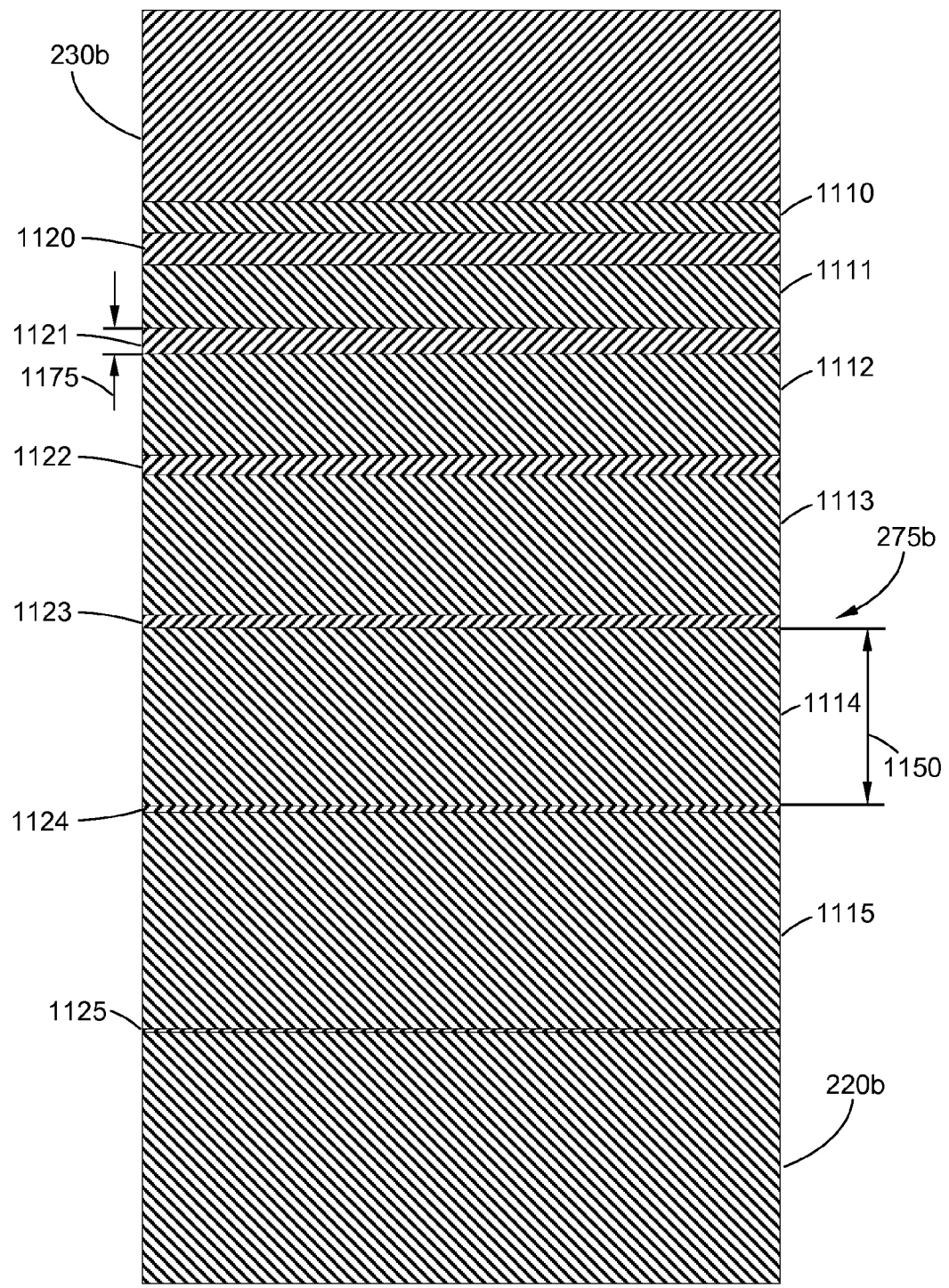
FIG. 11 illustrates a cross sectional profile of a plurality of thin film layers that manage light at an interface between two optical material sections in accordance with an exemplary embodiment of the present invention.

Turning now to FIG. 11, this figure illustrates a cross sectional profile of an exemplary plurality of thin film layers 1100 that manage light 125 at an interface 275/275b between two optical material sections 220b, 230b according to an embodiment of the present invention. Accordingly, FIG. 11 illustrates an exemplary embodiment of a plurality of transition layers 175, in the form of the system 1100. The material sections 220b, 230b can be exemplary embodiments of the materials 220, 230 discussed above.

The layers 1125, 1124, 1123, 1122, 1121, 1120 each comprises material having relatively low refractive index, for example as measured in bulk form. Meanwhile, the interleaved or interspersed layers 1115, 1114, 1113, 1112, 1111, 1110 have contrasting refractive indices, for example relatively high refractive indices.

From the material section or layer 220b towards the material section or layer 230b, the layers 1125, 1124, 1123, 1122, 1121, 1120 have progressively increasing thicknesses 1121. From the layer 230b towards the material section 220b, the layers 1110, 1111, 1112, 1113, 1114, 1115 have progressively increasingly thicknesses 1150. Thus, the average refractive index of the system 1100 gradually changes between the layer 220b and the layer 230b. The individual layers 1125, 1124, 1123, 1122, 1121, 1120, 1110, 1111, 1112, 1113, 1114, 1115 that contribute to the refractive index profile can be viewed as providing a terrace or a lattice of refractive index and/or composition.

As discussed above with respect to FIG. 10, the layers 1125, 1124, 1123, 1122, 1121, 1120, 1110, 1111, 1112, 1113, 1114, 1115 typically have nano-scale features and dimensions 1121, 1114.

Figure 12:
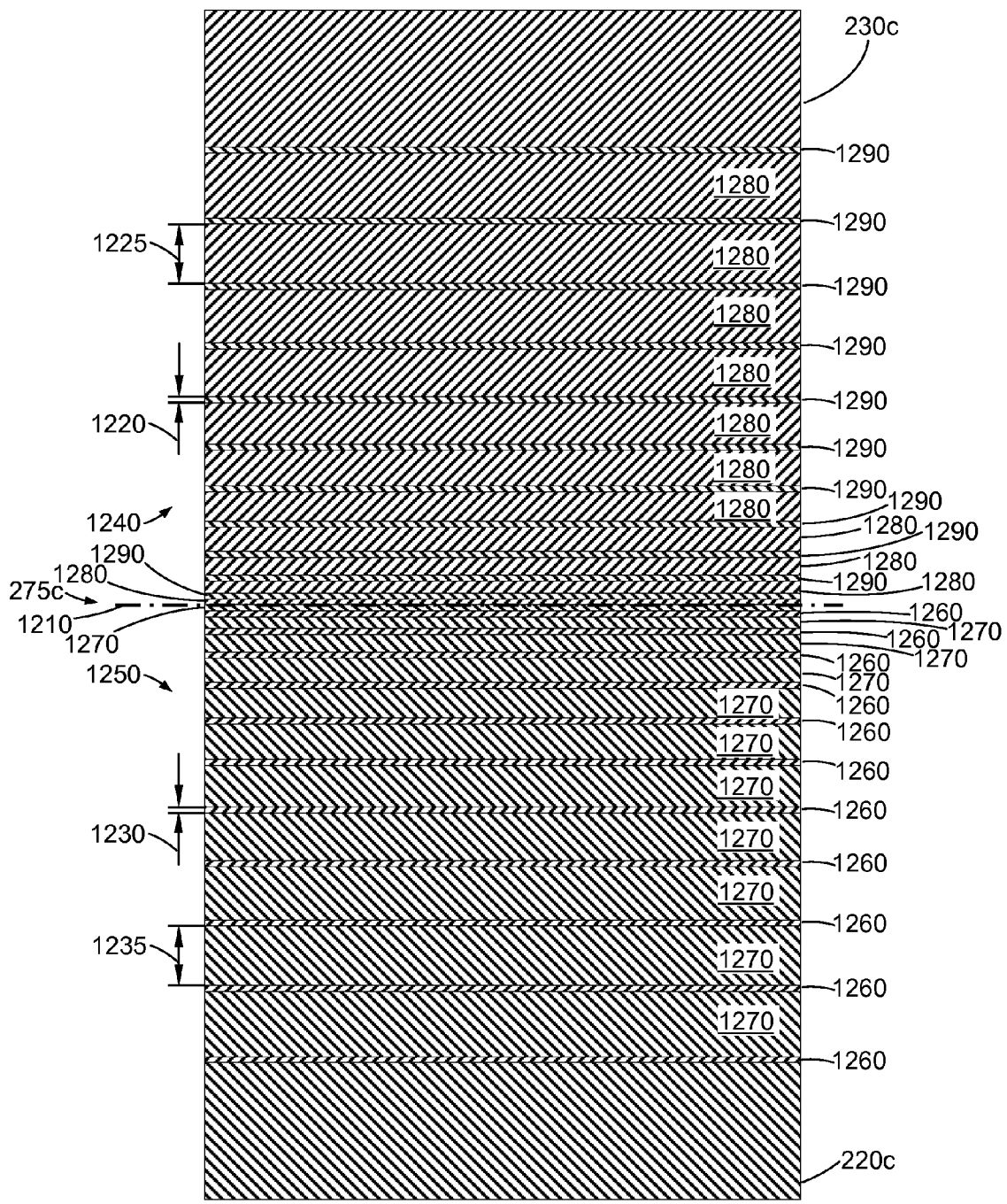
FIG. 12 illustrates a cross sectional profile of a plurality of thin film layers that manage light at an interface between two optical material sections in accordance with an exemplary embodiment of the present invention.

Turning now to FIG. 12, this figure illustrates a cross sectional profile of an exemplary plurality of thin film layers 1200 that manage light 125 at an interface 275c between two optical material sections 230c, 220c in accordance with an exemplary embodiment of the present invention. The interface 275c provides an exemplary embodiment of the interface 275 that is discussed above. The illustrated material sections 220c, 230c provide exemplary embodiments of the materials 220, 230 that are discussed above.

The layers 1260 and the layers 1280 have essentially the same material composition as the layer 230c. And, the layers 1270 and the layers 1290 have essentially the same material composition as the layer 220c. Each of the layers 1260 have similar thicknesses 1230, and each of the layers 1290 have similar thicknesses 1220. As discussed above, those thickness dimensions 1230, 1220 are typically very small, even on the scale of light. In one exemplary embodiment, the dimensions 1230, 1220 are small enough to avoid any individual layer 1290, 1270 creating substantial optical interference impacting the operable spectral region of the system 1200.

The axis 1210 is associated with or is aligned to the interface 275c and illustrates an approximate midpoint or centerline of the transition layer system 1200. From the section 220c to the axis 275c, the respective thicknesses 1235 of the series of the layers 1270, which are interleaved between the layers 1260, successively decreases. From the section 230c to the axis 275c, the respective thicknesses 1225 of the series of the layers 1280, which are interleaved between the layers 1290, successively decreases.

The varying thicknesses 1225 of the layers 1280 can be similar to the varying thicknesses 1235 of the layers 1270. Accordingly, the system 1200 can have a type of symmetry on the upper side 1240 of the reference line 1210 relative to the lower side 1250. The two variations can serve to provide a balanced lead-in to the axis 1210 and a corresponding lead-out from the axis 1210.

Figure 13:
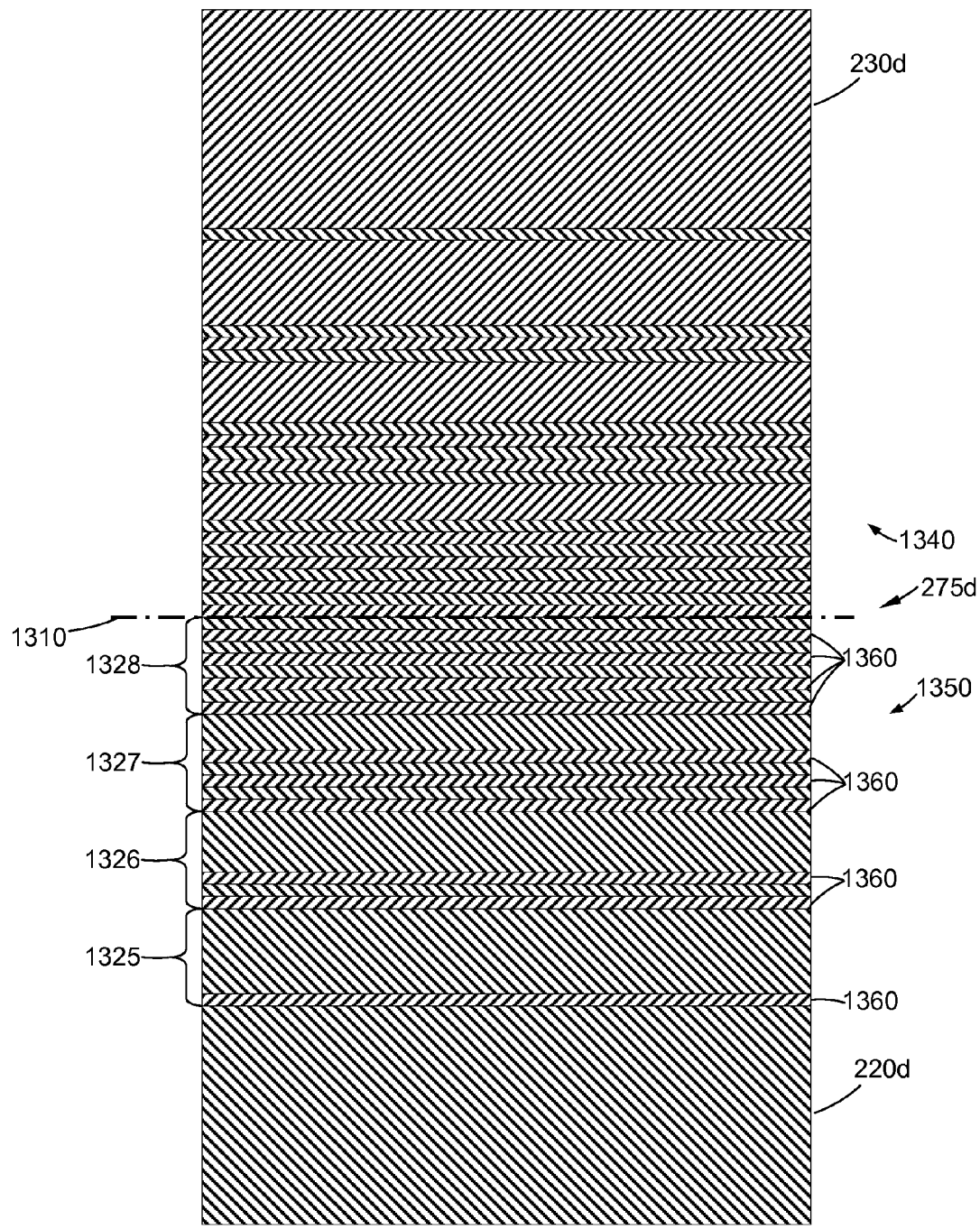
FIG. 13 illustrates a cross sectional profile of a plurality of thin film layers that manage light at an interface between two optical material sections in accordance with an exemplary embodiment of the present invention.

Turning now to FIG. 13, this figure illustrates a cross sectional profile of an exemplary plurality of thin film layers 1300 that manage light 125 at an interface 275d between two optical material sections 220d, 230d according to an embodiment of the present invention. The interface 275d and the optical material sections 220d, 230d of FIG. 13 can respectively be exemplary embodiments of the interface 275 and the optical materials sections 220, 230 discussed above.

The system 1300 comprises a section 1340 above the reference line 1310, which is shown at a nominal or arbitrary location of the material interface 275d and a section 1350 below the reference line 1310. Geometrically, the sections 1340, 1350 can generally be symmetrical with respect to one another (with appropriate material substitutions). Accordingly, the lower section 1350 is labeled with reference numerals and will now be discussed.

The section 1350 comprises a series of layers 1360 that lead up to (or form part of) the interface 275d, providing a transition from the material section 220d towards the material section 230d. The layers 1360 are typically made of the same material as the section 230d. The material between each of the layers 1360 typically has the same composition as the material of the section 220d.

The density or number of the layers 1360 increases towards the line 1310. That is, there are a greater number of layers towards the interface line 1310 than towards the material section 220d. More specifically, in the illustrated exemplary embodiment, the section 1325 comprises one of the layers 1360. The section 1326 comprises two of the layers 1360. The section 1327 comprises three of the layers 1360. The section 1328 comprises four of the layers 1360. The sections 1325, 1326, 1327, 1328 may have similar optical or geometric thicknesses, for example each being 5, 10, 20, 30, 40, or 50 nanometers thick, or in a range thereof. The layers 1360 can have a thickness of about 1, 2, 3, 5, 7, 10, or 15 nanometers, or in a range thereof. These dimensions can correspond to managing light 125 of about 500, 750, 1000, 1250, or 1550 nanometers and can be linearly scaled up or down for other wavelengths, for example.

Figure 14:
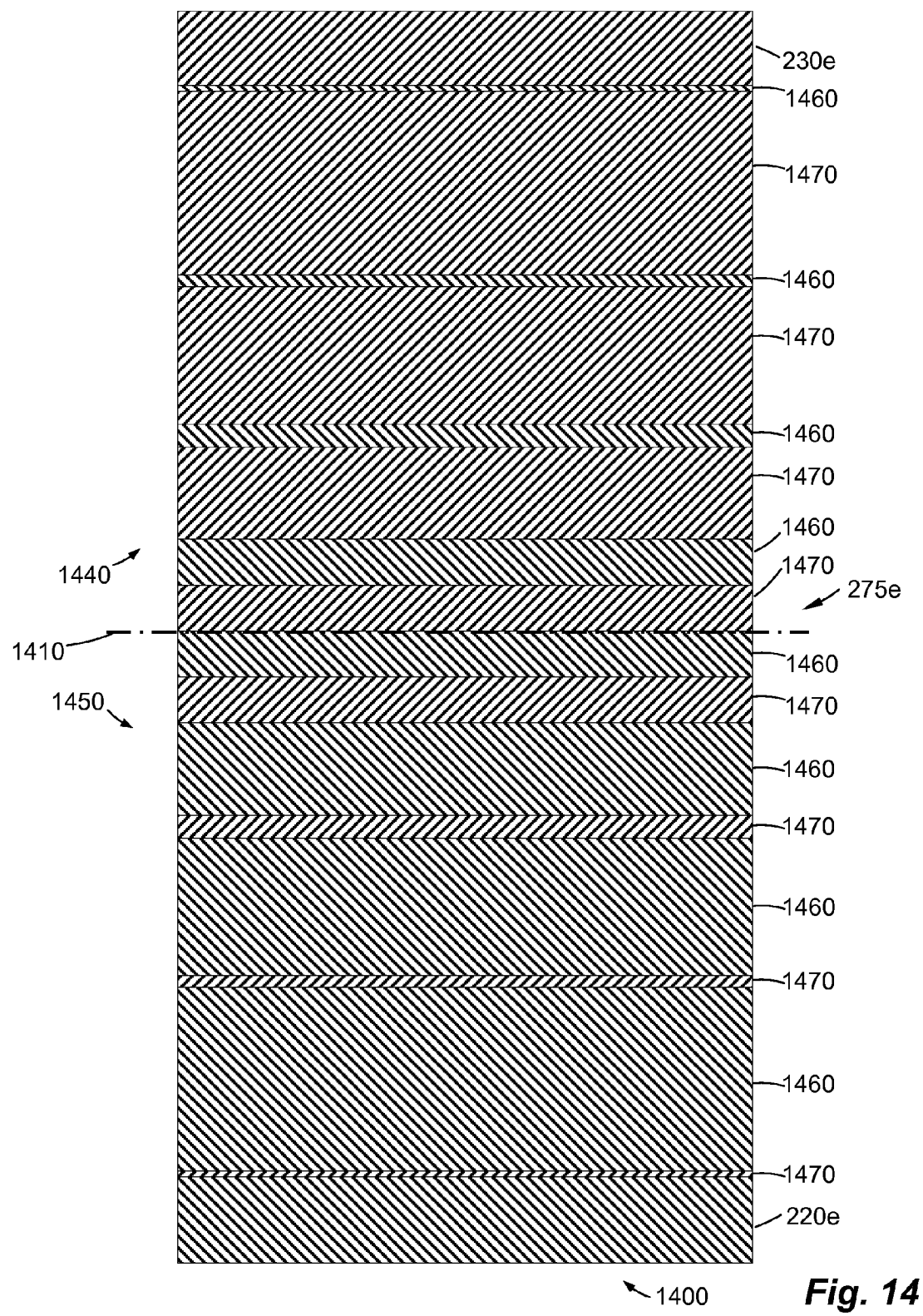
FIG. 14 illustrates a cross sectional profile of a plurality of thin film layers that manage light at an interface between two optical material sections in accordance with an exemplary embodiment of the present invention.

Turning now to FIG. 14, this figure illustrates a cross sectional profile of an exemplary plurality of thin film layers 1400 that manage light 125 at an interface 275e between two optical material sections 220e, 230e according to an embodiment of the present invention. The interface 275e and the material sections 220e, 230e can comprise respective exemplary embodiments of the interface 275 and the material sections 220, 230 discussed above.

Between the high index section 220e and the low index section 230e are disposed an arrangement of high index layers 1460, and low index layers 1470 that are operative to manage light transmission in the vicinity of the interface 275e. The imaginary line 1410 (not physically present in a operating device) represents a somewhat arbitrary location of the interface 275e, for illustrative purposes. The section 1440 and the section 1450 exhibit symmetry about the line 1410, with a between the sections 1440, 1450 distinction being that the compositions of the layers are reversed or swapped, as shown in the cross sectional view of FIG. 14.

The layers 1470 progressively increase in thickness from the material section 220e towards the line 1410, and further increase in thickness towards the material section 230e. Meanwhile, the layers 1460 progressively decrease in thickness from the material section 220e towards the line 1410, and further decrease in thickness towards the material section 230e.

In one exemplary embodiment, the successive decrease in the sizes of the layers 1460 from the material section 230e to the material section 220e parallels or directly corresponds to the successive decrease in the sizes of the layers 1470 from the material section 220e to the material section 230e. Those layers 1460, 1470 can vary across the interface 275e from about one-fourth to about one-hundredth or about one-thousandth the center wavelength of the managed light 125. In one exemplary embodiment, the layers 1460, 1470 can vary from about 300 nanometers to about 10 nanometers, or from about 250 nanometers to about 5 nanometers, between the sections 220e and 230e. In one exemplary embodiment, the layers 1460, 1470 can vary across the system 1400 from about one atom in thickness to a thickness that behaves similar to bulk material. Moreover, the layers can have a thickness of atoms that varies from about 2 to about 100, from about 5 to about 1000, from about 10 to about 10,000, from about 50 to about 100,000, from about 1-10 to about 1,000-100,000-1,000,000, or in some range thereof, for example. In various exemplary embodiments, those variations can occur over a series of 25, 50, 100, 250, or 500 of the layers 1460, 1470.

An exemplary process for fabricating an optical system comprising a structure for managing light 125 at an optical interface 275 and an exemplary process for managing light 125 via such a fabricated structure will be discussed below with reference to FIGS. 15 and 16. In certain embodiments, one or more of those processes, or other processes disclosed or taught herein, may comprise or involve computer programs, computer-implemented steps, or software.

Accordingly, some exemplary embodiments the present invention can include multiple computer programs embodying certain functions described herein and illustrated in the examples, functional block diagrams, and appended flow charts. However, it should be apparent that there could be many different ways of implementing aspects of the present invention in computer programming, and the invention should not be construed as limited to any one set of computer program instructions. Further, a skilled programmer would be able to write such computer programs without difficulty based on the exemplary functional block diagrams, flow charts, and associated description in the application text, for example.

Therefore, disclosure of a particular set of program code instructions is not considered necessary for an adequate understanding of how to make and use the present invention. The inventive functionality of any programming aspects of the present invention will be explained in more detail in the following description in conjunction with the remaining figures illustrating the functions and program flow and processes.

Certain steps in the processes described below must naturally precede others for the present invention to function as described. However, the present invention is not limited to the order of the steps described if such order or sequence does not alter the functionality of the present invention. That is, it is recognized that some steps may be performed before or after other steps or in parallel with other steps without departing from the scope and spirit of the present invention.

Turning now to FIG. 15, this figure illustrates a flowchart of an exemplary process 1500 for fabricating optical components that comprise a series of thin film layers that manage light 125 at an interface 275 between two optical material sections 220, 230 according to an embodiment of the present invention. While Process 1500, which is entitled Fabricate Component Comprising Index Transition, could be applied (directly or via adaptation) to multiple of the exemplary embodiments discussed herein, for illustrative purposes, reference will primarily be made to the system 1100 of FIG. 11 (discussed above) and the system 200 of FIG. 2 (also discussed above).

At Step 1510, a loading apparatus places a substrate 120 (not explicitly illustrated in FIG. 11) into the thin film deposition chamber. The loading apparatus can be a robot, a pick-and-place system, or a programmable arm, for example. A pump typically evacuates the chamber to a specified vacuum level, leaving at least some gaseous matter in the chamber.

At Step 1515, a deposition source emits high-energy particles of high-refractive index material, such as $Ta_2O_5$. The particles can be or can comprise atoms or molecules. In one exemplary embodiment, tantalum particles emitted from a tantalum source form $Ta_2O_5$ in the chamber, somewhere between the source and the substrate or at the substrate. In this case, the chamber can contain at least some gaseous oxygen that reacts with the tantalum.

The emitted particles adhere to the substrate 120 and accumulate to form a high index layer 220b. Feedback from an optical and/or a piezoelectric monitor in the chamber stops the deposition when the layer 220b achieves a sufficient thickness. The target thickness, which could be an optical thickness, an absolute thickness, a physical thickness, or a geometric thickness, can be derived from a computer-generated recipe for a thin film interference filter, for example. That is, a computer-based controller stops deposition when the layer 220b grows to a specified dimension.

At Step 1520, a deposition source in the chamber begins emitting high-energy particles of relatively low refractive index material, such as $SiO_2$. As discussed above, the source can comprise silicon dioxide or essentially pure silicon that reacts with oxygen to form silicon dioxide. Silicon dioxide adheres to the layer 220b and accumulates to form the layer 1125. The computer-based controller stops the deposition of silicon dioxide when feedback indicates that the layer 1125 has achieved sufficient thickness, for example a structure that has about ten atoms of silicon in a layer cross section.

At Step 1525, the deposition source begins emitting high-energy particles of $Ta_2O_5$. With the emission of $SiO_2$ suspended, the $Ta_2O_5$ accumulates to form the layer 1115, which adheres to the layer 1125 that formed at Step 1520. The controller suspends deposition of $Ta_2O_5$ when feedback indicates that the layer 1115 has grown to a specified thickness. That thickness specification can be in accordance with a computer-generated recipe or model, for example.

At inquiry Step 1530, the controller determines whether the transition layers have formed. For example, the controller determines whether each of the layers 1125, 1115, 1124, 1114, 1123, 1113, 1122, 1112, 1121, 1111, 1120, 1110 have formed according to the recipe. Process 1500 iterates Steps 1520 and 1525 until fabrication of those layers is complete. In other words, the controller repeats Steps 1520 and 1525 for each pair of high index and low index layers until the deposition chamber creates each transition layer.

As discussed above, the first iteration of Steps 1520 and 1525 forms layers 1125 and 1115. The second iteration forms layers 1124 and 1114. The third iteration forms layers 1123 and 1113. The fourth iteration forms layers 1122 and 1112. The fifth iteration forms layers 1121 and 1111. The sixth iteration forms layers 1120 and 1110. At each iteration, the thickness of the respective high index layer decreases while the thickness of the respective low index layer increases. The iterations may continue until 25, 50, or 100 pairs of transition layers have formed, for example.

Process 1500 executes Step 1535 (via a positive determination at inquiry Step 1530) in response to completing the formation of the layer 1110. At Step 1535, the deposition source emits particles of low index $SiO_2$ to form the layer 230b. The layer 230b typically is a counterpart to the layer 220b. For example, the layers 230b and 220b can cooperate to produce optical interference of the light 125 that the system 1100 is operative to manage (or constructive and destructive interaction between light waves).

At inquiry Step 1540, the controller determines whether formation of the entire stack 200 (shown in FIG. 2, discussed above) is complete. As discussed above, formation of the stack may follow a computer-generated recipe or design specification. If formation of the stack 200 is not complete, Process 1500 loops to Step 1515 to iterate Steps 1515, 1520, 1525, 1530, 1535, and 1540 until the deposition chamber has formed the stack 200.

When the stack 200 has completely formed, Step 1550 follows Step 1540. At Step 1540, the loading apparatus removes the completed assembly 200 from the deposition chamber for deployment in an application. Process 1500 ends following Step 1550.

As discussed above, a completed embodiment of the optical system 200, typically comprising multiple instances of the system 1100, may be deployed to benefit any of various applications. Those applications might include Raman spectroscopy, endoscopes, medical devices, optical networking modules, optical communication systems, flat panel displays, monofilament line, tissue analysis, cut jewels, diamonds, or laser reflectors, to name but a few examples.

Turning now to FIG. 16, this figure illustrates a flowchart of an exemplary process 1600 for using a series of thin film layers to manage light 125 at an interface 275 between two optical material sections 220, 230 according to an embodiment of the present invention. Process 1600, which is entitled Manage Light, will be discussed below with exemplary reference to FIG. 11, such reference being for illustrative purposes rather than as a limitation.

At Step 1610, light 125 propagates in the material section 230b towards the interface 275b or the adjacent material section 220b. The light 125 can comprise a DWDM signal, an optical packet, Raman-scattered light, an emission from a display pixel, amplified light from a silicon photonic device, etc. As discussed above, the material sections 220b and 230b have distinct material compositions and refractive indices.

At Step 1620, the light 125 is incident on or upon the layers 1110, 1120, 1111, 1121, 1112, 1122, 1113, 1123, 1114, 1124, 1115, 1125. As discussed above, those layers 1110, 1120, 1111, 1121, 1112, 1122, 1113, 1123, 1114, 1124, 1115, 1125 typically have alternating refractive index and composition, with each being essentially homogeneous.

At Step 1630, the light 125 propagates through or otherwise interacts with the layers 1110, 1120, 1111, 1121, 1112, 1122, 1113, 1123, 1114, 1124, 1115, 1125, for example in succession. The layers smooth, facilitate, or otherwise manage the transmission of the light 125 between the material section 230b and the material section 220b.

At Step 1640, the managed light 125 passes into the material section 220b. The managed light, transmitted therein, can have controlled reflection, polarization, spectral content, dispersion, delay, color, etc. Following Step 1640, Process 1600 ends.

Exemplary systems that may benefit from comprising transition layers 175 and methods that may benefit from comprising steps for managing light at an optical interface 275 will be discussed below with reference to FIGS. 17 through 29.

Figure 17A:
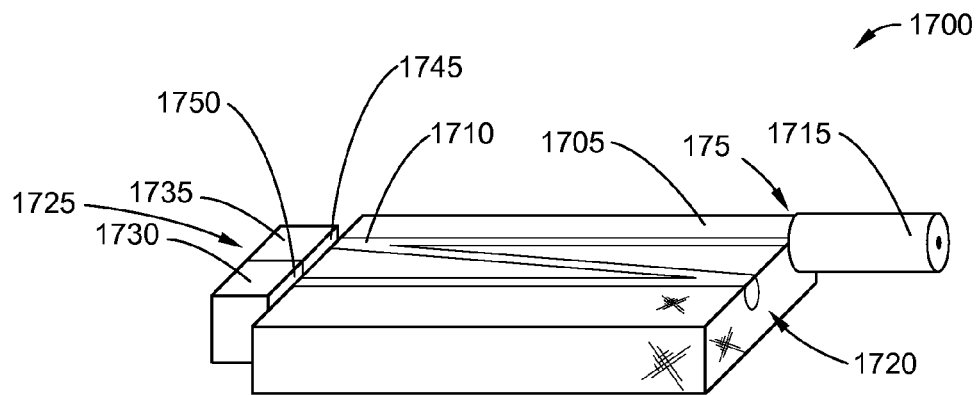
FIGS. 17A and 17B, collectively FIG. 17, respectively illustrate a representative perspective view and a functional block diagram of a system for receiving light with a detector, wherein the system adjusts the detector in advance of receiving the light in accordance with an exemplary embodiment of the present invention.
Figure 17B:
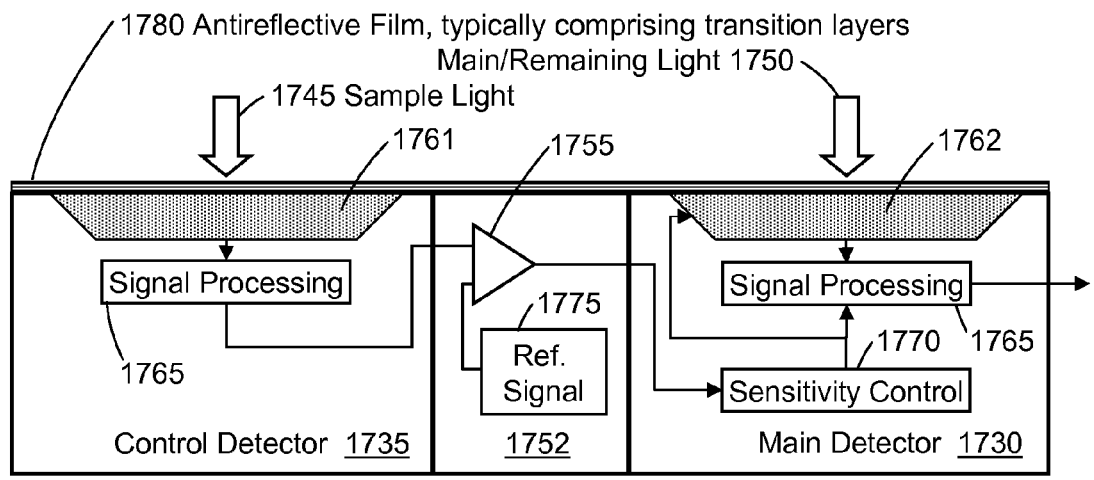

Turning now to FIGS. 17A and 17B, these figures respectively illustrate a representative perspective view and a functional block diagram of an exemplary system 1700 for receiving light 1750 with a detector 1725, wherein the system 1700 adjusts the detector 1725 in advance of receiving the light 1750 according to an embodiment of the present invention.

Dynamically configurable optical networks, such as DWDM networks that change transmission colors and/or routes, can be prone to delivering an unexpected change in light intensity to a receiving system 1700. If the intensity abruptly increases, some conventional receivers can become saturated, "blinded," temporarily impaired, or even permanently damaged. If the intensity abruptly decreases, some conventional receivers can suffer a bit error, for example failing to properly detect at least some aspect of the incoming signal. The self-adjusting or self-adaptation capability of the receiver system 1700 can help address or alleviate this issue.

The receiver system 1700 comprises an optical fiber 1715 that is connected to a network (not explicitly illustrated in FIG. 17), such as a SONET, Ethernet, FTTH, metro, access, DWDM, CWDM, optically reconfigurable, or LAN network. The optical fiber 1715 is connected to a planar lightguide circuit ("PLC") 1705 that is connected in turn to a detecting system 1725. The detecting system 1725 is typically an integrated circuit ("IC") device, such as an IC chip or a monolithic element. As an alternative to the PLC 1705, the system 1700 can comprise loops of fiber with a tap or a splitter or an optical delay system, for example.

In one exemplary embodiment, the PLC 1750 is or comprises a silicon optical amplifier or some other silicon-based integrated optical device. A silicon optical amplifier can output a signal that is correlated with the intensity of the traveling wave of light that is propagating in the amplifier. That output signal can feed into a detector that is coupled to the output of the silicon optical amplifier. More specifically, the output signal can adjust the detector in advance of the detector receiving the traveling wave of light, thereby enhancing the detector's performance in receiving that light.

In one exemplary embodiment, an imaging system (not illustrated) can trouble shoot the PLC 1750. A Raman imaging spectrometer can acquire an overhead image of the PLC 1750 while light transmits through the PLC waveguide core. The acquired image can help diagnosis any problems with the PLC 1750, in any the various embodiments discussed herein, for example. A problem or flaw in the waveguide core shows up on the image, as one or more intense pixels on the spectrometer's CCD, for example. Kaiser Optical Systems of Ann Arbor, Mich. is a supplier of high sensitivity imaging cameras and spectrometers.

The optical fiber 1715 emits light (typically encoded with communications data) into the PLC's waveguide core 1710. The waveguide core has a z-shaped configuration that operates to release a sample portion 1745 of the communications light to the detecting system 1725 and to direct the remaining portion 1750 of the light to the detecting system 1725 after a time delay. During the time delay, the detecting system 1725 self adjusts or adapts in preparation for receiving the main or remaining light 1750. Through the self adjustment, the detecting system 1725 can increase or decrease its sensitivity or take measures to avoid damage from an abrupt increase in intensity.

The input face 1720 of the PLC 1705 can have transition layers 175 adjacent the optical fiber 1715 to facilitate the transfer of light between the fiber 1715 and the PLC 1705. The transition layers 175 can enhance coupling between a glass fiber and a silicon-based PLC, such as one of the silicon photonic devices discussed above. Light propagates towards the PLC output face 1745. A sample 1745 of the incident light passes through the face 1745 for receipt by the control detector 1735. The face 1745 typically has a partially-reflecting thin film mirror, which may comprise a transition layer, that transmits about 1-5 percent of the incident light as the sample light 1745 and reflects 95-99 percent of the incident light.

The reflected light (which will become the main or remaining light 1750) propagates back to the opposite face 1720 of the PLC. A mirror coating (for example a dielectric or a metal mirror) on the opposite face 1720 reflects the remaining light 1750 back towards the output face 1750. The output face 1750 transmits the remaining light 1750 to the main detector 1730. The output face 1750 may comprise transition layers (not illustrated in FIG. 17 at that interface 1750) to facilitate the light transfer.

Accordingly, the control detector 1735 receives the sample light 1745 ahead of the main detector 1730 receiving the remaining light 1750. More specifically, an optoelectronic/opto-electric detecting region 1761 of the control detector 1735 receives the sample light 1745. Some time later, an optoelectronic/opto-electric detecting region 1762 of the main detector 1730 receives the main light 1750.

The signal processing module 1765 processes and amplifies the electrical signal that the region 1761 outputs in response to the sample light 1745. Thus, the control detector 1735 outputs an electrical signal that has an intensity that is related to or that is proportional to the intensity of the sample light 1745. The control module 1752 comprises a comparator 1755 that compares the electrical signal from the control detector 1735 to a reference signal 1775, which may comprise a voltage and/or a current.

If the signal from the control detector 1735 has greater intensity or magnitude than the reference signal 1775, the comparator 1755 outputs a control signal to the sensitivity control 1770 of the main detector 1730. The control signal may be binary or discrete or may alternatively have a range of values that indicate or convey the relative strength of the sample light 1745.

In response to the control signal from the comparator 1755, the sensitivity control module 1770 adjusts, adapts, or manages the optoelectronic/electro-optic region 1762 and the signal processing module 1765. For example, the sensitivity control module 1770 can tune the gain of the signal processing module. As another example, the sensitivity control module 1770 can apply a bias or a drain to the region 1762 based on input from the control module 1752.

Accordingly, the control detector 1735 receives sample light from light pulses and the main detector 1730 responds to the control signals from the control module 1752 in advance of the main detector 1730 receiving those light pulses. Thus, the main detector 1730 can receive optical pulses with high fidelity and can decode data from those pulses with high reliability.

Figure 18:
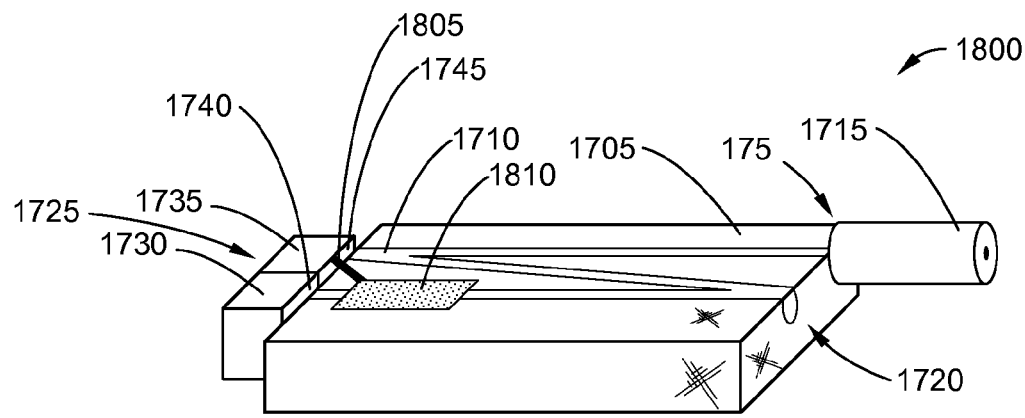
FIG. 18 illustrates a representative perspective view of a system for receiving light, wherein the level of received light is adjusted in advance of receiving the light in accordance with an exemplary embodiment of the present invention.

Turning now to FIG. 18, this figure illustrates a representative perspective view of an exemplary system 1800 for receiving light, wherein the level of received light is adjusted in advance of receiving the light according to an embodiment of the present invention. Accordingly, the system 1800 can be characterized as an exemplary embodiment of a receiver that self adjusts in advance of receiving a light pulse to better receive the light pulse.

Similar to the system 1700 illustrated in FIG. 17 and discussed above, the system 1800 can benefit from having transition layers 175 that manage the transfer of light at the interface between the detecting system 1725 and the PLC 1705 and/or the interface between the PLC 1705 and the optical fiber 1715.

The system 1800 comprises an optical attenuator 1810 that attenuates the light flowing in the PLC 1705 in response to control signals from the control detector 1735 of the detecting system 1725. The control detector 1735 receives sample light 1745 and controls the attenuator 1810 based on the strength of the sample light 1745. If the sample light 1745 is relatively intense, the attenuator 1810 attenuates the incoming light pulses in advance of detection by the main detector 1730. If the sample light 1745 is relatively weak, the attenuator 1810 allows a large portion of those light pulses to pass to the main detector 1730.

In an exemplary embodiment, the attenuator 1810 comprise a waveguide cladding with a controllable refractive index. Varying the refractive index sets the amount of light that leaks out of the cladding, thus providing controlled attenuation.

In one exemplary embodiment, the control detector 1735 and the module 1752 can determine and model the rate of change of the incoming sample light 1745, for example as a decaying exponential function or a time-constant response. The detecting system 1725 can control the main detector 1730 and/or the attenuator 1810 based on modeled change to compensate for the change. In other words, the system 1800 or the system 1700 can operate like a Smith predictor to make predictive changes that compensate for delay and time-constant dynamics. That is, the system 1800 can change the sensitivity of the main detector 1730 at a rate that tracks and compensators for the rate of change of the incoming optical signals before the main detector 1730 receives those optical signal.

Figure 19:
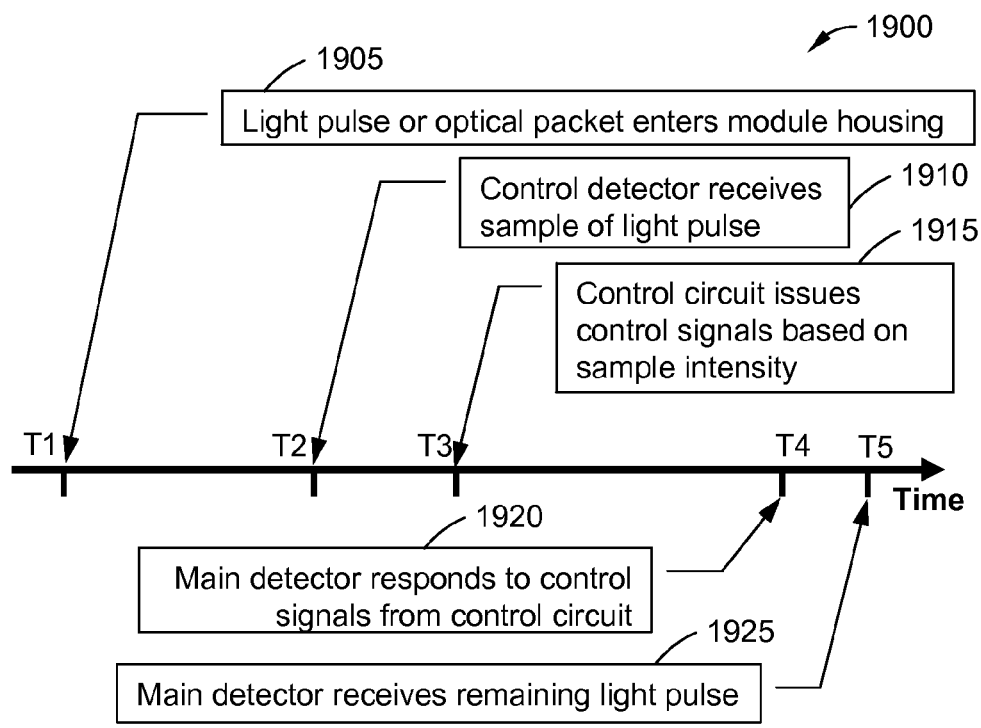
FIG. 19 illustrates a timing diagram of a system for receiving light with a detector, wherein the system adjusts the detector's sensitivity in advance of receiving the light in accordance with an exemplary embodiment of the present invention.

Turning now to FIG. 19, this figure illustrates a timing diagram 1900 of an exemplary system 1700 for receiving light 1750 with a detector 1762, wherein the system 1700 adjusts the detector's sensitivity in advance of receiving the light 1750 according to an embodiment of the present invention. The timing diagram 1900 is discussed with exemplary reference to the system 1700 of FIG. 17, discussed above.

At time T1 1905, a light pulse or an optical packet enters an optical networking module, such as a receiver, transceiver, or an optical add drop multiplexing terminal device.

At time T2 1910, the control detector 1735 receives a sample 1745 of the light pulse and converts that sample 1745 into the electrical domain.

At time T3 1915, the control circuit 1752 issues control signals or adjustment commands to the main detector 1730 based on the intensity of the sample 1745.

At time T4 1920, the main detector 1730 responds to the control signals from the control circuit 1752. The response can be a change in sensitivity, gain, etc.

At time T5 1920, the main detector 1730 receives the optical pulses that control detector 1735 sampled at time T2 1910.

Figure 20A:
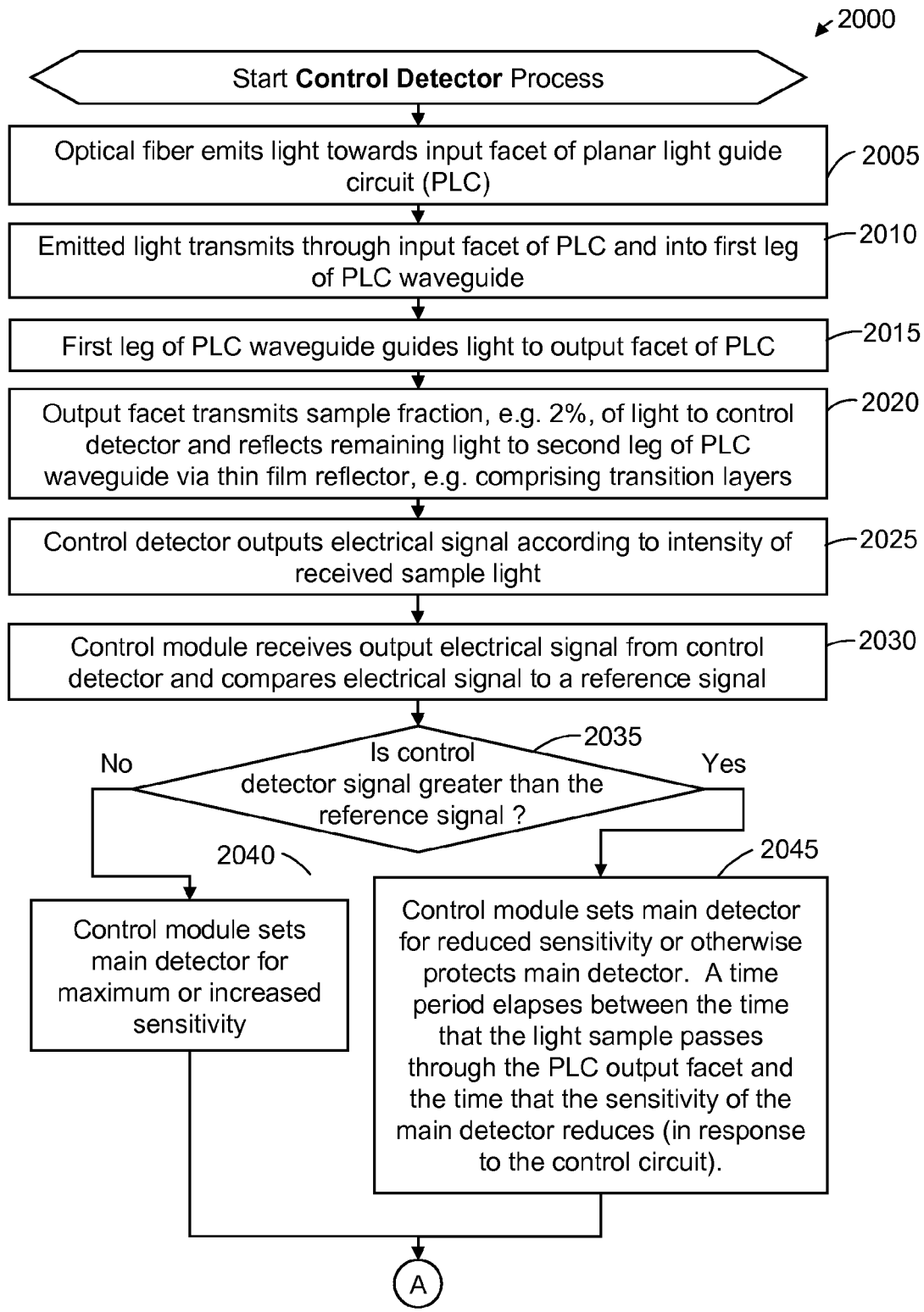
FIGS. 20A and 20B, collectively
Figure 20B:
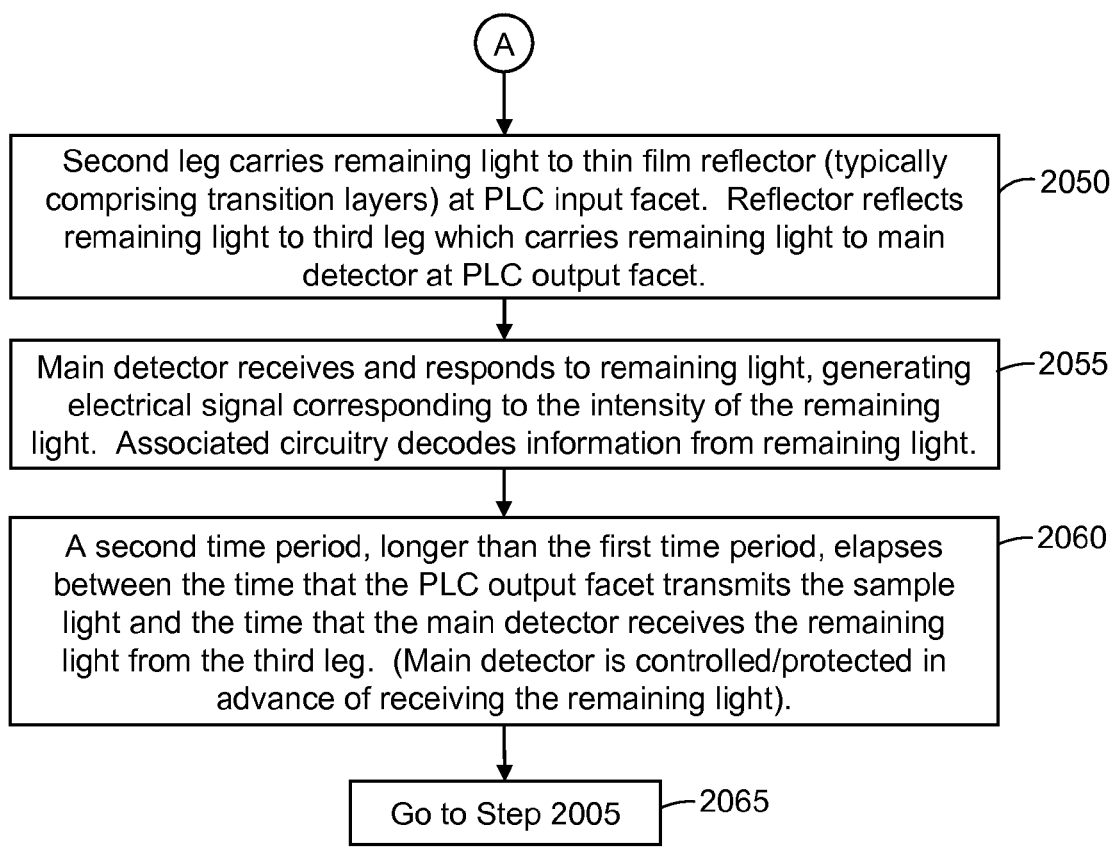

Turning now to FIG. 20, this figure illustrates a flowchart of an exemplary process 2000 for adjusting an optical detector 1730, based on an intensity of an optical signal, in advance of the detector 1730 receiving the optical signal according to an embodiment of the present invention. Process 2000, which is entitled Control Detector, will be discussed with exemplary reference to the system 1700 of FIG. 17, discussed above.

At Step 2005, the optical fiber 1715 emits light towards the input facet or face 1720 of the PLC 1720. At Step 2010, the emitted light transmits through the input face 1720 and into the first leg 1720 or a first section of waveguide core of the PLC 1705. At Step 2015, the first leg 1720 guides the light to an output face 1745, or a sample port, a tap, or a splitter, of the PLC 1720.

At Step 2020, the output facet 1745 transmits a sample portion 1745 of the light, such as 0.02 to 3 percent. The control detector 1735 receives that sample light 1745. The output facet 1745 directs the remaining light 1750 to a second leg of the PLC 1720. The light direction can be accomplished with a thin film reflector or an optical filter that can comprise a series of transition layers 175, as discussed above.

At Step 2025, the control detector 1735 generates an electrical signal that carries information about the intensity of the sample light 1745 that is incident thereon. In other words, the control detector 1735 converts the sample light 1745 from the optical domain to the electrical domain.

At Step 2030, the control module 1752, which can be viewed as a control circuit, compares the generated electrical signal to a reference 1775. At inquiry Step 2035, the control module 1752 determines whether the generated electrical signal is greater than the reference signal 1775, for example as a threshold test.

If the generated electrical signal exceeds the reference signal, then Step 2040 follows Step 2035. At Step 2040, the control module 1755 sets the main detector 1730 for maximum or heightened gain.

On the other hand, if the generated electrical signal does not exceed the reference signal, then Process 2000 executes Step 2045 following Step 2035. At Step 2045, the control module 1755 sets the main detector 1730 for reduced sensitivity. In one exemplary embodiment, the control module 1755 takes some other form of corrective action. Such action can include diverting light, attenuating light, blocking the main detector 1730 with a shutter, obscuring a portion of the remaining light 1759 with a variable diameter aperture, moving a MEMS element that control light, to name a few examples.

A time period elapses between the time that the light sample 1745 transmits through the face 1745 and the time that the main detector 1730 responds to the control signal from the control module 1752.

Following the execution of Step 2040 or Step 2045, as determined by inquiry Step 2035, Process 2000 executes Step 2050. At Step 2050, the second leg guides the remaining light 1750 to a reflector at the PLC face 1720. The second leg and the first leg may be "folded" with respect on one another. That reflector directs the light back to a third leg, which is folded with respect to the second leg. The third leg carries the remaining light 1750 back to the output facet 740. The remaining light 1750 passes through the output facet 740 towards the main detector 1730.

The zigzagged or folded first, second, and third legs can have a sufficient length to provide an adequate optical delay. In various exemplary embodiments, the legs can be 10 millimeters, 10 centimeters, or 100 centimeters in length, for example. In one exemplary embodiment, the PLC 1705 can have 10, 50, or 100 folded legs, rather than the exemplary number of three legs shown in FIG. 17. In one exemplary, the PLC 1705 is a backplane of a communications system or a signal buss.

At Step 2055, the main detector 1730 receives and responds to the remaining light 1750, thereby producing an electrical signal that corresponds to the intensity of that light 1750. Associated signal processing circuitry 1765, typically in concert with external circuitry, decodes information from the remaining light 1750. That information might comprise video signals, voice, data, etc.

At Step 2060, a second time period elapses between the point in time that the PLC output facet 1745 transmits the sample light 1745 and the point in time that the main detector 1730 receives the remaining light 1750. The second time period is longer than the first time period discussed above. Accordingly, the main detector 1730 is adapted or prepared for receipt of the remaining light 1750 in advance of actually receiving that light 1750.

At Step 2005, the execution of Process 2000 loops back to Step 2005, thereby iterating Steps 2005 through 2065. The iterations provide regular or essentially continuous updates to the reception characteristics of the main detector 1730.

Another exemplary method for receiving an optical signal can proceed in accordance with the following steps: (a) determining whether an optical signal has an intensity greater than a threshold in response to receiving a first portion of the optical signal at a first detector; and (b) if the intensity of the optical signal is determined to be greater than the threshold, adjusting a second detector for receipt of a second portion of the optical signal in advance of the second detector receiving the second portion.

Another exemplary method for receiving an optical signal can proceed in accordance with the following steps: (a) receiving a first portion of an optical signal at a first detector at a first time; (b) receiving a second portion of the optical signal at a second detector at a second time, after the first time; (c) determining whether the received first portion of the optical signal has an intensity that meets a threshold; and (d) if a determination is made that the received first portion of the optical signal has an intensity that meets the threshold, sending an alert for receipt at the second detector before arrival of the second portion of the optical signal at the second detector.

Another exemplary method for receiving an optical signal can comprise: (a) transmitting the optical signal into a watertight enclosure of a FTTH system at a premises; (b) monitoring whether the transmitted optical signal has changed in intensity as compared to a previously monitored intensity; (c) if the optical signal has changed in intensity adjusting a detector, within the enclosure, for receipt of the transmitted optical signal in advance the detector receiving the transmitted optical signal; and (d) receiving the optical signal with the adjusted detector.

Turning now to FIGS. 21A, 21B, and 21C, these figures illustrate a gemstone prior to 2150 and after 2100 applying an exemplary optical coating to a facet 2125, wherein the coating 2125 suppresses facet reflection 2165 according to an embodiment of the present invention. The coating 2125 can be or can comprise one or more transition layers 175. The coating 2125 manages the incident light 2105 at the interface between the gemstone 2100 and the surrounding medium, typically air.

A conventional gemstone, such as a conventional cut and uncoated diamond 2150, interacts with light 2105 via reflection 2165 and dispersion 2180. As a result of the large difference in refractive index between diamond and air, a large portion of incident light 2105 reflects 2165. At glancing angles, the fraction of reflecting light 2165 can be particularly high. The remaining light 2170 enters the diamond 2150 and is refracted by the diamond-air interface. The transmitted light 2170 internally reflects from the cut areas 2175 of the diamond 2150 and exits the upper facets, typically above the "girdle" or at the table facet. When the light 2180 exits, the light separates into a spectrum of colors, in a prismatic effect. The property of the diamond to separate light into colors in this manner can be referred to as the diamond's "fire." Oftentimes, diamonds that produce high levels of fire are desirable. However, the relatively large amount of light 2165 that is reflected prior to entering the diamond 2150 can limit the fire that the diamond 2150 yields.

Explained another way, an uncoated diamond 2150 reflects 2165 most of the light 2105 that is incident upon its table facet 2160. The remaining, un-reflected light 2170 enters the diamond 2150 and bounces around within the diamond 2150 and exits the diamond 2150 as multiple colors 2180, which may appear red, blue, yellow, green, etc. to an observer. Since a relatively little amount of light 2170 enters the diamond 2150, the intensity of those colors is relatively low. In other words, the reflection 2165 limits the intensity of the diamond's fire 2180.

In contrast, for the coated diamond 2100, the coating 2125 allows a larger portion 2120 of the incident light 2105 to penetrate the table facet 2125. That penetrated light 2120 reflects from within the internal surfaces 2175 and emerges as intense fire 2130. In other words, the coated diamond 2100 transmits most of the incident light 2105 and internally reflects that transmitted light 2120 towards the facets near the table facet 2125. The internally reflected light 2120 exits the diamond 2100 and disperses chromatically, or separates into visibly distinct colors 2130 that are more intense than the colored light 2180 of the uncoated diamond 2150. Thus, the coated diamond 2100 produces vivid or intense colors.

The coating 2125 can comprise an antireflective coating, a series of transition layers, a partially reflective coating, a motheye structure, or an "omnidirectional" filter, for example. Moreover, the transition layers can enhance the performance of an omnidirectional filter, an omnidirectional interference device, or an omnidirectional antireflective coating. Further, the coating can manage, control, or facilitate transmission of the incident light 2105.

The coating 2125 can be applied selectively to the table facet 2125, to other facets above the girdle or adjacent the table facet 2125, to all the facets above the girdle, or to the entire gemstone 2100, which can be a diamond, a cubic zirconium, a sapphire, a ruby, or some other jewel, for example. A cut gemstone can be masked and placed in a deposition chamber, for example.

Turning now to FIG. 22, this figure illustrates a flowchart of an exemplary process 2200 for using a thin film coating 2125 to suppress reflections 2115 from a facet 2125 of a gemstone 2100 and to enhance the gemstone's fire 2130 according to an embodiment of the present invention. Process 2200, which is entitled Enhance Fire, will be discussed with exemplary reference to FIG. 21C, discussed above.

At Step 2210, a deposition process applies a thin film antireflective coating to one or more facets or surfaces of a gemstone, jewel, or diamond 2100. A masking jig limits the coating deposition to a selected area, such as the table facet 2125. The thin film coating typically comprises one or more transition layers, as discussed above. Alternatively, the thin film coating may be a single layer of magnesium fluoride, for example. In some embodiments, the thin film coating may comprise organic material or polymers that can be removed with a solvent. Such removal can be desirable for some users who may want to temporarily use, test, or experiment with the coating, for example without risking permanent change to their jewelry.

At Step 2220, light rays 2105 propagate towards the coated table facet 2125 and are incident thereon. The coating 2125 generates optical interference that controls or suppresses light reflection 2115. At Step 2230, a relatively large percentage, such as 80%, 85%, 90%, 95%, 98%, 99% or in a range thereof, of the incident light 2105 passes through the table facet 2125 and into the diamond 2100.

At Step 2240, internal surfaces 2175 of the diamond 2100 reflect the light 2120 that has passed through the table facet 2125. That internally reflected light 2120 is directed back up towards the table facet 2125 and/or the adjacent facets.

At Step 2250, the internally reflected light 2120 exits the facets and is dispersed or separated into a spectrum of colors or vibrant color patterns 2130. The diamond 2100 has increased fire or color separation characteristics in response to the coating 2125. Following Step 2250, Process 2200 ends.

Turning now to FIG. 23, this figure illustrates an exemplary system 2300, comprising a series of apertures 2325, having progressively increasing diameter, that perform a mode expansion on light emitted from an optical fiber 2305 according to an embodiment of the present invention. The system 2300 can use diffraction to adiabatically expand a single mode of light from a single mode fiber, a crystal fiber, or a holey fiber, for example.

The optical fiber 2305 can comprise a core 2310 and a coating 2305 that includes series of transition layers 175 adjacent the fiber's end face to manage light at the optical interface between the fiber 2305 and the surrounding medium, typically air or some other gas.

The system 2300 comprises a series of plates 2320, membranes, members, films, layers, or some other structures with controlled spacing there between. Each plate 2320 has a thickness 2300 and comprises a hole 2325 that can be viewed as an aperture or a light port, for example. The thickness 2330 can be a ratio of the light flowing therein, for example. That ratio can be two fold, one fold, three-fourth, one-half, one-fourth, one-eighth, one-tenth, or in a range thereof, for example.

The holes 2325 have successively or progressively larger diameters. The diameters near the optical fiber can be about 10 microns or some other dimension that approximates the diameter of the fiber core 2310. The diameters 2325 can expand to about 20, 30, 40, or 50 microns or a factor of 1.5, 2, 2.5, or 3 times the core diameter. The system 2300 can comprise from 5 to about 50 plates 2320, for example.

The plates 2320 can have equal spacing 2335 that is related to the wavelength of the light. For example, the spacing 2325 can be provide a phase relationship. In other words, the plate-to-plate separation 2325 can help the plates provide a phased array of apertures 2325 that gradually expand a single-mode beam of light without unduly breaking the beam into two or more modes. The total length of the array of plates 2320 can be about 20 to 500 microns. The plates 2320 can be parallel to one another or slightly skewed to provide gradual curvature that bends, curves, slightly redirects the beam.

As an alternative to having air between each plate 2320, in one exemplary embodiment, the plates 2320 can be thin film layers that are integrally attached to one another. That is, the array of plates 2320 can comprise a stack of thin film layers with selected layers having a patterned metallic or other coating that has an aperture that functions as the hoe 2325. In other words, a solid structure of spaced apertures 2325 can function in a similar manner to the system 2300. More over, such as system can be bidirectional, to compress the mode or to expand the mode with little loss in intensity during the compression or expansion.

An embodiment of a stack of layers can be fabricated by depositing a first layer of transparent optical material. The first layer is then masked, for example with photolithography. A thin metallic layer is then deposited to form an opaque layer with an aperture 2325 corresponding to the masked area. Subsequent layers of transparent material and metal are deposited on top of the first layer. The thicknesses of the deposited layers are controlled to provide the distances 2325. The masked areas are controlled to provide progressively larger apertures 2325. In one exemplary embodiment, the stack also comprises an interference filter. That is, a stack of layers can comprise some layers that filter light via interference, some layers that expand the light beam, and/or some layers that both expand the light beam and filter light.

In one exemplary embodiment, the array of progressively larger apertures is implemented in a silicon system, such as a silicon photonic device or a silicon optical amplifier. In such embodiment, silicon or some other crystal can be grown or processed to provide the light-managing apertures 2325.

The system 2300 is typically enclosed in a sealed housing, such as a hermetic enclosure that also encloses a DWDM or CWDM laser, a FTTH receiver, a transceiver, a filter, or a detector, for example. In one exemplary embodiment the system 2300 and the system 1700, discussed above with reference to FIG. 17, are housed in a common optical networking module.

In one exemplary embodiment, the system 2300 processes light for coupling to an optical filter, for example one of the filtering devices or system discussed above. In particular, a thin film optical filter can be disposed adjacent the largest port 2325, so that the filter receives expanded-mode light, thereby providing enhanced filtering performance. That is, the system 2300 can present a filter with an expanded light beam to promote filtering. As discussed above, in one exemplary embodiment, the filter and the beam expansion system 2300 are an integrated or unitary system of thin film layers.

Turning now to FIG. 24, this figure illustrates a flowchart of an exemplary process 2400 for expanding a single mode light beam using diffraction associated with a series of progressively larger apertures 2325 according to an embodiment of the present invention.

At Step 2400 of Process 2400, which is entitled Expand Mode, a singe mode optical fiber 2305 transmits single mode light towards a fiber end face coated with an antireflective film 2315 or a system of transmission layers that manage light as discussed above. In one exemplary embodiment, a PLC, an optical amplifier, a semiconductor laser, or an optical waveguide transmits the light towards the system 2300.

At Step 2420, the optical fiber end face 2315 (or a tip of another waveguide) emits the single mode light, for example in a transceiver, a transmitter, or a receiver at a home premises. At Step 2430, the single mode light propagates through the apertures 2325 in a series of parallel plates 2320 or some other structures, as discussed above for example. The apertures 2325 have progressively increasing diameters along the light path.

At Step 2440, the apertures 2325, typically the peripheries or edges of the apertures, diffract the light or otherwise interact with the light via a wave-based phenomenon. At Step 2450, the diffraction helps the light beam expand while the majority of the light energy retains a single mode format.

At Step 2460, the expanded mode is incident on and is filtered by a thin film notch or band pass filter that may comprise transition layers 175 as discussed above. Following Step 2460, Process 2400 ends.

Turning now to FIG. 25, this figure illustrates an exemplary surgical system 2500 for cutting biological tissue by applying a light absorber 2580 and laser light 2575 to the tissue according to an embodiment of the present invention.

In many situations, conventional lasers that offer desirable energy-delivery characteristics deliver that energy at optical wavelengths that may fail to interact desirably with tissue. That is, a laser that would otherwise be well suited for surgical applications may output a color or wavelength that is ill suited to interacting with tissue.

For example, certain ultraviolet or visible lasers output light that is absorbed near or essentially at the tissue surface, with little uncontrolled penetration, in a manner that is desirable. However, the power characteristics of those lasers is often insufficient or is less than optimal. Thus, many convention ultraviolet or visible lasers offer limited performance for surgical applications.

On the other hand, while many conventional infrared lasers provide high power and/or delivery characteristics, the infrared light interacts with tissue over a greater depth or through a larger volume. Accordingly, conventional infrared lasers that can provide suboptimal light-tissue characteristics may be limited in the ability to target a surface layer of tissue.

The system 2500, illustrated in FIG. 25, can address this situation by adapting the tissue to enhance the manner in which the light 2575 interacts with the tissue or the manner in which the tissue responses to the light 2575. More specifically, the system 2500 can apply a localized ink 2580, a dye, a chemical, a light absorber, a moiety, an opaque solution, or another material that helps or induces the interaction between the light 2575 and the tissue. The laser light 2575 is incident upon the localized ink 2580 that has been applied to the tissue surface, and that ink 2580 rapidly absorbs the light 2575. The rapid absorption triggers a cascade or a chain reaction whereby the surface of the tissue also rapidly absorbs the light 2575.

For example, in response to the laser light 2575, the ink 2580 may heat so rapidly as to cause a transformation of the tissue immediately under the ink 2580, such as blackening, burning, charring, etc. The transformed tissue then readily interacts with the light 2575, and the tissue heats rapidly, burns, vaporizes, ablates, etc. Accordingly, a wavelength that might not otherwise readily cut, ablate, burn, incise, vaporize, or remove tissue can be used in surgery to provide cutting, ablation, burning, incising, vaporization, or removal of tissue.

In one exemplary embodiment, the ink 2580 helps limit the depth of the tissue that is cut by the laser light. In some situations, surgeons may apply the ink 2575 to a tissue surface that they wish to remove without harming the underlying tissue. For example, a surgeon might wish to kill malignant brain tumor cells without damaging nearby brain cells associated with an important brain function such as speech or eye sight. In this situation, the surgeon can insert the tip of the surgical handpiece 2530 into the brain at the tumor. After delivering the ink 2545 (or as the ink is being delivered), the surgeon can deliver a controlled burst of laser light 2575 that vaporizes or otherwise kills or destroys the tissue that is in direct contact the ink, while the underlying tissue can remain relatively unaffected. That is, the tumor cells can be destroyed while a critical nerve or a group of brain cells remains living or viable.

The system 2500 can comprise one or more transition layers 175 to help manage light flow at the various optical interfaces 275 that the system 2500 comprises. Such optical interfaces 275 can comprise the distal surface of the laser deliver optic 2550, the proximal end face of the optical fiber 2520, the optics of the infrared laser 2505 that launch laser light into the optical fiber 2520, or a mirror of the laser's lasing cavity, for example.

The infrared laser 2505 can be a semiconductor laser, an eximer laser, a tunable laser, or a gas laser, for example. In one exemplary embodiment, the infrared laser 2505 is a Nd:YAG laser or some other laser that outputs light between about 600 nanometers and 3,500 nanometers.

The optical fiber 2520 typically comprises a glass fiber having a core of about 600 to 1,000 microns and an outside cladding diameter of about 680 to 1,200 microns. A sheath typically protects the fiber 2520 from damage and helps shield operating room personnel from scattered light in the event that the fiber 2520 breaks or cracks. A tube 2525, such as a capillary tube, delivers the ink 2580 from the ink supply module 2510 to the surgical handpiece 2530.

In one exemplary embodiment, the ink delivery tube 2515 and the fiber 2520 are contained in a common sheathing or tube. In one exemplary embodiment, the ink supply 2510 and the infrared laser 2505 are housed in a common enclosure along with a microprocessor or some other computing device that helps control the delivery of laser light 2575 and ink 2545. In one exemplary embodiment, a sensor mounted at the distal tip of the surgical handpiece 2530 monitors the light-tissue interaction and/or the light-ink interaction. Monitoring information can feedback to the microprocessor for controlling light and/or ink delivery. The tip of the surgical handpiece 2530 can comprise a Raman probe, a fluorescence probe, an infrared probe, or an imaging device. The imaging device can comprise an optical coherence tomography ("OCT") tip, an imaging bundle of fibers, an ultrasound device, etc. Such a chemical, spectroscopic, or imaging sensor can provide images for viewing by the surgeon or sensor data for automatic feedback control.

The surgical handpiece 2530 typically comprises buttons or triggers 2535, 2540 through which the surgeon can control delivery of laser light 2575 and ink 2580. The surgeon can engage, depress, or squeeze the laser trigger 2535 to emit laser light 2575. Likewise, the surgeon can engage, depress, or squeeze the ink trigger to deliver ink 2580.

In one exemplary embodiment, the surgical handpiece 2530 comprises a knob or control for adjusting the rate of ink deliver. Also, the handpiece 2530 can comprise an adjustable nozzle for controlling the spray pattern of ink delivery. Thus, the surgeon can control whether the ink 2580 is delivered in a tight stream, in a mist, as a jet, or in some other pattern that the surgeon may desire for a particular surgical situation.

The light absorbing material or ink 2545 can comprise carbon, caramelized sugar, commercially available medical ink that is useful for marking incision lines in preparation for a surgical operation, an ink or colorant used for tattooing, a tattoo pigment, an organic or inorganic pigment, nano-particles, or a dye, to name a few examples. The ink 2545 can be viewed as an incision promoter or a compound that stimulates or control light-tissue interaction to achieve a surgical result. The delivered compound can be a compound that exhibits essentially no biological activity, rather than a drug that in and of itself stimulates a therapeutic effect. In one exemplary embodiment, the system 2500 delivers a medical-grade solvent along with the light absorbing material, and the solvent promotes penetration of the ink 2545 to a target tissue depth. In one exemplary embodiment, the system 2500 comprises replaceable ink cartridges, similar to the cartridges of an ink-jet printer.

Turning now to FIG. 26, this figure illustrates a flowchart of an exemplary process 2600 for cutting biological tissue by applying dye 2580 and laser light 2575 to the tissue according to an embodiment of the present invention. As discussed above with reference to FIG. 25, one or more steps of Process 2600, which is entitled Enhance Light-Tissue Interaction, can comprise a transition layer structure 275 managing light at an optical interface.

At Step 2610, a surgeon applies a light absorbing material, such as ink, dye, carbon, carbonized sugar, melanin, etc. to a tissue surface or boundary at which the surgeon desires to create an incision. The tissue boundary may be subcutaneous, for example within a body cavity or tissue structure that the surgeon accesses endoscopically. The light absorbing material can be comprise a solvent such as dimethyl sulfoxide ("DMSO") that promotes penetration of the light-absorber into the tissue. The light absorbing material can be a material that absorbs light via interaction between photons and the material's electron cloud. Alternatively, the interaction can involve chemical bond vibrations.

At Step 2620, the surgeon engages or prompts the laser system 2500 to deliver light, for example one or more pulses of light, to a selected area of tissue.

At Step 2630, in response to the surgeon's prompt, the gain medium of the laser 2505 energizes. Light resonates with the lasing cavity that can be bounded by a mirror comprising a series of transition layers 175. The surgical handpiece 2530 delivers the laser light 2575 to the tissue surface or boundary.

At Step 2640, the light absorbing ink 2580 absorbs the laser light and ablates, incises, cuts, vaporizes, damages, destroys, or removes the selected area of tissue. The light absorbing material helps create a light-tissue cascade or chain reaction. Such reaction can cause the tissue to rapidly react to the laser light 2575, via vaporization, boiling at a microscopic level, rapid expansion, burning, etc. The laser light 2575 can have a red or an infrared wavelength that would achieve less desirable surgical results were it not for the application of the ink 2580. Following Step 2640, Process 2600 ends.

A wide range of biological, medical, and biomedical applications, systems, and methods can benefit from managing light at an interface between two optical media. For example, analytical instruments can incorporate transition layers 175 for such light management.

Turning now to FIG. 27, this figure illustrates a flowchart of an exemplary process 2200 for analyzing tissue of an organism via acquiring spectra from the tissue while modulating the tissue's blood content and using the acquired spectra to compensate for blood content according to an embodiment of the present invention. The process 2200 is entitled Modulate Blood Flow to Tissue to Cancel Blood Influence on Tissue Analysis. If the system that acquires the spectra uses light, for example to acquire optical spectra, then the system can comprise transition layers 175 for light management at one or more optical interfaces.

At Step 2710, an analytical system acquires a spectrum from a selected site of an organism and stores the spectrum in memory. The organism can be a human, a mammal, or some other living thing. The analytical system can comprise an optical spectrometer, a Raman spectrometer, an OCT imaging device, a magnetic resonance system ("MRI"), a functional MRI, a CAT scanner, a CT-scanner, an infrared analyzer, a nuclear magnetic resonance ("NMR") system, a fluorescence instrument, a positive emission tomography ("PET") device, an ultrasound device, or an x-ray system, to name a few examples.

Blood flows freely to the selected site during or immediately preceding the spectral acquisition. Accordingly, the tissue at the selected site has a rich or normal content of blood when the spectrum is acquired. In one exemplary embodiment, the tissue site is artificially engorged with blood, for example via blocking a return vessel or by applying suction that will draw extra blood into the site.

Thus, the acquired spectrum comprises some contribution from the tissue itself and some contribution from the blood. In other words, the spectrum may have some structures that are associated with blood and some structures that are associated with other cells or chemical in the organisms. Such other cells or chemicals may comprise bone, muscular fibers, nerve cells, skin, hair, fat, artificial chemicals, drugs, pharmaceutical agents, brain cells, etc.

At Step 2720, transition layers 175 can manage light at any appropriate optical interfaces 175 that the analytical system comprises. Such optical interfaces 175 might include one or more of a laser, an optical fiber end face, a grating, a thin film filter, a light, an illumination system, an optical memory, a optical disk, a machine readable medium that is readable via light, an endoscope, an optical spectrometer, etc. Nonetheless, some analytical systems might not comprise such optical interfaces.

At Step 2730, the analytical system reduces or suppresses blood content in the selected tissue site. Various methods or systems can be used in connection with reducing blood content of the selected tissue site, a few of which will be discussed below.

In one exemplary embodiment, blood flow can be restricted from the site. Restricting blood flow can involve a surgeon clamping a feeder artery, an apparatus automatically pressing a pressure point that restricts flow in a blood conduit, such an artery. A medical assistant or a machine can apply a tourniquet or an inflatable cuff or bladder around the tissue site. In one exemplary embodiment, an air line can apply air pressure to the site to compress capillaries or other blood conduits. (The air line can also apply suction to drive blood into the site in connection with Step 2710 or some other step.)

In one exemplary embodiment, an application of a cold compress or ice can cause a capillary, artery, or vessel constriction. In one exemplary embodiment, a drug can be administered to reduce blood flow or to constrict capillaries. One such drug is nicotine.

In one exemplary embodiment, a beating heart can modulate the blood flow into and out of the site. For example, Step 2710 can be executed with the heart has driven blood into the tissue site. In this case, Step 2730 can comprise the heart pulling blood out of that tissue site.

At Step 2740, the analytical system acquires a spectrum from the selected tissue site and stores that spectrum in memory. The acquisition occurs while the level of blood in the site is lower than the blood level at Step 2710. That is, the analytical system can execute Step 2740 in parallel with or immediately following Step 2730 so that blood content of the tissue is at a reduced level during the spectral acquisition.

At Step 2750, that analytical system removes the stimulus that reduced blood content in the tissue at Step 2730. For example, the analytical system or some human may automatically or manually heat the tissue site that had been cooled, remove an occlusion or restriction from a feeder blood conduit, plug a draining blood conduit, remove a tourniquet, apply suction to the tissue site, etc. In one exemplary embodiment, the analytical system not only removes the cause of the reduced content but also stimulates blood flow into the tissue site. In one exemplary embodiment, the analytical system waits until the blood content returns to a normal level. In on exemplary embodiment, the analytical system or some person administers a chemical, drug, or pharmaceutical agent that increases blood flow. Such a stimulant could comprise epinephrine or adrenalin/adrenaline, for example. In one exemplary embodiment, the blood content at Step 2750 can be substantially different than the blood content at Step 2710.

At Step 2760, the analytical system has spectra that were acquired with the tissue site having high blood content and at least one sample acquired with the tissue having low blood content. The system may have a data analysis module that processes the spectrum acquired at Step 2710 and the spectrum acquired at Step 2750. For example, the data analysis module may average those spectra. Alternatively, the module may subtract those spectra to obtain a difference spectrum.

The data analysis module then subtracts the spectrum acquired when the blood content was high (or an average of the two high-blood-content spectra) from the spectrum acquired when the blood content was low. In other words, the analytical system makes a comparison between a spectrum that was acquired from the tissue and a relatively large amount of blood and a spectrum that was acquired from the tissue and a relatively low amount of blood. Accordingly, the data analysis module derives or infers a blood spectrum. That is, the analytical system produces a spectrum that has structures that can be primarily associated with blood and/or chemicals present in that blood.

At Step 2770, the analytical system uses the blood spectrum for diagnosis or for blood analysis. Such uses might include, among other possibilities, determining whether a particular blood protein, blood gas, pharmaceutical agent, drug, surgical gas, metabolite, or anesthesia, is present in the blood. Another example could be evaluating blood sugar or a glucose level. For example, an infrared or Raman analyzer could reference-out the impact of the tissue from spectra acquired of a finger or an arm, to produce a blood spectrum. And, that blood spectrum could be analyzed to determine blood sugar in connection with managing diabetes. Analyzing the blood spectra to determine blood sugar could comprise partial least squares analysis, regression analysis, artificial intelligence, Kalman filtering, spectral decomposition, or some other known spectral analysis.

At Step 2780, the analytical system acquires additional spectra from the tissue site. The spectral acquisition might be taken while the blood content was at a natural level, at an artificially heightened level, or at an artificially suppressed level.

At Step 2790, the data analysis module of the analytical system subtracts the inferred blood spectra from each of the additional spectra, thereby producing blood-compensated spectra. The data analysis module can scale the inferred blood spectra, for example to bring a selected "marker" peak in the blood spectra to a height that matches or correlates with the height of a particular portion of the subsequently acquired spectra.

For example, the data analysis module can use a spectral decomposition to amplify the blood spectrum so that when the amplified blood spectrum is subtracted from the subsequently applied spectra, the blood contribution is removed from those spectra.

At Step 2795, the data analysis module compares the compensated spectra to a catalogue or a database of normal tissue spectra. The comparison identifies deviations from normal or anomalies, thereby automatically indicating a possibility of a disease, a condition, or a malignancy, for example. The results can also be used for drug development, for example to help evaluate a pharmaceutical activity or the organism metabolizing a drug or some introduced chemical. Moreover, the results can aid administering a therapy or conducting surgery or some other medical procedure.

Following Step 2795, Process 2200 ends.

Exemplary embodiments in which a material is analyzed via directing a light beam through a sample and collecting light emanating from the sample 2825 will now be discussed with reference to FIGS. 28 and 29. In general, the systems can comprise a reflector disposed circumferentially around an illuminated portion of the sample. The illuminated portion of the sample can be cylindrical. The reflector can receive light emanating radially outward from the illuminated cylinder, can form a beam from the received light, and can direct the beam to a light processor or a light analyzer, such as a spectroscopic system, that deduces information about the sample based on the light.

Turning now to FIG. 28, this figure illustrates an exemplary optical system 2800 for optically characterizing a sample 2825 according to an embodiment of the present invention. The system 2800 can be used for analyzing biological samples, gas, wastewater, petroleum products, air, pollution, pharmaceutical materials, etc, manufacturing materials, feedstock, reactants, DNA samples, body fluids, etc.

The system 2800 comprises a laser 2805 that illuminates and/or energizes the sample 2825, which might be a gas, a gel, a liquid, or a matrix, for example. In one exemplary embodiment, the sample 2825 comprises nanoparticles and biological materials, for example a composition of a liquid, a DNA sample, and gold particles that help induce an amplified surface enhanced Raman scattering/spectroscopy ("SERS") effect from the DNA sample. In one exemplary embodiment, the sample 2825 comprises quantum dots, quantum dashes, or some form of artificially bound electrons. Such quantum dots can be attached to a constituent or a component of the sample 2825 to help determine whether that component binds or reacts with another component of the sample 2825, for example to facilitate a DNA, protein, or enzyme analysis. The sample 2825 can be in situ, in vivo, ex vivo, extractive, native, natural, prepared, or man-made, for example.

The laser 2805 can have a wavelength that is selected to provide or to accentuate a particular type of light-matter interaction. For example, the laser could be a green laser for conducting a Raman analysis of hydrogen gas, a near infrared laser for conducting a Raman analysis of a biological material that is subject to interfering fluorescence, or an ultraviolet ("UV") laser for fluorescent analysis, UV-resonant Raman analysis, or SERS.

The laser 2805 outputs a generally collimated beam 2815, typically comprising a cylinder of light propagating along an optical axis 2820. The beam 2815 thus illuminates a cylindrical portion of the sample 2825. After the laser beam 2815 passes through the sample 2825, a light trap 2855 or some other absorber collects the beam 2815, primarily to minimize uncontrolled reflections that could interfere with the material analysis.

As the laser beam 2815 propagates through the sample 2825, the laser photons interact with the sample 2815. The interaction can comprise Raman scattering, fluorescence, Mie scattering, SERS, elastic interaction, inelastic interaction, UV-resonance Raman scattering, stimulated Raman scattering, lasing, amplification, particle scattering, molecular vibrations, vibration of electron clouds, near infrared absorption, infrared absorption, or a combination thereof, to name a few examples.

The laser photons thus generate, stimulate, scatter, induce, or produce other photons from the sample, for example emitted from the sample via inelastic scattering. That is, in response to the laser beam 2815, emissions 2860 produce photons or emission rays 2865. At least a portion of those emission rays 2865 propagate radially outward from the laser beam 2815. Thus, the emission rays 2865 include rays that essentially intersect the optical axis 2820, somewhat analogous to spokes from an center of a wheel.

The emission rays 2865 propagating radially outward are incident upon the concave mirror 2810, which may have a form of an ellipsoid, a paraboloid, a revolved oval, an egg-shaped form, or an inwardly curved surface, to name a few examples. The concave mirror 2815, which has a port or an aperture 2830 for entry of the laser beam 2815, directs the emission rays 2865 to form a generally collimated beam 2850. The diversion of the collimated beam 2850 is controlled or has somewhat of a cylindrical shape, larger than the laser beam 2815.

More specifically, the emission rays 2865 propagate outward from the laser beam 2815, generally perpendicular to the optical axis 2820, and intersect the contoured surface of the concave mirror 2810. The contoured mirror surface reflects, deflects, or diverts the emission rays 2865 to provide redirected rays 2870 that collectively form the generally collimated beam 2850.

The mirror 2835 reflects the collimated beam 2850 at a generally right angle. The mirror 2835 has a port or a hole 2840 through which the laser beam 2805 passes. Alternatively, the mirror 2835 can comprise a dichroic optic that transmits the laser beam 2815 and reflects the collimated beam 2850 that is shifted in wavelength with respect to the laser light. Such a dichroic optic can comprise transition layers 175, as discussed above.

After being redirected by the mirror 2835, the collimated beam 2850 is incident upon the filter 200, discussed above with reference to FIG. 2. The filter 200 typically comprises a notch filter that reflects any laser light present in the collimated beam 2850 and transmits wavelength-shifted light associated with the emissions 2860, for example Stokes and/or anti-Stokes light. Accordingly, the filtered beam 2875 is principally composed of the emission rays 2870, and the beam 2875 has a well-defined or well-controlled geometric form.

The light processor 2880 receives the filtered beam 2875 and analyzes that beam 2875 to characterize the sample 2825. In one exemplary embodiment, the light processor 2880 comprises a spectrometer, spectrograph, or spectrophotometer based on a volume holographic transmission grating. In such an embodiment, the light processor 2880 can produce digitally recorded spectra of the emissions 2860. Candidate suppliers of such a light processor 2880 include Process Instruments, Inc. of Salt Lake City, Utah or Kaiser Optical Systems, Inc. of Ann Arbor, Mich. Thus, the light processor 2880 can separate the collimated beam 2850 into constituent wavelengths, measure the relative intensities of those constituent wavelengths, and determine the composition of the sample 2825 based on those measured intensities. For example, the system 2800 can determine biological information, such as DNA analysis, a biochemical reaction, or a drug activity, based on spectrographic analysis of the filtered light beam 2875.

In one exemplary, a process or method can be associated with the system 2800. That is, certain steps can involve the system 2800 to produce a material analysis. For example a method of light-based characterization, can comprise the steps of: (a) introducing particles, comprising artificially bound electrons, into a material; (b) directing essentially parallel rays of laser light, along an excitation axis, through the material; (c) responsive to the directing step, emitting rays of response light from the particles at locations along the excitation axis, the rays of response light substantially perpendicular to the excitation axis; (d) reflecting the emitted rays of the response light with a concave mirror having an optical axis essentially collinear with the excitation axis; (d) forming a bundle of essentially parallel rays of the response light, substantially aligned with the excitation axis, in response to the reflecting step; (e) separating the bundle of essentially parallel rays of the response light from the essentially parallel rays of the laser light; (f) filtering the bundle of essentially parallel rays of the response light; (e) coupling the filtered response light into a spectrograph; and (f) spectrally characterizing the response light.

In one exemplary embodiment, the introduced particles can comprise quantum dots. In one exemplary embodiment the response light is shifted in wavelength from the laser light.

In one exemplary embodiment, the method further comprises the steps of: (i) attaching at least one of the quantum dots to a component of the material if the component has an affinity for attachment; and (ii) determining whether the response light indicates attachment of the one quantum dot to the component in response to the spectrally characterizing step.

In one exemplary embodiment, a system for light-based characterization of particles can comprise: (a) an optical source that outputs a first beam through a sample comprising particles, wherein light emanates from the particles in response to the first beam; (b) a contoured mirror, circumferentially disposed around the illumination beam, operative to shape the emanated light into a second beam; (c) a light separator operative to separate the first beam from the second beam; and (d) a detector operative to detect a wavelength of the second beam.

In one exemplary embodiment, the particles comprise nanoparticles or quantum dots. In one exemplary embodiment, at least one of the particles is a molecule. In one exemplary embodiment, the light separator comprises a filter and the detector comprises a grating operative to disperse the second beam for reception by a detector array. In one exemplary embodiment, the light separator comprises an interference filter and wherein the first beam and the second beam are incident on the filter. In one exemplary embodiment, the light emanates from the particles via Raman scattering or fluorescence. In one exemplary embodiment, the light emanates from the particles in response to excitation of an artificially trapped electron of the particle. In one exemplary embodiment, the first beam and the second beam propagate in an unconfined manner along essentially co-linear optical axes. In one exemplary embodiment, the emanated light propagates in a substantially perpendicular direction, with respect to the first beam, between the first beam and the contoured mirror. In one exemplary embodiment, the emanated light emanates from the particles disposed in the first beam along a longitudinal section of the first beam.

In one exemplary embodiment, a second method for analyzing a material comprises the steps of: (a) emitting from a cylindrical volume of the material a first light, propagating radially, in response to illuminating the cylindrical volume with a second light; (b) forming a beam comprising the first light in response to reflecting the radially propagating first light; (c) separating the beam of the first light from the second light; and (d) analyzing the separated first light.

In one exemplary embodiment of the second method, the cylindrical volume comprises emitting a beam, comprising the second light, through the cylindrical volume. In one exemplary embodiment of the second method, the beam comprising the first light is a collimated beam, and illuminating the cylindrical volume comprises directing a substantially collimated beam that comprises the second light through the material. In one exemplary embodiment of the second method, reflecting the radially propagating first light comprises reflecting the radially propagating first light with a concave mirror having an optical axis that passes through the cylindrical volume. In one exemplary embodiment of the second method, the beam of the first light comprises collimated light propagating in free space. In one exemplary embodiment of the second method, the material comprises nanoparticles, and the emitting step further comprises emitting the first light from the nanoparticles. In one exemplary embodiment of the second method analyzing the separated first light comprises conducting a spectral analysis. In one exemplary embodiment of the second method, the second light comprises laser light, illuminating the cylindrical volume with the second light comprises illuminating the cylindrical volume with essentially parallel rays of the laser light, and the beam comprises essentially parallel rays of the first light.

Turning now to FIG. 29, this figure illustrates an exemplary optical system 2900 for optically characterizing a sample 2825 according to an embodiment of the present invention. The system 2900 comprises a resonant or semi-resonant optical cavity 2975 or etalon between the partial reflector 2925 adjacent the laser 2805 and the partial reflector 2926 located at a standoff distance from the laser 2805. The partial reflectors 2805, 2806 can provide broadband reflectivity or alternatively can reflect a narrow range of colors or wavelengths, while transmitting other colors or wavelengths outside that range.

The cavity 2975 sets up a standing wave between the partial reflectors 2805, 2806 that imparts the laser beam 2815 with higher intensity in the cavity 2975 that outside the cavity 2915. Thus, the cavity 2975 can be viewed as providing an intensified or amplified region of the laser beam 2815. Outside the cavity 2975, the mirror 2935 diverts the laser beam 2815 (outside the amplified cavity region) to the light trap 2855.

In one exemplary embodiment, the laser intensity in the cavity 2975 is sufficient to excite the sample 2825 to a lasing, near lasing, or a stimulated state. That is, the laser 2805 can pump the sample 2825 towards causing the sample 2825 to lase or to emit stimulated radiation. In one exemplary embodiment, the lasing cavity of the laser 2805 extends to the partial reflector 2925, thereby providing a lasing cavity that the mirrored surface 2910 surrounds.

Whether via spontaneous emissions, stimulated emissions, scattering, or some other interaction between matter and photonic radiation, the laser light in the cavity 2975 provides emissions 2860 and associated light rays 2865 that travel outward from the optical axis 2820. The contoured mirror 2910 that circumferentially surrounds the cavity 2975 and the illuminated sample 2825 collimates the light rays 2865 and directs them towards spectrometer 2980, as the beam 2850. That is, the concave mirror 2910 reflects the emission rays 2865 to create a beam 2850 of essentially or generally parallel rays headed towards the spectrometer 2980.

The filter 200, discussed above as an exemplary embodiment, rejects residual laser light and transmits the light that is wavelength shifted, e.g. to the red or to the blue, as the filtered beam 2875. The spectrometer 2980, which can be a spectrophotometer, creates a digital spectrum of the emitted light 2865 that can characterize the sample 2825 or some property thereof. The spectrometer 2980 typically comprises or is linked to a computing system that performs spectral analysis and that includes a data storage device, a processor, and spectral analysis software.

Thus, the system 2900 can evaluate the sample 2825 based on the relative wavelength intensities of the emitted or scattered light 2865 that emanates radially outward from the portion of the sample 2825 disposed in the cavity 2975.

In summary, the present invention can support managing light at an optical interface to benefit a wide range of devices, processes, and applications—a representative few of which have been discussed above as examples.

From the foregoing, it will be appreciated that the present invention overcomes the limitations of the prior art. Those skilled in the art will appreciate that the present invention is not limited to any specifically discussed application or implementation and that the embodiments described herein are illustrative and not restrictive. From the description of the exemplary embodiments, equivalents of the elements shown herein will suggest themselves to those skilled in the art, and ways of constructing other embodiments of the present invention will appear to practitioners of the art. Therefore, the scope of the present invention is to be limited only by the claims that follow.

What is claimed is:

1. An optical filter comprising:
   a series of thin film optical interfaces, each formed between a respective high index thin film layer and a respective low index thin film layer; and
   a respective series of transition layers of alternating refractive indices disposed at each thin film optical interface in the series of thin film optical interfaces, each respective series of transition layers comprising:
     high index transition layers disposed in one of the respective low index thin film layers; and
     low index transition layers disposed in one of the respective high index thin film layers, and
   wherein the high index thin film layers and low index thin film layers and the series of transition layers of alternating refractive indices collectively provide a sinusoidal variation in refractive index or collectively provide a refractive index profile having the form of a square wave with rounded corners.

2. The optical filter of claim 1, wherein the high index transition layers and the high index thin film layers have common compositions.

3. The optical filter of claim 1, wherein one or more of the high index transition layers and one or more of the high index thin film layers have a common composition.

4. The optical filter of claim 1, wherein a particular thin film optical interface is formed between a particular low index thin film layer having a first refractive index and a particular high index thin film layer having a second refractive index,
   wherein the series of transition layers disposed at the particular thin film optical interface comprises high index transition layers of the second refractive index disposed in the particular low index thin film layer.

5. The optical filter of claim 1, wherein a particular thin film optical interface is formed between a particular low index thin film layer having a first refractive index and a particular high index thin film layer having a second refractive index,
   wherein the series of transition layers disposed at the particular thin film optical interface comprises low index transition layers of the first refractive index disposed in the particular high index thin film layer.

6. The optical filter of claim 1, comprising low index transition layers no thicker than about ten nanometers and high index transition layers no thicker than about ten nanometers.

7. The optical filter of claim 1, wherein one or more of the low index transition layers and one or more of the low index thin film layers have a common composition.

8. The optical filter of claim 1, wherein one of the low index transition layers and one of the low index thin film layers comprise a first refractive index, and wherein one of the high index transition layers and one of the high index thin film layers comprise a second refractive index that is substantially higher than the first refractive index.

9. The optical filter of claim 1, wherein each one of the low index transition layers of at least one of the series of transition layers of alternating refractive indices is thinner than the previous low index transition layer of the series.

10. The optical filter of claim 1, wherein each one of the high index transition layers of at least one of the series of transition layers of alternating refractive indices is thinner than the previous high index transition layer of the series.

11. An optical filter comprising:
    high index thin film layers interleaved with low index thin film layers to form a periodic series of optical interfaces; and
    a respective system of alternating refractive index transition layers disposed at each of the optical interfaces,
    each system of alternating refractive index transition layers comprising:
      high index transition layers disposed in one of the interleaved low index thin film layers; and
      low index transition layers disposed in one of the interleaved high index thin film layers, and
    wherein the high index thin film layers interleaved with low index thin film layers and the systems of alternating refractive index transition layers collectively provide a sinusoidal variation in refractive index or collectively provide a refractive index profile having the form of a square wave with rounded corners.

12. The optical filter of claim 11, wherein each of the high index transition layers has a respective thickness that is less than ten nanometers, and
    wherein each of the low index transition layers has a respective thickness that is less than ten nanometers.

13. The optical filter of claim 11, wherein each system of alternating refractive index layers comprises progressively thinner layers.

14. The optical filter of claim 11, wherein each respective one of the high index transition layers of one of the systems of alternating refractive index transition layers is thinner than the previous respective one of the high index transition layers in the system, such that the high index transition layers of the system are progressively thinner.

15. The optical filter of claim 11, wherein each respective one of the low index transition layers of one of the systems of alternating refractive index transition layers is thinner than the previous respective one of the low index transition layers in the system, such that the system comprises progressively thinner low index transition layers.

16. An optical filter comprising:
    a periodic arrangement of optical interfaces, individually operative to transmit and reflect incident light and collectively operative to filter light via optical interference,
    wherein each of the optical interfaces is formed between two respective layers of optical materials having contrasting refractive indices, with a respective series of transition layers of contrasting refractive index extending across each of the optical interfaces,
    wherein each respective series of transition layers comprises:
      a first plurality of transition layers disposed in a first of the two respective layers of optical materials; and
      a second plurality of transition layers disposed in a second of the two respective layers of optical materials, and
    wherein the layers of optical materials having contrasting refractive indices and series of transition layers of contrasting refractive index collectively provide a sinusoidal variation in refractive index or collectively provide a refractive index profile in the form of a square wave with rounded corners.

17. The optical filter of claim 16, wherein each respective series of transition layers is periodic.

18. The optical filter of claim 16, wherein the first plurality of transition layers and the second of the two respective layers have substantially common refractive indices, and wherein the second plurality of transition layers and the first of the two respective layers have substantially common refractive indices.

19. The optical filter of claim 16, wherein the first plurality of transition layers and the second of the two respective layers have substantially common composition, and wherein the second plurality of transition layers and the first of the two respective layers have substantially common composition.

20. The optical filter of claim 16, wherein each of the first plurality of transition layers disposed in the first of the two respective layers of optical materials is less than about ten nanometers in thickness.

\* \* \* \* \*